US011122775B2

(12) United States Patent
Coyle

(10) Patent No.: US 11,122,775 B2
(45) Date of Patent: Sep. 21, 2021

(54) PHOTODENTAL DEVICE FOR ANIMALS

(71) Applicant: Brian Michael Coyle, Canyon, CA (US)

(72) Inventor: Brian Michael Coyle, Canyon, CA (US)

(*) Notice: Subject to any disclaimer, the term of this patent is extended or adjusted under 35 U.S.C. 154(b) by 83 days.

(21) Appl. No.: 15/992,740

(22) Filed: May 30, 2018

(65) Prior Publication Data

US 2019/0124888 A1 May 2, 2019

Related U.S. Application Data

(60) Provisional application No. 62/579,887, filed on Nov. 1, 2017.

(51) Int. Cl.
*A01K 15/02* (2006.01)
*A61N 5/06* (2006.01)
(Continued)

(52) U.S. Cl.
CPC .......... *A01K 15/026* (2013.01); *A61N 5/062* (2013.01); *A61N 5/0603* (2013.01);
(Continued)

(58) Field of Classification Search
CPC .. A01K 15/026; A01K 15/025; A01K 27/002; A01K 27/006; A01K 1/0263;
(Continued)

(56) References Cited

U.S. PATENT DOCUMENTS 5,968,036 A * 10/1999 Goodman ............... A61B 18/20
606/12
7,389,020 B2  1/2008 Dixon
(Continued)

OTHER PUBLICATIONS

Tordis Trovik, Kristen Klock, Ola Haugejorden, Trends in reasons for tooth extractions in Norway from 1968 to 1998, Acta Odontologica Scandinavica, 2000, 58:2, 89-96, Taylor & Francis, UK.
(Continued)

*Primary Examiner* — Peter M Poon
*Assistant Examiner* — Jeffrey R Larsen

(57) ABSTRACT

The present disclosure relates to a photodental device that can deliver specific light wavelengths to animal oral cavities, particularly dogs. The device may be provided in a variety of shapes, sizes, and materials, for breeds from under 2 kg (4.4 lbs) to over 115 kg (254 lbs). The device has a container which may protect light sources and may be used to receive light transmission, comprising an illuminating member. The device can further include replaceable housings with photoactivated compounds. The device may be configured for untethered use by an animal. Alternatively, the electro-optical components can be placed in a separate body and transmit light through a tethered connection to a member used by an animal. Sensor components may activate light generation components in predetermined conditions. Alternatively, humans may control activation. The present disclosure also relates to methods of photodentistry using the photodental device as bactericidal treatment and periodontal treatment.

13 Claims, 32 Drawing Sheets

(51) Int. Cl.
    *A01K 29/00*         (2006.01)
    *A01K 13/00*         (2006.01)

(52) U.S. Cl.
    CPC .......... *A61N 5/0624* (2013.01); *A01K 13/001* (2013.01); *A01K 29/00* (2013.01); *A61N 2005/063* (2013.01); *A61N 2005/0606* (2013.01); *A61N 2005/0645* (2013.01); *A61N 2005/0662* (2013.01)

(58) Field of Classification Search
    CPC ................ A01K 27/008; A01K 15/021; A46B 2200/1086; A61D 5/00
    USPC ......................................... 119/707, 792, 799
    See application file for complete search history.

(56) References Cited

U.S. PATENT DOCUMENTS

| | | | |
|---|---|---|---|
| 7,329,273 B2* | 2/2008 | Altshuler | A46B 15/0002 433/29 |
| 8,124,156 B2 | 2/2012 | Axelrod | |
| 8,776,729 B2 | 7/2014 | Koo | |
| 9,198,502 B2 | 12/2015 | Barnes | |
| 9,457,199 B2 | 10/2016 | Lin | |
| 9,927,080 B2 | 3/2018 | Dahlen | |
| 2005/0004631 A1* | 1/2005 | Benedict | A61N 5/0619 607/88 |
| 2005/0221251 A1* | 10/2005 | Soukos | A61C 19/06 433/29 |
| 2009/0191504 A1* | 7/2009 | Mannino | A61B 5/0088 433/29 |
| 2017/0326383 A1* | 11/2017 | Soukos | A61N 5/0603 |

OTHER PUBLICATIONS

Mark Marshall, Corrin Wallis, Lisa Milella, Alison Colyer, Andrew Tweedie, Stephen Harris, A longitudinal assessment of periodontal disease in 52 miniature schnauzers, BMC Veterinary Research 2014, 10(166):1-13, Springer-Verlag London.

D. Sambunjak, J.W. Nickerson, T Poklepovic, T.M. Johnson, P. Imai, P. Tugwell, H.V. Worthington, Flossing for the management of periodontal diseases and dental caries in adults (Review), The Cochrane Library 2011, Issue 12:1-60, John Wiley& Sons, Hoboken.

T. Poklepovic, H. Worthington, T. Johnson, D. Sambunjak, P. Imai, J. Clarkson, P. Tugwell, Interdental brushing for the prevention and control of periodontal diseases and dental caries in adults, Cochrane Database of Systematic Reviews, 2013:12, 1-54, John Wiley& Sons, Hoboken.

M. Yaacob, M. Worthington, H. Deacon, A. Scott, C. Deery, A. Walmsley, P. Robinson, A. Glenny, Powered versus manual toothbrushing for oral health, Cochrane Database of Systematic Reviews, 2014:6, 1-105, John Wiley& Sons, Hoboken.

Christiane Pereira, Anna Costa, Claudia Carreira, Juliana Junqueira, Antonia Jorge, Photodynamic inactivation of *Streptococcus mutans* and *Streptococcus sanguinis* biofilms in vitro. Lasers in medical science, 2012, 28(3): 859-864, Springer-Verlag London.

Anna da Costa, Jose Junior, Milton Beltrame, Juliana Junqueira, Susceptibility of planktonic cultures of *Streptococcus mutans* to photodynamic therapy with a light-emitting diode, Brazilian Oral Research, Oct.-Dec. 2010, 24(4):413-8, Brazil.

Dental Scaling Without Anesthesia, American Veterinary Dental College Website, https://www.avdc.org/dentalscaling.html.

Min-Jeong Kim, Photodynamic Inactivation by 405±5 nm Light Emitting Diode Against Foodborne Pathogens, PhD Thesis, University of Singapore, 2016, 106-128, Singapore.

M. Barneck, N. Rhodes, M. La Presa, J. Allen, A. Poursaid, M. Nourian, M. Firpo, J. Langell, Violet 405-nm light: a novel therapeutic agent against common pathogenic bacteria, Journal of Surgical Research, Dec. 2016, 206(2):316-324, Elsevier, Atlanta.

M. Maclean, S. Macgregor, J. Anderson, G. Woolsey, Inactivation of Bacterial Pathogens following Exposure to Light from a 405-Nanometer Light-Emitting Diode Array, Applied Environ Microbiol., Apr. 2009, 75(7):1932-7, Am. Society Microbiol., Washington DC.

A. Pummer, H. Knuttel, K. Hiller, W. Buchalla, F. Cieplik, T. Maisch, Antimicrobial efficacy of irradiation with visible light on oral bacteria in vitro: a systematic review, Future Medicinal Chemistry, 2017, 9(13). 1557-1574, Future Medicine Ltd., London, UK.

F. Halstead, J. Thwaite, R. Burt, T. Laws, M. Raguse, R. Moeller, M Webber, B. Oppenheim, Antibacterial Activity of Blue Light against . . . Pathogens Growing Planktonically and as Mature Biofilms, Applied Environ Microbiol., 2016, 82(13): 4006-4016, Am. Society Microbiol., DC.

Francois Delori, Robert Webb, David Sliney, Maximum permissible exposures for ocular safety (ANSI 2000), with emphasis on ophthalmic devices, Journal Opt. Soc. America, 2007, 24(5): 1250-1265, OSA Publishing, Washington DC.

G. Ziegelberger, ICNIRP Guidelines on Limits of Exposure to Incoherent Visible and Infrared Radiation, Health Physics, 2013, 105(1):74-96, Lippincott Williams & Wilkins, Philadelphia.

* cited by examiner

PHOTODENTAL DEVICE FOR ANIMALS

CROSS-REFERENCE TO RELATED APPLICATIONS

The present application claims benefit under 35 USC § 119(e) of U.S. Provisional Patent Application Ser. No. 62/579,887 filed on 1 Nov. 2017. The present application is based on and claims priority from this application, the disclosure of which is hereby expressly incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

The present invention relates to a new instrument for treating animals' teeth (Class. A61D 5/00), in particular an apparatus adapted for a specific treatment for eliminating microbes, germs, bacteria on or in the body (Class. A61N5/0624), using photodynamic therapy (Class. A61N5/062), in particular radiation therapy using light characterized by the wavelength of light used (Class. A61N2005/0658) produced by an illuminating device (Class. A61C1/088) to clean by radiant energy (Class. B08B7/0035) for animal, especially dog, dental prophylaxis (Class. A61C17/005). The device emits radiation, in the violet and/or blue region of the visible spectrum, between 400 nm and 500 nm, in order to:
- kill pathogenic oral bacteria in planktonic and biofilm states, including P. gingivicanis and F. nucleatum, on teeth, oral mucosa tissue, gingiva, and adjacent structures in the mouths of animals, in particular dogs.
- activate photosensitive compounds distributed on the teeth and the gums of an animal, in particular a dog, through said animal's mastication of the device's housing.

This invention reduces the load of, destroys the structure of, and suppresses the activity of the dental disease causing bacteria and biofilms that inhabit animal, in particular dog, mouths. And, more specifically, the present invention relates to light emitting systems and devices that fit in dog chew toys, from where they attack disease causing bacteria inside of dog mouths, as these bacteria absorb visible bactericidal radiation that is safe for animals, in particular dogs.

Background of the Invention—Dillemas, Issues, Problems

The current art in dog dental disease prevention borrows current art in human dental health. The oral care practice for humans the dentistry profession most strongly supports is fluoride applied with tooth brushing. This effectively attacks the primary cause of human dental disease, the bacterium *Streptococcus* mutans. Brushing is assumed to work for other species, though most dog pastes do not contain fluoride. Veterinarians advise pet owners to brush their dog's teeth as often as their own. Brushing evolved in concert with cultural attitudes about human hygiene, is inculcated in childhood, and takes place in an omnivore's mouth. Dogs aren't humans, aren't trained to accept people's hands in their mouths, and have a predator's mouth. Despite veterinarian efforts, people rarely brush their dog's teeth, because neither dogs nor people feel comfortable about it.

Dogs don't have the same dental disease problems that humans do. For a Norwegian (human) cohort born circa 1948, >90% of tooth loss at age 20 was due to caries. By 40, 52% were lost to caries and 26% to periodontal disease (PD). At age 52 PD tooth loss increased to 42%, same as caries. Only in advanced age does PD become the most significant oral health problem for humans (Trovik et. al, 2000, 1). Dogs have the opposite problems. Prevalence of caries in dogs is ~5%. But 84% of beagles over 3 years have PD, and 100% of poodles over age 4. A study of multiple breeds found an 86% PD rate at any age (Marshall et. al, 2014, 2).

Dog mouth environments have higher pH than human mouths, and wide interdental spaces people lack. This promotes entirely different bacterias: only 16.4% of the taxa in canine and human plaque are common. *S. mutans* do not adhere to dog teeth. Dogs are exposed to a larger, more diverse microbial community than humans. This leads to more biofilm formation. Dog interdental papilla support Gram negative PD bacteria such as *Porphyromonas* and *Tannerella*. Dentists do not advise brushing oral mucosa tissues, where PD bacteria thrive, as it may inflame them. Current art for pet owners to care for their own pet's, in particular a dog's, mouth, does not address PD.

The current art of oral self-care to prevent or treat human PD is itself, surprisingly, not well established. Studies assume plaque removal prevents more serious disease, though the etiology is incomplete. In the largest, most recent review articles on brushing and flossing, on powered toothbrushes, and on Chlorhexidine mouthwash, none had evidence of clinical effect against PD (Sambunjak, 2011, 3, Poklepovic, 2013, 4, Yaacob, 2014, 5).

In the late 2000s, research into *S. mutans* suggested photodynamic light could kill it. Patents were issued to use photodynamic light in human mouths for this purpose, generally in the form of toothbrushes. U.S. Pat. No. 9,198,502 to Barnes et al. (P1) promotes human oral hygiene by radiating LED light in the mouth, claiming it kills *S. mutans*. More recent research shows that photodynamic light alone does not kill *S. mutans*, unless combined with photosensitisers. Pereira et. al (2012, 6) used non-collimated light (LED) for 5 minutes, with no impact on *S. mutans* without photosensitisers. da Costa et. al (2010, 7) exposed *S. mutans* planktonic cultures to 95 J/cm2 of 440-460 nm LED light, and found no bacterial impact without photosensitisers. Recent patents employ pastes with photosensitisers. U.S. Pat. No. 9,457,199 to Lin (P2) describes a light emitting toothbrush for humans, to whiten teeth and destroy bacteria, in concert with a radiation responsive paste.

Toothbrush emitters are not scientifically sound. Research shows oral bacteria need 5+ minutes of high intensity light to absorb a dosage sufficient for disablement. Dentists oppose brushing teeth for that long, as it removes dentin. People aren't habituated to it.

Human photodynamic toothbrushes and products don't work well for people, and are completely inappropriate for dogs:

1. Dogs can crush them.
2. Brush emitters illuminate teeth. Dogs need light between teeth.
3. Most dogs do not accept a human holding an object in their mouths for 5 minutes.
4. Gram-negative PD bacteria need different photosensitisers than Gram-positive *S. mutans*, and possibly different light wavelengths.
5. The greatest problem facing pet owners is that they don't feel safe brushing their dog's teeth. No solution that involves people manipulating objects in dog mouths will be accepted.

Dogs like to chew, and firms market antibacterial chews and hard mastication toys that may help reduce bacteria. U.S. Pat. No. 8,776,729 to Koo et al. (P3) is a pet dental chew with an body containing food, an antibacterial agent, and a calculus remover. U.S. Pat. No. 8,124,156 to Axelrod and Gajria (P4) offers processes for making multi-layered pet treats, and mentions the benefit of an animal chew that massages gums. Dogs like chew toys, but there's little evidence that these work well. They are not veterinary dentistry state-of-art PD control.

BACKGROUND OF THE INVENTION—SOLUTIONS

This invention meets a long-felt, but unsatisfied need of veterinarians and pet owners, for a safe, effective device to prevent dental disease.
1. Specific photodynamic light wavelengths kill canine PD planktonic and biofilm bacteria.
2. These light wavelengths can be generated in, or transferred into, a resilient container.
3. This container can have material and structural means of protection.
4. A replaceable housing, conforming to what dogs like to chew, can surround the container.
5. The housing, which transmits the light, may have photosensitisers.
6. The device can be used independently by pets, with light activated by sensors.
7. Humans can operate it with a switch or wirelessly.
8. Dogs chew on their own toys for over 5 minutes, including the invention.
9. High intensity LEDs can be safely configured to deliver dosage interdentally to destroy PD planktonic and biofilm bacteria.

Some embodiments of this invention use light transmission lines in novel ways. Other industries do this, evidenced by U.S. Pat. No. 9,927,080 to Dahlen et al. (P5) for a consumer display, where light pipes transmit light from source to destination, and U.S. Pat. No. 7,389,020 to Dixon (P6), a light pipe assembly for automobiles, with shock absorbing elements to protect the light pipes.

Veterinarians are currently at risk. This device protects them. Dogs dislike having their teeth brushed. Their front teeth bite and hold prey, long canine teeth tear flesh, molars are sharp for slicing, and big, sharp Carnassial teeth tear meat and crush objects. Brushing puts people's hands in them. If a person follows veterinarian advice, and gets bitten by a dog, veterinarians face liability. A dog owner is a caregiver. Caregivers can successfully sue a doctor who puts them in harm's way, if it can be shown the doctor knew the danger, and the caregiver didn't. The contradiction between veterinarian insistence that dogs be anesthetized prior to professional teeth cleaning, and veterinarian advice to dog owners to brush their dog's teeth, is glaring. The American Veterinary Dental College advice for pet owners, to only seek professional teeth cleaning with anesthesia, warns that anesthesia-free treatment means the teeth cleaner "may be bitten when the patient reacts." (2018, 8) This demonstrates prior awareness. This invention helps solve the veterinarian's dilemma, with a robust alternative to brushing.

Dog owners have anxiety about not doing what veterinarians request them to do, brushing their dog's teeth. This invention can help resolve that anxiety, by enabling them to more adequately eliminate the cause of dog dental disease without putting themselves at risk.

BACKGROUND OF THE INVENTION—QUANTITIES, METRICS, SCALE

Oral microbiologists hypothesize that only a small subset of mouth bacteria species cause dental disease, for humans and other animals. For any treatment to be effective, it must reduce key bacteria by an order of magnitude. Brushing reduces the bacterial load that cause cavities in humans by an order of magnitude (for example, from $10^6$ to $10^5$.)

The goal of this invention is to reduce dog dental disease bacteria concentrations by an order of magnitude, or 1 $\log_{10}$, which can be accomplished with specific light wavelength frequencies delivered with sufficient energy. Kim (2016, 9) found that 405 nm light treatment of *Salmonella*, a Gram-negative bacteria, reduced the bacterial load by 1 $\log_{10}$ at a dose of 144 Joules/cm$^2$, 2 $\log_{10}$ by 288 J/cm$^2$, and 4 $\log_{10}$ by 432 J/cm$^2$. Barneck et. al. (2016, 10) found that 405 nm light treatment of both Gram negative and Gram positive bacterium exposed to light doses of 133±7 J/cm$^2$ reduced bacterial load by 6 $\log_{10}$.

Maclean et. al. (2009, 11) found that 405 nm doses between 42 and 216 J/cm$^2$ reduced hospital bacterial counts 2.6 to 4.7 $\log_{10}$. Little research has been done on periodontal disease causing bacterium, especially as biofilms. According to a review article by Pummer et. al. (2017, 12) on 405 nm light treatment of dental disease bacteria, "inactivation of bacterial species, especially pigmented ones, in planktonic state showed promising results."

Halstead et. al. (2016, 13) reported on a multicenter in vitro study of 400 nm light against both planktonic and biofilm bacteria. The majority of planktonic bacteria had 5 $\log_{10}$ reduction in viability after 54 J/cm$^2$ to 108 J/cm$^2$, which took 15 and 30 minutes, respectively. In biofilms, Gram-negative organisms were more susceptible to 400 nm light than Gram-positive ones. They showed about an order of magnitude reduction in biofilm seeding after 54 J/cm$^2$. The authors believe theirs was the first test of violet light on multiple bacteria in biofilms.

This invention's benchmark is to deliver 50 J/cm$^2$ of 405 nm light to teeth, oral mucosa tissue, gingiva, and adjacent structures in a dog's mouth, in 5 to 10 minutes, to effectively reduce incidence of dog dental disease, by eliminating 1 $\log_{10}$ of bacteria, including those in biofilms.

One watt of power converted to joule per second equals to 1 J/s. Absorbed energy is cumulative. If bacteria absorb ⅙₀ of a Joule each second for 60 seconds, they absorb 1 Joule.

LED manufacturers specify watts of output, which can be translated into Joules. According to the International Commission on Lighting's document on LED measurements 2013 update, the radiant flux of an LED is the intensity where the LED light cone intercepts a 50-mm diameter circle.

Lite-on Technology Corporation's C03 UV Product Series 405 nm high power LEDs emit 1 Watt at 500 mA with forward voltage of 3.7, and at 3.9 fV they emit 1.375 Watt. With a 130° view angle, a light cone intercepts a 50-mm circle at ~11 mm from the diode. Given the inverse square law of diminishing light intensity ($1/d^2$) they deliver 1 J/s at 3.9 fV. At a distance of 22 mm, intensity diminishes to ¼ J/s. Delivering 50 Joules of 405 nm light to surfaces within a dog's mouth, at an average distance of 22 mm from the luminaire, using CO3 Series LED, takes 3 minutes 20 seconds.

Light pipe technology, which uses total internal reflection, does not obey $1/d^2$. It follows Beer's law, in which light attenuates much more slowly, indeed over a distance of 1 or 2 meters, loss is negligible. Connections between light source and light pipe, and bends in light pipes, can decrease intensity by 25% to 35%. The CO3 Series LED light injected into a light pipe, transmitted over 2 meters, may deliver 0.65 Joules, 11 mm distance from the pipe end. At 22 mm distance, intensity is 0.125 J/s. This takes 297 seconds, ~5 minutes, for 50 Joules exposure.

Light pipe technology permits the use of higher powered LEDs, because heat can be managed more effectively if generated outside the dog's mouth. LEDs that need 6-7 fV deliver 5 Watts. If produced 1-2 meters from the animal, these LEDs deliver 3.25 Joules to an illuminating member within its mouth, 0.8 J/s to its mouth surface at 22 mm, and 50 Joules in 1 minute.

Some concern has been raised about the effect of blue light on human, and by extension animal, vision. U.S. Pat. No. 9,439,503 claims ANSI standards, as described in Delori et. al. (2007, 14), prohibit viewing a ¼ W 420 nm LED for more than 0.5 seconds. This is incorrect. Delori et. al., and the ANSI standards, concern collimated (laser) light beams. LED exposure safety is assessed by The International Commission on Non-Ionizing Radiation Protection (ICNIRP) Guidelines.

ICNIRP assessment for a 100 second stare at a distance of 20 cm (7.9 in) is "the blue light effective radiant exposure . . . should not exceed 24 kJ per $1/m^2$." (2013, p. 90, 15) 24,000 Joules exceeds anything an LED can produce. Concerns over blue light are not scientifically valid in ordinary situations. Perhaps misinformed vendors promote false information that frightens people. But consumer acceptance of light devices must account for consumer beliefs, not just facts. The invention described herein uses sensors to turn device lights on only when the device is in the animal's mouth, to reduce eye exposure. That also saves battery power and extends light lifetimes.

DEFINITIONS, TERMS, ELEMENTS

In order to clarify the intent of the present invention and its dissimilar aspects from prior art, a nomenclature system is established.

Used herein "radiation" refers to the deliberate emission of light to achieve some practical effect. Specific light wavelengths refers to electromagnetic radiation of one or several wavelengths within a certain portion of the electromagnetic spectrum between wavelengths of 400 to 700 nanometers (nm), in particular those wavelengths described as antibacterial in research published in scientific journals such as Applied Environmental Microbiology, Journal of Photochemistry and Photobiology, and Journal of Veterinary Medicine.

In the context of this specification and the claims, a "shock absorbing" system has internal component features, and/or method of assembly, that permit it to absorb applied forces and stressors, such as those a dog holding a photodental device might generate, without breaking or being damaged. In extreme cases the system may disassemble, but do so gracefully, to preserve components for further use. It is most likely used with light transmission lines that cannot be separated at a point along their length, in case applied forces exceed a threshold.

A "Generating Unit" is an partially or completely enclosed structure, containing electronic circuits, light sources, and elements that accompany them. Said light sources are arrayed to connect with light transmission lines that extend from the Generating Unit, preferably inside of an umbilical hose. The Generating Unit functions to isolate electronic and light equipment from the forces imposed on objects held inside an animal's mouth. The Generating Unit is positioned at some distance to the animal, and in some embodiments has elements that may fix the Generating Unit to an unmovable position.

"Impervious", as used herein, means a continuous structure integrally formed of a resilient composition that is impact and rupture resistant.

The term "sensor" as used herein generally refers to any measuring, detecting or sensing device, such as stress or strain sensor; pressure sensor; biological sensor; humidity sensor; saliva sensor; displacement sensors; light sensor; darkness sensor; capacitance sensor or other electromagnetic wave sensor.

In the context of this specification and the claims, an "illuminating member" is a container that can be used in accordance with the invention to store light emissions devices, diode emitters, electronic circuits, or receive the ends of optical tubes, pipes, guides or fibers.

In the context of this specification and the claims, a "housing" is the outer cover of a device, that dogs hold in their mouths. Housings can have different attributes. A preferred type have a hard surface over flexible material. In this case, the outer tensile modulus/hardness ratio may have a Shore D hardness of 60 to 120, and the inner layer have a Shore D hardness of 10-60. If it is molded out of more than two layers, the outermost layer may be of lower hardness, such as 40 to 60 Shore D. Materials for housings include, but are not limited to, natural and synthetic rubbers and plastics. Rubber hardness may be modified with quantities of silica and clay. Plastic hardness may be selected by plastic type.

As used herein, "impact resistant structures" are elements with strengthening shapes. "Struts" and "stiffeners" prevent axial deflection of the object they protect. They distribute applied forces around the object. Saddle-shaped "lamellae" are characterized by a negative Gaussian curvature, and improve shape rigidity. A "catenary element" also absorbs impact by flattening over an extended area. "Constant mean curvature surfaces" are areas that resemble the membrane of a soap bubble. They redistribute live load to a theoretically maximum degree. "Minimal surfaces" of similar symmetry and topology, easier to manufacture, improve load absorption to a lesser degree. Various honeycomb "meshes" have side walls that deflect under live load. This shunts impact forces over a wide area.

In the context of this specification and the claims, a "manifold" is made of surface structures that absorb and resist jaw bite and crush forces, in one embodiment including protrusions, or material that is projected from a surface, in shapes such as columnar structures, which are composed of tall narrow cylinders, and between these horizontal cross-braces, a form of support in which two wall-like members intersect or cross each other, to support compression and tension forces. These structures can be made of any material with a sufficient tensile modulus, which may be 1 to 30 MPa, or other moduli. Sufficient strain at break (not brittle) may be 1% to 10%, or other strain. Thicker material provides higher strength, but at increased weight and cost. There is usually an optimal thickness, governed by a strength/weight ratio.

In the context of this specification and the claims, a "tethering system" uses a rope, chain, cord, wire, tie, line, or other linking apparatus, to connect a generating unit and illuminating member, and the tether must at all times be of a length less than or the same as the length of the optical pipes, tubes, guides, and fibers, and their associated umbilical hose, that stretch between a generating unit and an illuminating member. In some embodiments a tethering system is a rod, flexible or rigid, telescopic or one piece, that holds an illuminating member at a fixed or limited distance from a generating unit.

In the context of this specification and the claims, an "umbilical hose" protects light transmission lines and connects light sources in the generating unit with the illuminating member. It's often made of a liner, reinforcement, and cover materials, with stiffness gauged to prevent bending that would damage light transmission lines. It may have a spiral, spring-like structure, made of plastic or metal, attached to the inside cover surface, which may be used in concert with an extending and retracting member, to adapt to externally applied movements.

In the context of this specification and the claims, an "extending and retracting member" is a mechanism that modifies the physical link between a generating unit and illuminating member. It is only necessary that this be a dynamic component that moves along an automated or repeating course to facilitate light transmission.

As used herein, a "suspension arm" and "a bulwark" are structural elements in an illuminating member. A bulwark is a bulge or shaped element attached to, and closely fitting, the side of a container, that serves as a foundation for other structures, such as suspension arms. A suspension arm is a post-like element, held in place by bulwark or other foundation, and on its other end supporting photodental components.

As used herein, a "vacuole" is an empty space within a 3D solid or semi-solid structure inside an illuminating member. A vacuole is typically shaped to house or fit a component, such as a sensor or controller. Its surface may have holes for electronic interconnections that lead between said component to other components in said illuminating member.

In the context of this specification and the claims, "optical pipes, tubes, guides, and fibers" are four categorical names used for light transmission lines that share a common, single structural similarity, being cylindrical in cross-section, linear and generally flexible lengthwise, and share common purpose and use, in channeling light from source to destination. Although all optical fibers, tubes, and guides can be described as light pipes, the term herein is applied to devices that transport non-data forms of light using total internal reflection, with a core transparent material surrounded by another transparent material with a lower refractive index. Light tubes may be molded from a single piece of plastic. Light guides have the same external appearance as pipes or tubes, but contain air, gas, or liquid. Optical fiber are hair-thin strands of glass or plastic surrounded by a lower refractive index plastic, bundled together in a single jacket. All optical pipes, tubes, guides, and fibers are also referred to as light transmission lines.

As used herein, to "inject" light means the process of forcing or directing light emissions into something, such as a light pipe.

In the context of this specification, "lightwave aggregators" are designed, using optical theory, to combine light sources, and homogenize, redirect, concentrate, and inject their light into light transmission lines. Light aggregator shapes alter light ray paths. Oblique edge surfaces steer light beams at angles. Hexagonal cross-sections homogenize light, while shapes tapered along their length concentrate it. Combining two triangular prisms as a surface edge will flip rays to the shape's interior. A flat, angled surface there will redirect the rays if they strike it below their critical angle. Another surface edge, mapped along a curve of critical angles, flips other rays obliquely forward. With six sides and a taper, a lightwave aggregator steers light to a concentrated output.

As used herein, "apertures" are holes that light transmission lines, or light itself, pass through. "Orifices" are holes that electronic and structural components, such as screws, pass through. Both may be of any size.

As used herein, "light pipe fittings" are units that closely fit light emission sources and light transmission lines, to minimize coupling loss. They maximize the amount of light transmitted.

In the context of this specification and the claims, optically accurate radius of curvature concerns a concave mirror surface, whose vertex is the mirror's center. The radius of curvature is a length measured from this vertex into the illuminating member, along the optical axis. The length is the radius of the sphere from which the mirror was cut. Optic accuracy refers to the fact that said radius is also the length from the mirror to the target aperture in the illuminating member. Hence a circle whose center is on the aperture, and whose circumference corresponds to a surface that can accept radiation, contains a concave reflector that can redirect said radiation to the aperture.

In the context of this specification and the claims, fiber optic maximum efficiency includes 8% fresnel loss (reflected light not entering the fiber at the source), 15-17% cladding loss (source light injected into cladding, not core fiber), 9-11% interstitial spacing loss (source light injected into the space between bundled fibers.) Manufacturing imperfections add another 4% to 8% loss of light, leaving a maximum potential transmission efficiency of 60%.

In the context of this specification and the claims, light pipe maximum efficiency includes luminaire-to-light pipe coupling loss that ranges between 1% to 30%, with 8% considered practical if a fitting does not encompass the LED. If a fitting surrounds the LED, as in most embodiments of this invention, loses are 2% to 4%. If LEDs are epoxied to the interior of a fitting, almost no coupling loss occurs, but that probably isn't necessary. Exit losses are 1% to 4%. Manufacturing light pipe tolerances are more generous than fiber optics, so imperfections are less, for maximum potential transmission efficiency of around 90%.

In the context of this specification and the claims, a "luminaire" is a device that is constructed to fit around either diode emitters, or the ends of light transmission lines, for photometric distribution with specific characteristics.

As used herein, "stereotomic design" has a formal quantitative definition. Note first that its architectural definition is "the technique of cutting solids, as stones, to specified forms and dimensions." Its etymology are the Greek roots for solid, stereos, and to cut, tomia. In architecture stereotomy is associated with Gottfried Semper, who used stereotomic to mean a constructive method of assembling mass in such a manner that the total plasticity was molded in one undivided dynamic unity. A formal quantitative definition of stereotomic design follows: an object encompasses three-dimensional space. It can be subdivided into three-dimensional units called cells, each of equal size, that represent the smallest relevant space in a design and/or construction process. Because these are practical units, intended for a macroscopic object, cells are not microscopic. The object's circumference defines its volume; it is filled by the number of cells that can fit such a circumference. Each cell(x) has a value assigned to it to represent the condition of its 4 neighboring cells(n) upon x's removal from the structure, meaning the extent the 4 n's vulnerability to strain and stress increase under tensile, shear, and compressive forces. This can be calculated by finite-element analysis. In the finite-element model, cells are tetrahedral elements with four nodes, made of isotropic, homogeneous, linear elastic materials, and material properties are assigned according to material data sheets. A force is applied to two polar surfaces of the object. Cells are removed, and fine elastic deformation is measured in neighboring cells. A cell with the least impact on neighbors, adjusted for depth in the object, is the first cell for removal. This continues until the object has a chamber. Forces cause relative displacements and deformations among cells. The deformation of a given cell is controlled by $\varphi\alpha(t)$, a tensor.

$$\varphi\alpha(t) = \chi\alpha(t) \cdot F\alpha(t)$$

where $F\alpha$ describes the object's continuum of deformation, i.e. the force condition, and $\chi\alpha$ is the individual cell's rotation and distortion. The next level of stereotomic analysis determines how cell groups can compose optimal void shapes, such as a planar oval shaped void, a spherical shaped void, or an offset cubed void. The compression force generates displacement in any of three dimensions of a cell, represented as $\Delta x$, $\Delta y$, and $\Delta z$ along the X-, Y-, and Z-axis. Shapes are defined as groups of cells in which values of $\Delta x$, $\Delta y$, and $\Delta z$ are the same under a given force. This represents an area that is a center of resistance. Under sufficient compression, any void will collapse to create cracks, which subsequently rotate, elongate, and combine with other cracks. The goal of stereotomic design is to prevent this, with design that increases the critical value of the deformation gradient. Existing analysis includes approximating a solid by a thick walled shell and carrying out an approximate limit analysis of this configuration, by a progressively cavitating void. Equations that determine the response of a void volume fraction to triaxial loads can be used to find optimal void shape. For an axisymmetric void, the maximum supported stress is computed by $$E_e = \frac{2}{3} |E_3 - E_1|$$

where $E_3 = \ln(h/h_0)$, h being the object height, $h_0$ the void height; $E_1 = \ln(R/R_0)$, R being the object radius, $R_0$ the void radius. The results of analysis reveal that two competing dimensions must be optimized: wall thickness as uniform as possible, but with an oblate internal shape. Finally, each cell (x) can be considered a tetrahedron with a stress value given 4 associated cells (n) share faces with (x). These values can be processed using 3rd-order tensors. Each cell has three possible responses to stress vectors, its own, and 2 relative to the row and column it's in. Row and column influences may increase, decrease, or leave unchanged cell (x)'s value. Values are expressed as a vector, the unit's displacement.

SUMMARY OF THE INVENTION

It is a general object of the invention to provide dog oral health devices that use blue/violet light in combination with exogenously applied antibacterial agents to destroy dog dental disease-causing bacteria. In that respect, it is another object of the invention to provide an light emitting source with a light output that is optically transmitted through a housing and delivered directly to a dog's teeth and gums. In one form, the housing is in contact with inner mouth surfaces and the light source is a distance of between 10 mm and 50 mm from them, or between 1 mm and 1000 mm.

It is still another object of the present invention to irradiate a dog's mouth interior with 50 Joules/cm$^2$, or 1 J/cm$^2$ to about 1000 J/cm$^2$, and more preferably in a range of about 10 J/cm$^2$ to about 100 J/cm$^2$, over a 5 to 10 minute period, or a shorter or longer period, or during multiple treatment sessions. The radiation may have an intensity that is substantially constant and monochromatic across the exit aperture in the animal, in particular a dog's, mouth. The radiation may be in a sequence of optical pulses that are directed to various sites on the tissue. Multiple pulses can irradiate multiple sites simultaneously and in sequence.

In one embodiment, the housing held in a dog's mouth is substantially transparent or has windows or holes transparent to the light emissions, or to radiation within at least one wavelength range, so that emitted light passes through the housing without losing substantial light intensity. Preferably an illuminating member within the housing includes protective structures, for example semi-flexible columns and rigid cross-braces, made of resilient materials, to dampen, absorb, and resist dog jaw and teeth forces. In one embodiment light transmitted into, or generated inside of, a resilient illuminating member internal to the protective structures passes through hollow columnar structures, and in some cases a housing that is transparent or with aligned windows or holes, to reach the inside of a dog's mouth.

In one embodiment the invention provides apparatuses, including a housing, an illuminating member, an emitter and electronic circuit. The housing is configured to fit within an animal's, in particular a dog's, mouth, and may be appropriate for canine mastication. The emitter may be in an illuminating member within the housing, or is disposed external to the animal's mouth. For an external light source, optical tubes, pipes, guides or fibers have a proximal end that receives light from the emitting source, and a distal end that outputs the light within an illuminating member, to expose teeth, gum, and tissue in the dog's mouth. The emitter is configured to emit light at wavelengths determined to destroy bacteria that cause gingivitis and periodontal disease in dogs. The light reaches a region associated with animal, in particular dog, dental and interdental mouth tissue, when the housing and illuminating member are disposed within their mouth. The electronic circuit is operatively coupled to the emitter, and is configured to control the emitter when the housing and illuminating member is disposed within the mouth and the apparatus is in use.

The apparatus is useful for eliminating dog dental disease-causing bacteria, in planktonic and biofilm forms, to maintain or improve dog oral health.

In one embodiment the invention further provides methods to increase the therapeutic effect of emitted light by impregnating, coating, or distributing compounds on and in the housing that, in the presence of emitted light, increase the bactericidal effect. The housing is capable of being coupled to an illuminating member that radiates light which passes through the housing. The housing may be replaced without replacing the emitters, electronic circuits, illuminating members, or light delivery systems.

An aspect of the present invention uses housings in accordance with the present invention to distribute compounds in the mouth to amplify radiation impact to synergistically reduce dental bacteria loads. The shape, size, hardness, and color of the housing varies, with different versions configured to conform to different types of dog jaws and teeth, and different dog and dog owner preferences. Compounds in or on the housing can be re-applied once consumed, or the housing may be removed from the illuminating member and replaced.

In one embodiment, the emitter's predetermined wavelengths are selected to reside substantially within the violet-blue spectral region, including 400-500 nanometers, although the range may vary depending upon particular synergistic compounds in the housing, as well as scientific research into monochromatic light therapy.

In one embodiment, the device further includes electrical components for sensing broadband light in the environment of, or sensing applied pressure on the surface of, or sensing saliva on the surface of, a dental device intended for insertion in a dog's mouth, a means for converting the energy, pressure, or biological signal into an electric signal, and a data processor that manipulates the signal to determine to start, continue, or stop emitter radiation.

In one embodiment the present invention comprises a compact, spherical ball-like object which contains one or more emitters and electronic circuits to operate them. The ball-like device is small enough to be held in small dog mouths. The object may have multiple mid-power emitters, or one or more high-power emitters and associated cooling systems. Or it may be connected to an external emitter source. The illuminating member and housing may be fused or undifferentiated.

In some embodiments, the emitter and electronic circuit is contained in a shock-absorbing system apart from the device, isolated from animal forces. For example, an outer ring can absorb forces, moving along a bar that doesn't itself move. Then the emitter and electronic circuit, located on an inner ring that's fixed to the bar, remains protected.

In one embodiment, an illuminating member for light delivery inside a dog's mouth comprises a rigid or semi-rigid, solid or hollow, cylindrical transparent body having a proximal end with a mount for attaching the transparent body to a light transmission system that is connected to an emitter source, the attachment being either inseparable, or having a quick release system that permits the transparent body and mount to separate from the light transmission system. The transparent body extends from a proximal mount and sleeve to a distal end wherein it fits in a support sleeve, and guard rails connect the proximal and distal sides to protect the transparent body. The transparent body is shaped to insert inside a housing that serves as a dog chew object, the housing either substantially transparent to the emitting radiation, or having windows or holes that are transparent. The transparent body is used to reduce the number of oral bacteria.

In another embodiment, the emitters are in a generating unit structure in which they transmit light in light transmission lines that enter millimeter-scale tunnels in small containers themselves inside small housings. Other light transmission lines enter the millimeter-scale tunnel from the distal side, facing the animal. Inside the tunnel, distal light transmission lines slide freely. If animal activity applies extreme forces to light transmission lines, the small containers may be pulled towards the device side, leaving proximal side light transmission lines but unharmed, but the small housings dampen small container movement. Forces may pull the device side transmission lines out of the small container, although they have a structure to dampen such movement. By displacing and offsetting impulse of force, light generating and transmitting equipment will not be damaged by sudden forces. In accordance with the present invention, reducing the strain on transmission lines insures that the device can be used to reduce dental disease causing bacteria, even if the device gets rough treatment by animals, in particular dogs.

The device can include an umbilical hose containing light transmission lines; said umbilical hose comprising a cylinder having a cavity inside, said cylinder comprising a flexible or semi-rigid wall. In one or more embodiments, said cylinder wall is made of a resilient material that may be deformed in such a way that it does not exceed the permissible bending radius of the optical fibers, pipes, tubes, or guides within it. An umbilical hose may also be made of materials that are highly resistant to puncture, or have other properties useful in particular applications.

In a preferred embodiment, the light transmission lines produce total internal reflection, so light intensity does not attenuate over their length. Said light transmission lines may connect to optical elements that light emitters fit into, said optical elements assisting in creating a tight coupling between emitter and transmission line. The light transmission lines may exit an umbilical hose within an illuminating member held in an animal, in particular a dog's, mouth, and at their distal end they may have end caps that act as luminaires whose radiation is absorbed on a dog's mouth interior, to reduce the load of oral bacteria.

In another embodiment, the device further includes a hard, resilient shell, composed of two sides that couple together and contain a liner to which emitters and electronic circuits may be attached. The liner and shell have apertures through which emitters send light. The hard shell is made of materials graded to exceed the jaw and tooth pressure of dogs. The device also includes a housing that surrounds the shell, the housing either substantially transparent to the emitting radiation, or having windows or holes that are transparent, and serving as a chew object for dogs.

In one embodiment, another aspect of the invention resides in a device that may be held by a person for use with a dog, in which the device comprises a handle portion that contains electronic components and emitters, connected to light transmission lines that pass into an illuminating member mounted on the handle portion, said transmission lines having at their distal end caps that act as luminaires, whose radiation is absorbed on a dog's mouth interior; or the handle portion may contain only electronic components, and have electronic lines that pass into an illuminating member mounted on the handle portion, in order to energize emitters within it, that radiate light inside of a dog's mouth. The illuminating member has windows or apertures that light passes through, and is enclosed in a transparent housing, or housing with windows or apertures aligned with the illuminating member's windows or apertures, and the housing serves as an object for dogs to chew. In this aspect of the invention the person may control the operation of emitters, or may let sensors determine their operation. The person may choose to let a dog take the device on their own, as the handle portion may be fit with anti-chew elements to protect it.

In one embodiment, another aspect of the invention resides in a device in which electronic circuits and emitters are housed in a generating unit that may be fixed to the ground or otherwise attached to an object or surface, and an umbilical hose leaves the generating unit through a swivel ball structure, which permits the umbilical hose and associated security tether(s) to freely swivel with respect to the illuminating member they're connected to, held in a dog's mouth.

In one embodiment, a retractable system may be used to control the extent of the umbilical hose and transmission line connection between a generating unit and illuminating member. Its structural features comprise a rotating member mounted on the generating unit, in a housing, the rotating member having a shaft portion extending axially from the generating unit surface, with a circular umbilical hose support surface mounted on it with a retracting nut. The retracting nut compresses a spring member, such as a flat coil spring, which permits the hose and lines to advance axially outward, or retract to be received thereon the support surface.

An extending and retracting member may control the location of an umbilical hose capable of resiliently deforming between a bent/curved state and a straight state, so as to bend and straighten otherwise straight light transmission lines within their tolerances. Any resiliently deformable material, such as a variety of plastic materials may be used, as will be appreciated by those skilled in the art. In one embodiment the deformable outer surface, on its interior side, incorporates a spiraled spring structure of flat plastic or allow wires. The generating unit extending and retracting member serves as a biasing element to cause the spring to extend or retract the deformable surface.

In one embodiment, an animal, in particular a dog mouth's teeth, bone and tissue, are treated by irradiation with a sequence of optical pulses with light wavelengths that destroy dog dental disease-causing bacteria and biofilms directed in sequence to various sites in said dog's mouth. Multiple pulses can irradiate multiple sites simultaneously. During the irradiation sequence, one or more tissue properties may be detected by a sensor. Optical pulses typically pass through the surface of biofilms more effectively than continuous emissions of light energy.

Some embodiments described herein are related to exposing the soft tissue inside dogs mouth to light. Such an apparatus can be used prior to, during, or subsequent to dental veterinary treatment, to increase the rate of healing and reduce the risk of infection.

This summary is provided to introduce a selection of concepts in a simplified form that are further described below in the Detailed Description. This Summary is not necessarily intended to identify key features or essential features of the claimed subject matter, nor is it intended to be used as an aid in determining the scope of the claimed subject matter.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

Exposing the interior of an animal's, especially a dog's mouth, to particular electromagnetic wavelengths in the blue violet region of the visible spectrum, given sufficient intensity and time, can destroy dental disease-causing planktonic and biofilm bacteria in animals, in particular dogs. Unlike a human device, animals cannot be told how to use a device. The device must be tailored to appeal to pets to use, and be of a shape and size they can use. Because pet owners only estimate what their animals can use, and gather animal dental health and disease information sparsely, the device must be tailed to appeal to their assumptions and preferences. Thus, an aim of the present invention is to provide exemplary devices that suit dogs of different sizes and strengths, as well as provide exemplary devices that appeal to pet owners with different beliefs and concerns.

Aspects of the invention are illustrated in the remainder of this disclosure with reference to photodental devices that contain electronic circuits and light sources in the illuminating member and housing held in a dog's mouth, or photodental devices that contain electronic circuits and light sources in a generating unit that is external to a dog's mouth, with light transmission lines that connect the generating unit with the illuminating member and housing held in a dog's mouth. It is understood that the operation of any number of light-emitting oral care instruments for animals, in particular dogs, could likewise be achieved, given the associated advantageous features and effects described herein. These may include use by veterinarians to debride and disinfect their patients, as well as in surgery, and also the use by pet owners in combination with brushing animal teeth.

Figure 1:
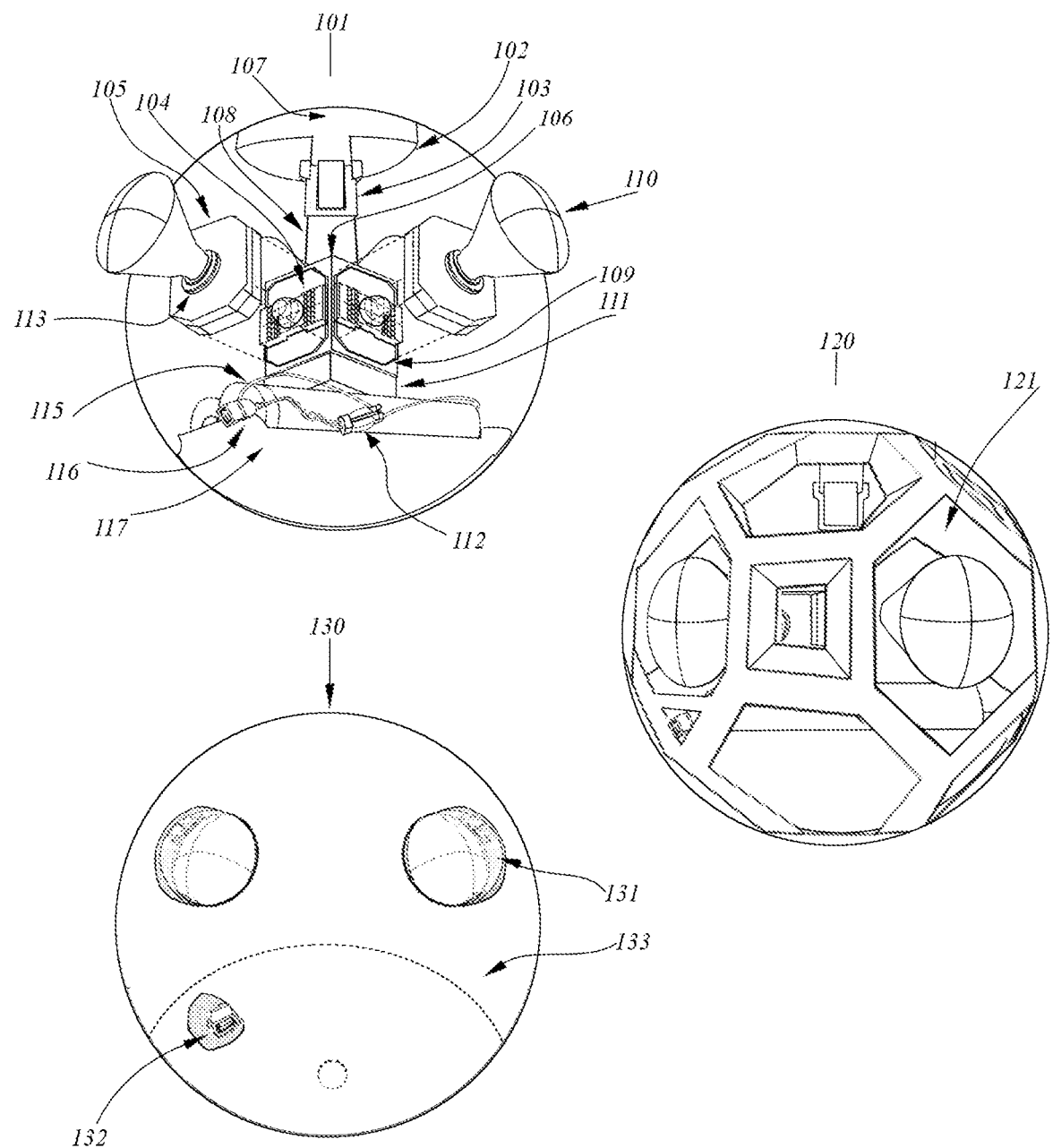
FIG. 1 depicts a representative photodental device for a small dog, illustrating various aspects.

Referring to FIG. 1, illustrations 101, 120, and 130 depict perspective views of a toy sphere, in this embodiment a toy ball for a dog, in different stages of dress. 101 shows the interior of an illuminating member of approximately 5 cm (2 in) diameter, or 4.25 cm (1.67 in) or 6 cm (2.36 in), or any principal axis diameter suitable for a dog to hold in its mouth. 101 is a sphere, as in a ball, or may be a spheroid, or other three-dimensional body. Because of its small size, the illuminating member and housing are fused, and serve as a shell, which is referred to as the housing. The sphere 101 contains multiple mid-power light emitters, in this case four mid-power LEDs. Because LED technology continuously develops, there is no stable industry definition of mid-power using input currents or luminosity. Instead, mid-power LEDs may be defined as efficient heat dissipaters for use in closely spaced arrays and inside small spaces.

Structural component 102 is designed as a cast component, and exhibits at least one suspension arm 108 and a bulwark 107 that abuts the sphere's resilient housing, with which it is joined together as a single piece. Sensor device 103 is attached to suspension arm 108; the arm is load-bearing structural component and is designed according to a load requirement profile to connect to and stabilize device pedestal 106, located near the middle of the sphere. In this embodiment pressure sensor 103 detects flex as the arm unit 102 compresses when held in a dog's mouth, and closes electrical circuits needed for light activation.

In another embodiment, structural component 102 includes two telescopically engaged cylindrical or rectangular members, defining an extendable load bearing member. One member connects to the bulwark, and fits inside a second member with a second end connected to device pedestal 106. Pressure sensor 103 is held in a fixed position on the second member; as the first member slides in and out of the second, the sensor detects motion. When the sphere is squeezed along any axis it causes detectable flexion.

Central pedestal 106 configures multiple mid-energy light emitting devices 104, in one embodiment four LEDs. The pedestal 106 can be solid or hollow, may contain passive or active heatsinks, and its position depends on its attachment to a structural component such as 102. Each LED 104 attaches to a tapered luminaire 110, using mount arrangement 105. The mount includes a sufficiently large housing to support movement in the LED and assembly. The interior of mount 105 has an internal diameter only very slightly greater, or very slightly smaller, than the diameter of an outwardly directed lip 109 or other similar structure which defines an abutment shoulder on the LED 104 surface or a planar face of pedestal 106. The interior of mount 105 can thus be received as a close sliding fit with the surface of LED 104.

As shown in illustration 101, mount 105 has a central bore whose cross-sectional profile provides close-fitting clearance for the longitudinal side edges of luminaire 110. In this embodiment, mount 105 has compression rings 113 which hold luminaire 110 in position. In another embodiment, the luminaire 110 has radially extending elements that extend through the mount 105 housing and may fit into slots on the pedestal 106 surface. It is to be appreciated, however, that the mount 105 could alternatively be configured to have a different cross-sectional profile and luminaire 110 a different attachment method.

A rechargeable battery 115 rests in a chamber in resilient structure 117. The battery chamber is a reservoir which contains terminals for contacting battery electrodes. Coil springs may be inserted in one end of the reservoir, to press against negative terminals. Two batteries may be placed in the chamber, to supply a voltage of approximately 3.6 Volts, although different power source arrangements may be arranged for, utilizing different voltages, power sources, adapters, and/or external power sources. In this embodiment the batteries are rechargeable, for example a nickel metal hydride or a lithium-ion rechargeable battery. Interposed between battery 115 and external power source unit 116 is a charge control circuit 112. In this embodiment the external power source unit is a USB port 116 positioned for user access.

Battery power reaches light emitters 104 through control driver 111. Driver 111 is configured to provide controlled current to the LED array over a range of output voltages, accommodating variation in ambient temperature, moisture, and LED type. The driver may use an oscillator circuit. One transistor measures the current and a second transistor drives LEDs. Output may be divided into two circuit paths, the first to drive serially-connected mid-power LEDs, and the second to supply a holding current. Driver 111 has a footprint of 2 mm×2 mm, or between 1 mm×1 mm and 2 mm×2 mm, or another size appropriate for assembly attachment.

Illustration 120 depicts in perspective a toy sphere such as 101, to show resilient manifold 121 that surrounds and protects interior components, including light pipe luminaires 110. Light pipe luminaires 110 are solid, or not solid, made of materials that resist deformation. Illustration 130 shows the housing accessible to a dog, with polymer apertures 131 for light emission, and orifices 132 for USB recharging. The housing 130 can be separated at 133, for access to inner components.

Manifold 121 is made of resilient compressible material, being either cast with the sphere or fitted into it using hot melt agents, films, waxes, or other adhesives. Manifold 121 may be any formulation of a solution capable of being converted into a flexible, semi rigid or rigid polymer, which itself, or as a composite, alloy, or co-polymer, may be molded, formed, molded or cured.

Illustration 130 depicts in perspective a toy sphere such as 101, displaying outer housing 134 that presents the spheroid to users, such as a dog. Outer housing 134 may be made of a deformable or rigid material that resists puncture or tearing. It contains apertures such as 131 that permit light from light pipe luminaires 110 to emit from the surface, and a recharging orifice 132, in which the recharging connector 116 may be accessed. Outer housing 134 may be separated into top and bottom units, along a meridian such as defined by 133.

The top and bottom housing units may have each a guide surface where they separate, that may be rigid or resilient, that enables either housing part to be separated orthogonal to the meridian axis, or additionally enabling a predetermined amount of flexion, abduction, and or rotation of housing parts.

Figure 2A:
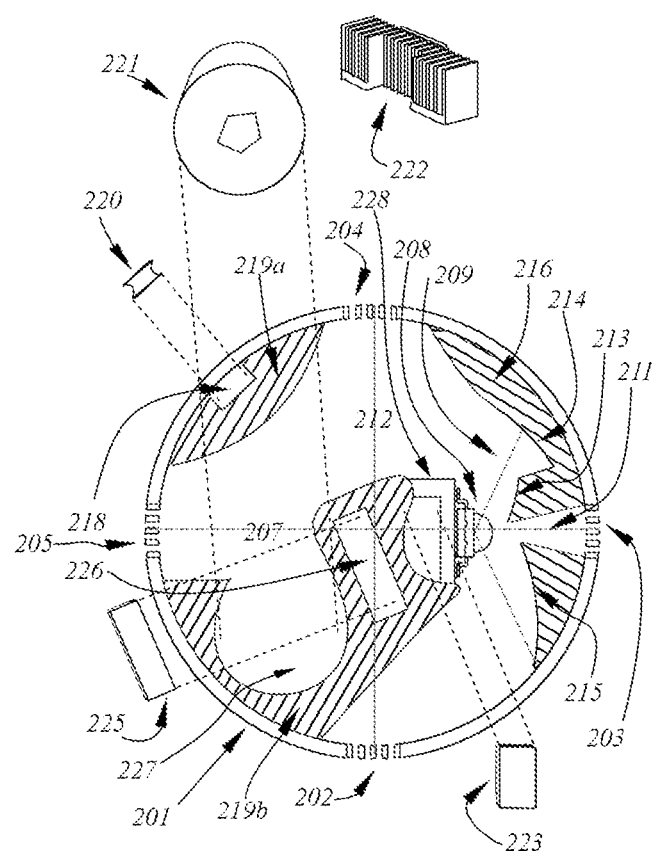
FIG. 2A depicts a photodental device for a small dog with a high-powered light source.

FIG. 2A is a cross-section view of the inside of a spherical toy for a dog, with a high power light emitter, in this embodiment a single high power LED 208. A high power LED is defined as an LED that must be protected from thermal damage, because its operating temperatures will exceed design values for optimal performance. Various heat sinks may be configured to radiate the heat of a high power lighting component disposed within an electronic device into the air via a venting orifice in the device housing.

LED 208 is situated between a central axis 212 and the spheroid housing 201, along the equator 207 thereof. Apertures 203 and 205, on housing 201 at apical points on the equator 207, and apertures 202 and 204, perpendicular to these on housing 201 at apical points on the central axis 212, permit light transit.

A resilient structure 219b is attached to the bottom of the sphere, and contains a vacuole 227 defining a chamber which contains battery 221. Vacuole 226 in resilient structure 219b, between vacuole 227 and LED pedestal 228, defines a chamber to contain LED driver 225. Battery 221 and LED driver 225 are held in place by close fit, attachment straps, or other harness. Power lines thread through resilient structure 219b from the battery 221 to the LED driver 225 and to LED 208. LED pedestal 228 is held in place on resilient structure 219b with screws, adhesives, or other clamping method, and supports LED 208 held on its surface using similar techniques. The high power LED has a predetermined wavelength frequency output.

In this embodiment, LED 208 has a 130 degree output angle of dispersion, shown by 209. Light within approximately 10 degrees of equator 207 transmits directly through open space 211 and aperture 203. Above open space 211 the housing 201 supports integral inwardly projecting structure 216, and below open space 211 housing 201 supports integral inwardly projecting structure 215. The upper structure 216 has a two different convex faces, 213 and 214, which have optically accurate radius of curvature such that radiation incident on the concave reflective surface is directed to travel some distance through the interior of the sphere to an aperture on its surface. Convex face 213 is coated with, or has attached, a reflective surface that receives radiation reaching 10 to 40 degrees above equator 207 and directs it through top aperture 204. Convex face 214 has a reflective surface that receives radiation reaching 40 to 65 degrees above equator 207 and directs it through aperture 205 at the opposite end of equator 207.

Lower inwardly projecting structure 215 has a reflective face shape with optically accurate configuration such that it receives radiation reaching 10 to 65 degrees below the equator 207 and redirects it through bottom aperture 202. Thus LED 208 light is transmitted through four apertures 90 degrees apart.

A heat sink 222 works to disperse LED heat through opposite sides of the sphere. It fits, as component 223, behind the LED pedestal 228, with heat sink extensions that reach both sides of the sphere. The pedestal 228 can be a solid body, cylindrical, square, rectangular, or any shape that can be mounted with high power LEDs, and be proximate to heat sink arrays. The heat sink 222 can include thermal transport materials and mediums to enhance heat dissipation. Sensor 220 fits in vacuole 218 next to the sphere surface in resilient structure 219a. The sensor detects compression or darkness, and signals controller 225 to switch light on.

Figure 2B:
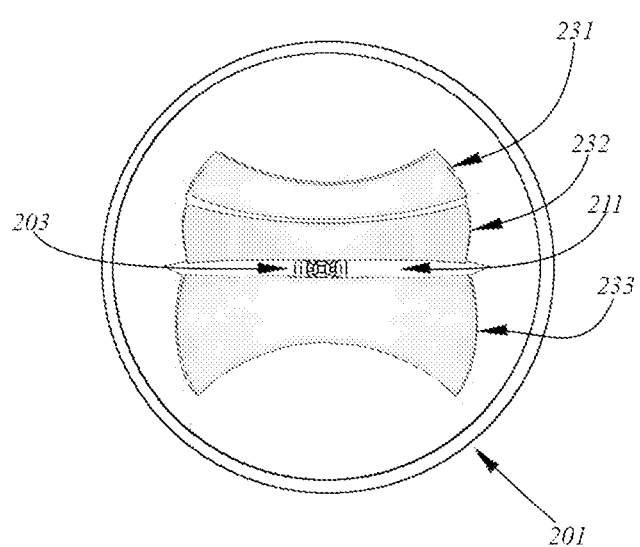
FIG. 2B is a cross-sectional view of the embodiment shown in FIG. 2A.

FIG. 2B is a cross-sectional view of the same spherical toy for a dog as FIG. 2B, displaying the reflective surfaces in face view, to show the layout of that portion of the sphere interior. Upper reflective surface 231, which is attached to face 214, reflects light across the sphere to the opposite side. Upper reflective surface 232, attached to face 215, reflects light through the top of the sphere. Lower reflective surface 233, attached to face 215, reflects light through the bottom of the sphere. Light also passes through 203, directly in front of the LED, visible through empty space 211, between upper and lower reflective surfaces. All internal structures must ultimately be attached to housing 201.

Figure 2C:
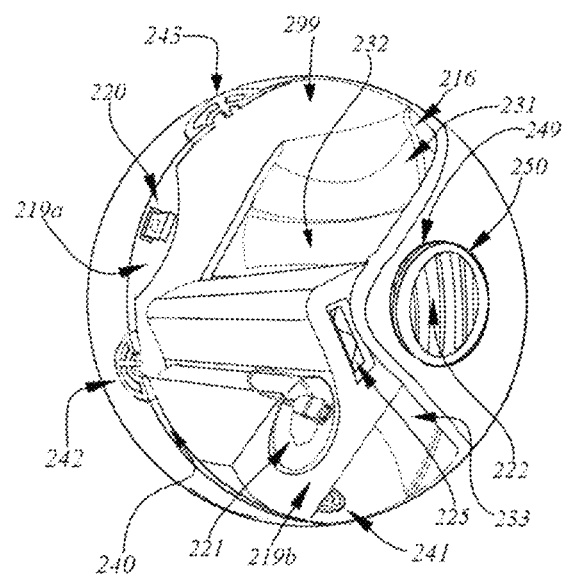
FIG. 2C is a cut-away view of the embodiment shown in FIG. 2A.

FIG. 2C is a cut-away perspective view of the illuminating member 299 of a spherical toy for a dog, which contains a high power light emitter, and mirrored surfaces to reflect emitted light through apertures on the spheroid housing 240. Resilient structure 216 supports reflective surfaces 231, 232, and 233. Three apertures are visible, 241, 242, and 243, composed of transparent material, such that device emitted light is directed to external areas outside of the spheroid. Resilient structure 219b supports battery 221 and LED driver 225, fitted in vacuoles. Sensor 220 fits into resilient structure 219a vacuole. Heat sink 222 is visible where one side of it ends, at the spheroid surface behind protective barrier 250.

Heat sink 222 has an axis perpendicular to its position vis-a-vis the LED, having an array of extending fin structures being at one end thermally coupled to the LED pedestal, and at the other end thermally proximate to a hole 249 in the spheroid illuminating member wall 240 such that heat is transmitted from the interior to the external environment through hole 249. A protective cap 250 that fits into hole 249 is positioned over the end of the heat sink 222.

Figure 2D:
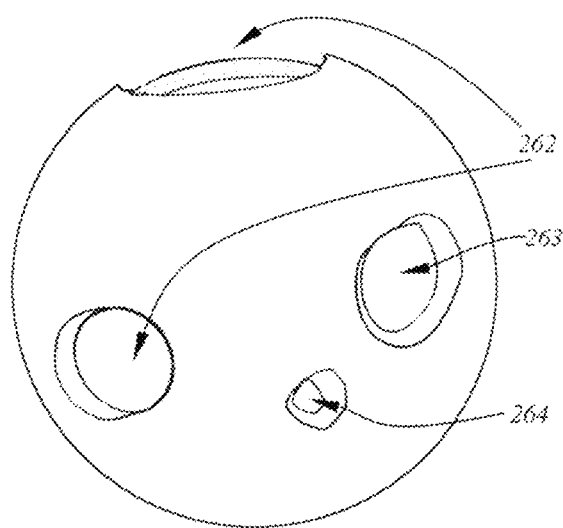
FIG. 2D is an external view of the embodiment shown in FIG. 2A.

FIG. 2D is a perspective illustration of the external environment-facing housing of a spherical toy for a dog, with apertures 262 open to light emitting apertures on the spheroid surface. Orifice 263 is open to thermal transport, and orifice 264 is open to a battery recharging component.

Figure 3A:
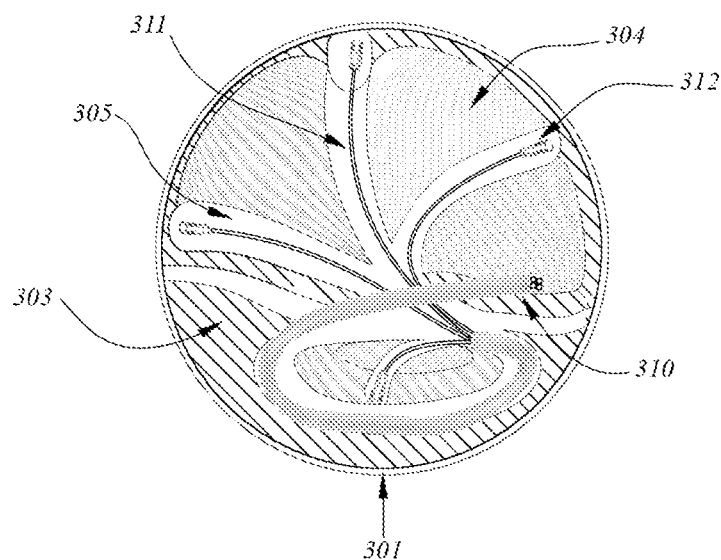
FIG. 3A is a cut-away view of photodental device for a small dog with transmission lines.

FIG. 3A is a cutaway view of a photodental device for a dog, shaped as a spheroid, that contains optical pipes, tubes, guides or fibers that transmit externally produced light into, through, and out of the spheroid. The spheroid contains no electronic device elements that require electric power. This makes it inherently safe for animals that have powerful jaws and teeth from injury caused by damaging light producing components.

A flexible light transmission line assembly is illustrated inside illuminating member 301. An umbilical hose 310 that is in connection with external (not visible) light producing elements can be connected to light transmission lines 311 inside the spheroid without having to make splices, if light transmission lines in the umbilical hose are used in the spheroid's assembly, positioned in open channels such as 305 inside the spheroid. Structural support materials fills the rest of the spheroid.

Two kinds of structural materials are present. An exterior region is formed of rigid, resilient material 303, such as an acrylic. It may be molded in place of housing 301, or fit within it. Light transmission line channels 305 have an external periphery defined by a layer of a more deformable material 304, which bounds, in part or whole, to the interior surface of the rigid material 303. Rigid layer 303 can be molded separately and then filled at least in part with more deformable material 304, in which light pipe channels are inserted prior to cure. Elastomeric material in liquid phase can be displaced, compressed, and expanded without causing distortion when hardened. Alternately, a mold may be formed with internal light transmission line channels, in which an elastomeric substance 304 is formed into a shape. The exterior rigid layer 303 can then be slid onto the elastomeric molded interior. Either way, the sphere is largely solid with channels.

Light pipe fittings 312 serve as luminaires to direct transmitted light through apertures into the immediate external environment.

Figure 3B:
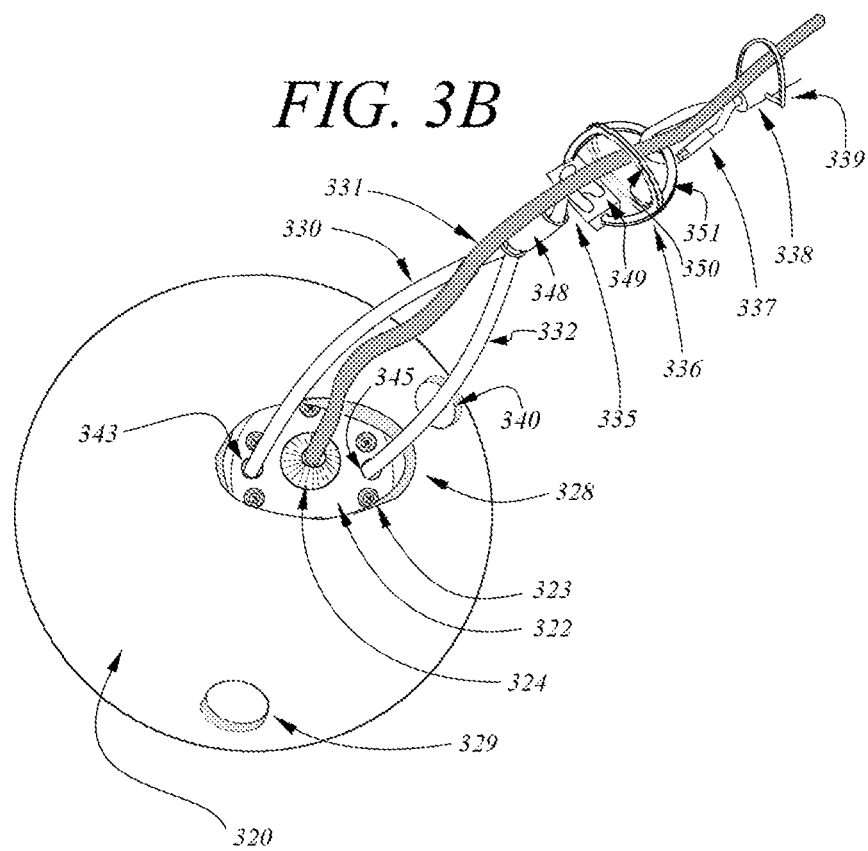
FIG. 3B is a perspective view of the embodiment illustrated in FIG. 3A.

FIG. 3B is a perspective view of the photodental device illustrated in FIG. 3A, showing the spheroid with a cover member 320 which conforms to its shape and aperture locations, such that the cover has holes such as 329 and 340 that align with the spheroid apertures. The cover member 320 may be put in place by any one of a wide range of mateable or engageable fittings, such as male and female joints, as would be obvious to one having ordinary skill in the art after having become familiar with the teaching of the present invention.

Cover member 320 contains hole 328 which reveals an attachment plate 322 positioned on the spheroid housing with screws 323. Plate 322 has a central axial passage 324 to allow an umbilical hose 331 to enter the spheroid. Passage 324 may be configured in size to be similar to the exterior configuration of umbilical hose 331 so the cable fits snugly into the passage with little or no play between them. The passage 324 may have a plurality of resilient flanges such that the internal diameter of the assembled flanges is less than the external diameter of the feeder cable.

As seen in FIG. 3B, plate 322 has two fastener receptacles, 343 and 345, through which tether cords 330 and 332 are inserted and anchored in the spheroid. The receptacles are positioned so that the inserted cords enter a fastener attached to the rear surface of the plate. Tether cords 330 and 332 extend a short distance out from the sphere, as illustrated, where they are compressed in a collar 348, then thread as shown by 335 through anchor block 349.

Anchor block 349 is held on a ring 336, which has two components, a ring 351 which runs through anchor block 349 and holds it, and perpendicular to that a ring 350 through which umbilical hose 331 passes. Ring 336 is attached to tether cable 338 with a carabiner 337 or similar fastener. Rigid stirrup-like components 339 are inserted periodically in tether cable 338. Umbilical hose 331 passes through stirrup-like components 339, to remain proximate to the cable which tethers the spheroid device to the light generating system.

Figure 4:
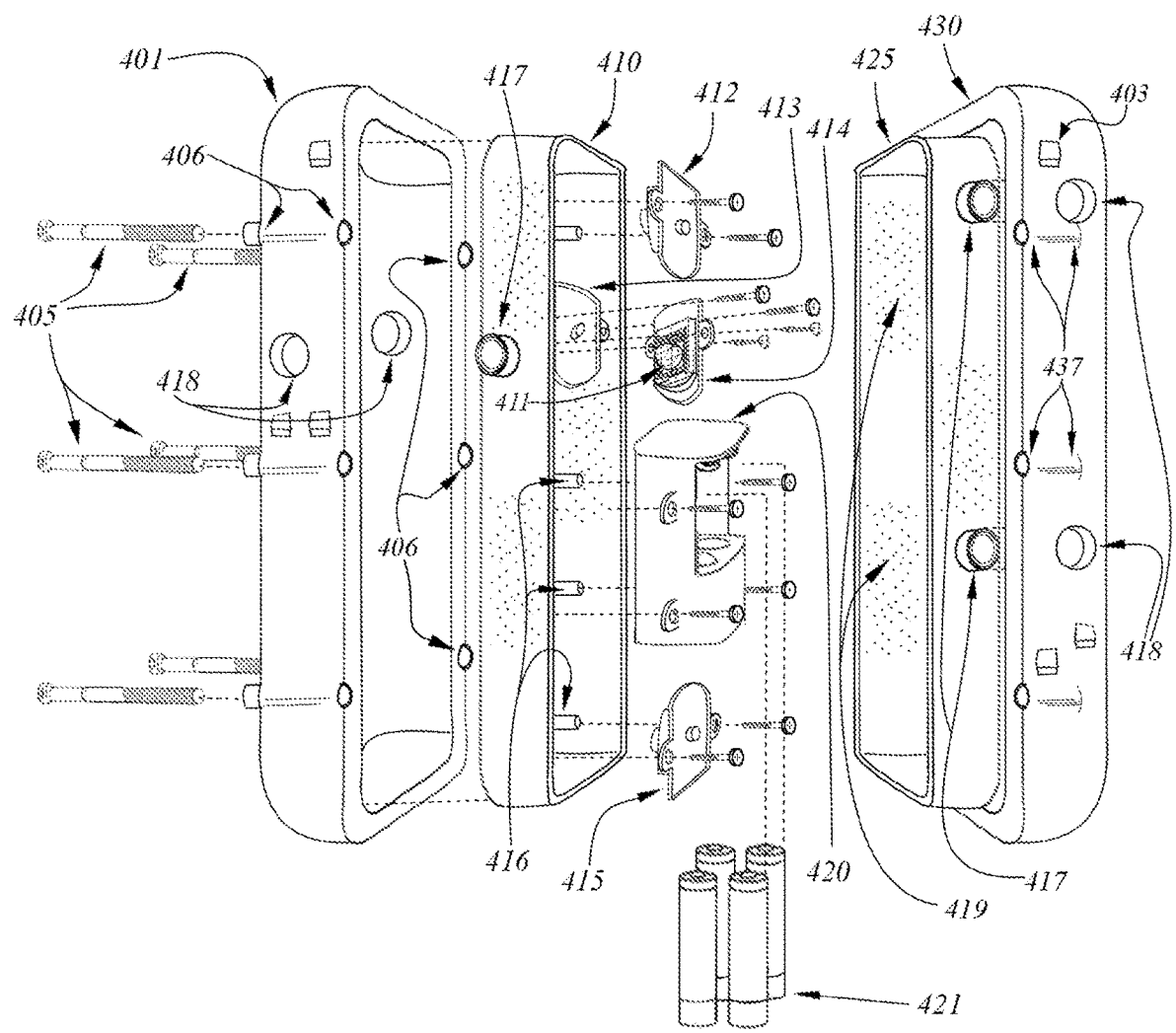
FIG. 4 is a exploded view of a hardened casing photodental device.

FIG. 4 is an exploded perspective illustration of a hardened impervious encasement photodental device to be inserted into an object that a dog or other animal can hold in its mouth. The invention includes two halves, 401 and 430, of an impervious illuminating member that fit together to define a cavity, with a liner in two halves, 410 and 425, located between the illuminating member and the open cavity in a close fit. Electronic elements, including light emitting devices, 412-415, are secured within the cavity to the liner. Light emitting domes such as 411 protrude into open apertures 417 in the liner 410 and apertures 418 in illuminating member 401, such that light is transmitted outside. A light emitting device such as 415, preferably an LED, mounted on a base, is attached with screws into an internal liner 410 through mounting holes 416.

In this embodiment, LEDs such as 415 and 412 face directly towards the middle vertical axis of the liner, and LEDs such as 413 and 414 are attached at an angle adjacent to the middle vertical axis. This permits a more complete light emitting field. Batteries 421 fit into a battery holder 420 which screws into mounting holes 416.

Internal liners 410 and 425 form two halves which join together, tightly aligned by the impervious illuminating member. Liners may be composed of shock absorbing material and also may be air permeable. In some embodiments the liners may be held together by fixing pins. Liner material such as a high molecular mass polyester may provide high hardness, tensile and flexural strength; any material suitable for being shaped, formed, or fitted as described may be used. Holes such as 419 in the liner permit air to pass. The impervious illuminating member formed by joining 401 and 430 may be made of hard metals, hard-wearing ceramics, or elastomeric material. A seal may be provided between the edges of liners and illuminating member to prevent abrasion.

In this embodiment impervious illuminating member half 401 includes six screw or bolt-receiving mounting flanges 406 on two sides, and impervious illuminating member half 430 includes six screw or bolt-receiving mounting flanges 437 on two sides. The flanges receive fixing bolts 405 which secure impervious illuminating member half 401 to impervious illuminating member half 430. Also visible are guide tabs 403, used for fixing an outer housing to the impervious illuminating member.

Figure 5A:
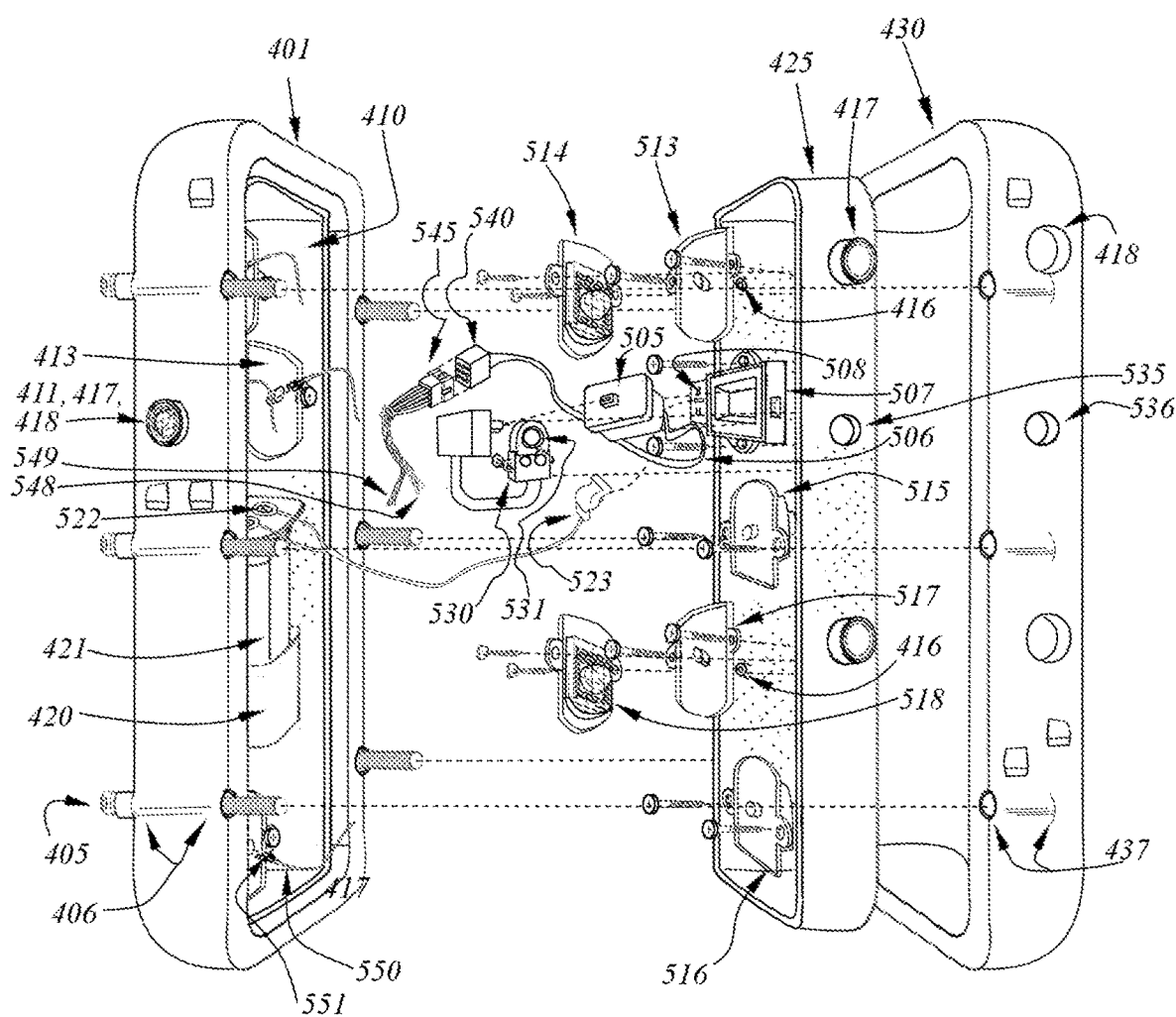
FIG. 5A is a complementary side view of the embodiment shown in FIG. 4.

FIG. 5A displays the complementary side details to the details in FIG. 4, of the impervious illuminating member photodental device. Liner 410 is shown in a fitted position in the particular embodiment. Liner 410 includes LEDs such as 413 screwed into place, and battery holder 420 installed with batteries 421 inserted. Light emitting dome 411 protrudes into liner aperture 417 and impervious illuminating member aperture 418. Liner 425 includes six LEDs 513-518, which are fixed to the liner by means of screws into mounting holes such as 416. Four LEDs, 513, 514, 517, and 518, are positioned on liner 425 at an angle facing to the side, and two LEDs, 515 and 516, face the vertical axis at liner 425's center. Each LED dome fits into a liner aperture such as 417, which inserts into a impervious illuminating member aperture such as 418.

Battery holder 420 has two electronic connectors 522 for electric connection with switch unit 507. This is achieved with power plug 523, which inserts into female plug 508, attached to switch unit 507. Sensor 530 detects darkness/light, or other environmental attributes; its detector element 531 fits into liner aperture 535 and impervious illuminating member aperture 536. The base of sensor 530 has contact elements such as electrodes integrally molded to form a tip that plugs into controller pad 505 which is embedded in switch unit 507 that is fixed to liner 425. Flexible circuit cable 506 threads out of unit 507, ending in circuit electrode array 540, that is attached to the lighting electronics array 545. The array of electronic lines is divided into two groups after the attachment point of 540 and 545, array group 548 which powers LEDs 513 to 518 on liner 425, and array group 549 which powers LEDs 412 to 415 on liner 410. Each electronic cable in an array group, such as cable 550, attaches to an LED with plugs, such as 551.

The operation of the LEDs 412-415 and 513-518 is through controller pad 505 and switch unit 507. The switch unit 507 opens or closes an electronic path depending on the state of sensor 530. In this embodiment, when the sensor detects less external light than a given value $k_1$, the controller pad 508 turns on switch unit 507 to close the electronic circuit to the electrode array 540 to charge the assembled power cables groups 548 and 549 that power LEDs. When sensor 530 detects external light levels equal to or greater than given value $k_2$ the controller pad 508 turns off switch unit 507 which opens the electronic circuit to electrode array 540.

In a further embodiment, which is however not shown, an external override switch can be used to turn the device lights on and off. From the illustrations it may be plainly visualized that liners 410 and 425 are held together by the impervious illuminating members 401 and 430, which are sized to fit tightly. Each of the two impervious illuminating member segments have mating edges, and when coupled together the mating edges are held together by screws or bolts such as 405, which fit into bolt holes such as 406 and 437 adapted to receive the bolts on both impervious illuminating members.

Figure 5B:
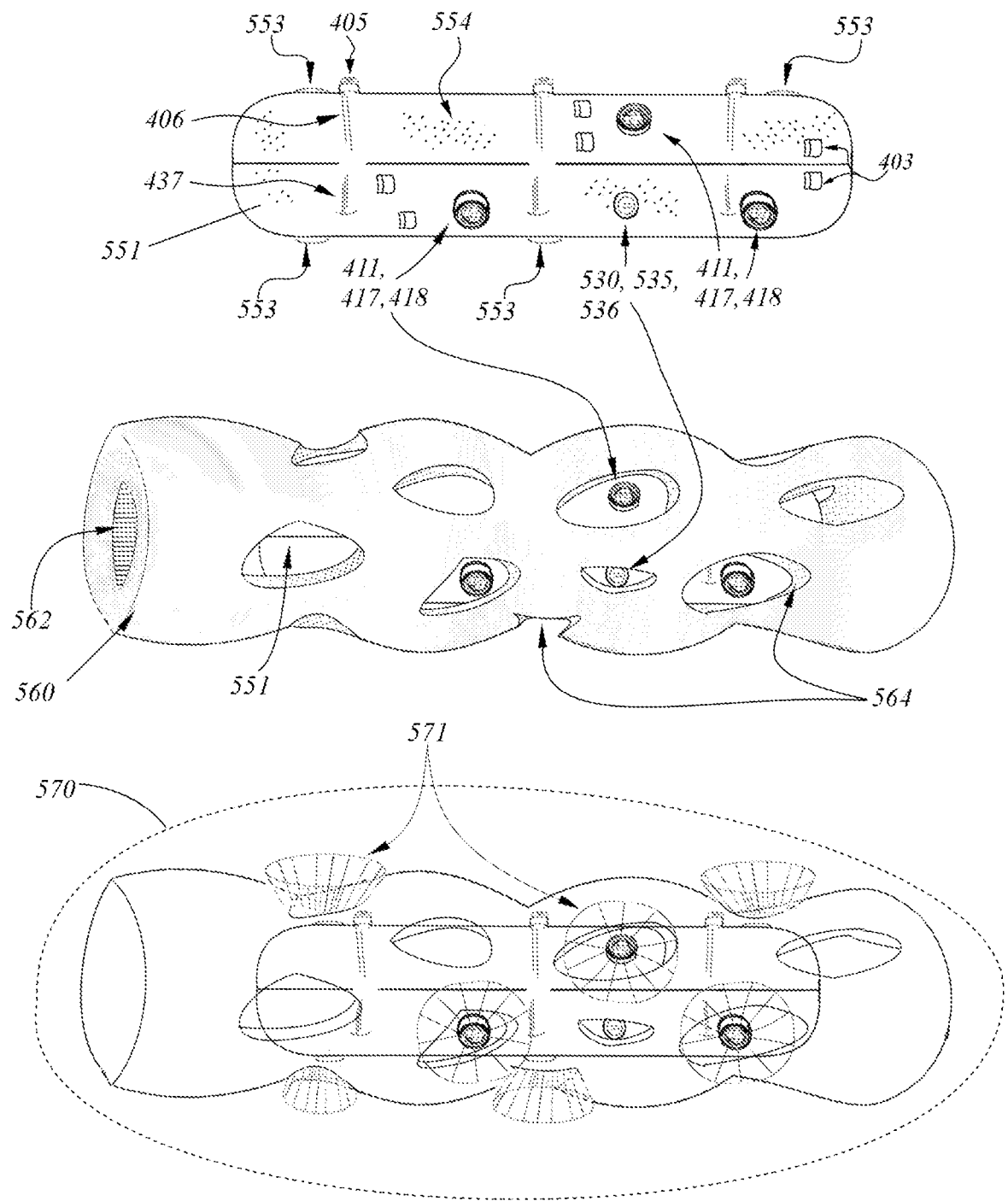
FIG. 5B is a perspective view of the embodiment shown in FIG. 4.

FIG. 5B displays a perspective view of an impervious illuminating member embodiment. A impervious illuminating member 551 contains the electrical and electronic components of the device, such as power supply, controller, light emitters, and interconnections (FIG. 4 and FIG. 5A). LED dome 411, liner aperture 417, and impervious illuminating member aperture 418, align in close fit. The impervious illuminating member edge shows the flange lip of apertures 553. These protect the LED dome inside from outside contact.

Bolt holes 406 and 437 receive bolt 405 that close the impervious illuminating member 551 in a practically sealed condition. In the shown embodiment impervious illuminating member 551 is manufactured from metal. To ventilate the mid-power LEDs, small holes 554 are distributed in it. Impervious illuminating member 551 is covered on the outside with a pressure and tear resistant housing 560. The housing is formed to appeal to animals such as dogs. Housing 560 has an end opening 562, through which impervious illuminating member 551 is inserted. Openings 564 in the housing are aligned with light emitters, liner, and illuminating member apertures 411, 417, and 418 and sensor, liner and illuminating member orifices 530, 535, and 536. Alignments are maintained with protruding elements on the housing's interior (not visible) which engage guide slots such as 403.

Illustration 570 displays the photodental device with light emissions traced from LED light sources or array disclosed in FIGS. 4, 5A, and 5B above. The critical light cones 571 emitted by the invention are drawn as they emerge from the device surface guided by liner, illuminating member, and housing aperture alignments. This produces concentrated light distributed across the inside of an animal's, such as a dog's, mouth. The distance between luminaire and mouth surface will be within 5 to 50 mm, close enough so bactericidal wavelengths will impact dental disease bacteria sufficiently to reduce their load by an order of magnitude, if the device is held in the mouth for >5 minutes.

Figure 6A:
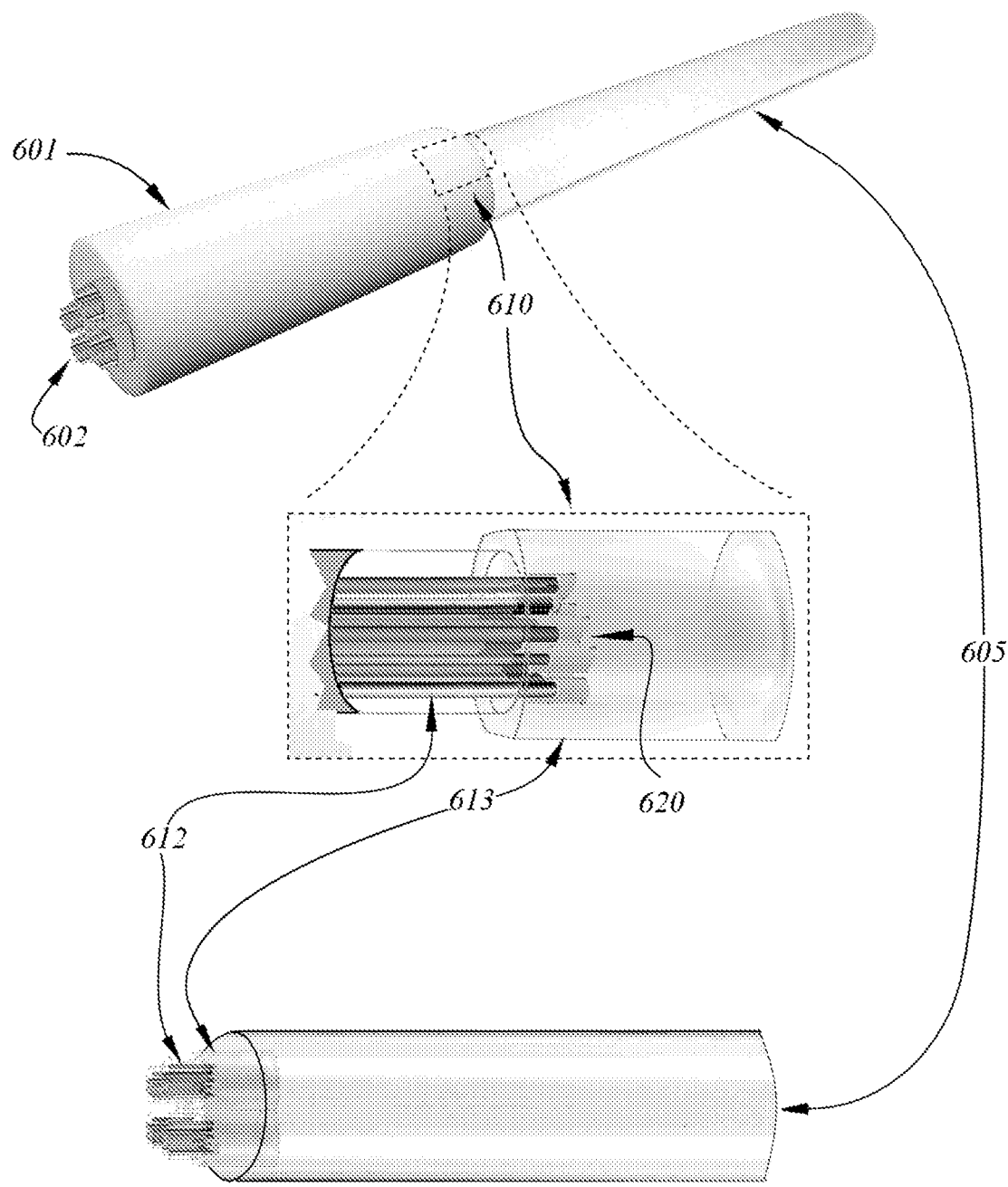
FIG. 6A is a side view of a light wand photodental device for a dog.

FIG. 6A shows a side view of the light wand and it's basic construction and space. The area 601 at the end of the wand is sufficient to ensure that light transmission lines, in this embodiment fiber optic lines 602, are provided with stability and isolated from the environment. The illuminating member 605 is a transparent material in which light exists from the fiber optical lines, and passes into the external environment.

The area 610 is blown-up to show how individual optic fibers 612 exit their standard jacket and have tip ends embedded in coreless endcaps 620. If that index is lower than the optic fiber's, the coreless endcaps reduce optical feedback that can damage fiber. The coreless endcaps 620 are further embedded as a group in a transparent plug 613, made of transparent material, in this embodiment with a lower refractive index. Plugs 613 are further embedded in the transparent illuminating member light wand 605. Plug 613 is shaped shape to ensure light beams move towards the external environment. The light is spread out along the wand's length.

Figure 6B:
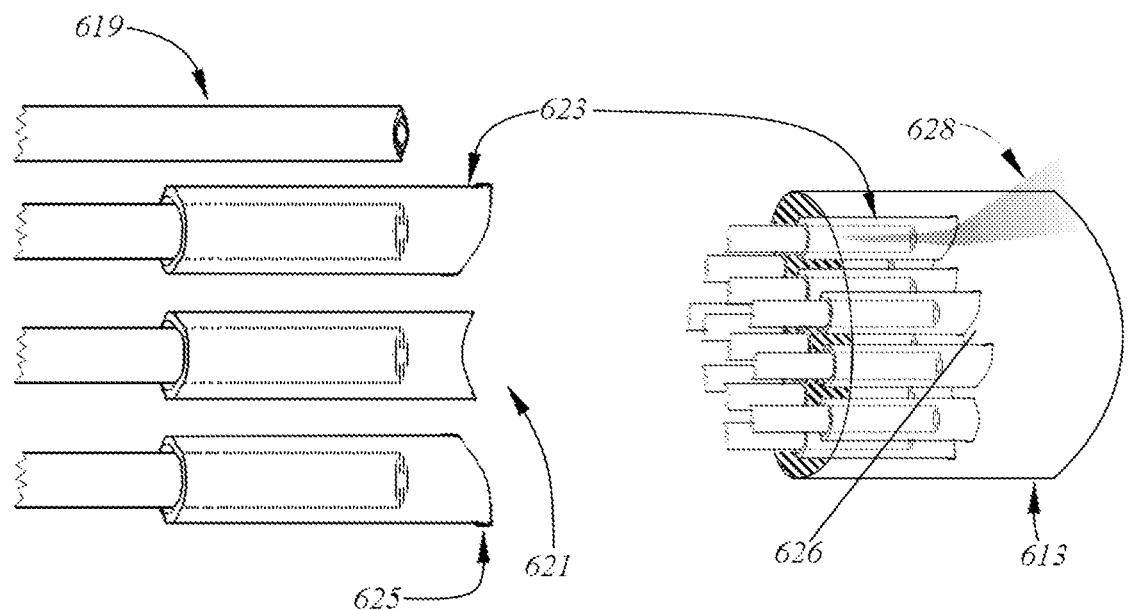
FIG. 6B is a perspective view showing details of the embodiment in FIG. 6A.

FIG. 6B illustrates details of individual light fibers such as 619 embedded in transparent endcaps, polished to an angle that modifies the direction of the output beam. The angle of the endcap end acts like a modified prism, rotating the light beam. Endcap 623 polished angle rotates the beam upwards, endcap shape 621 disperses the beam, and endcap 625 polished angle rotates the beam downward. The polish angles are exaggerated for clarity. Illustration 626 displays the fiber endcaps as embedded in transparent plug 613, with a free-space output beam 628 shown, the angle of the endcap polish surface and the output beam both exaggerated for clarity.

Figure 6C:
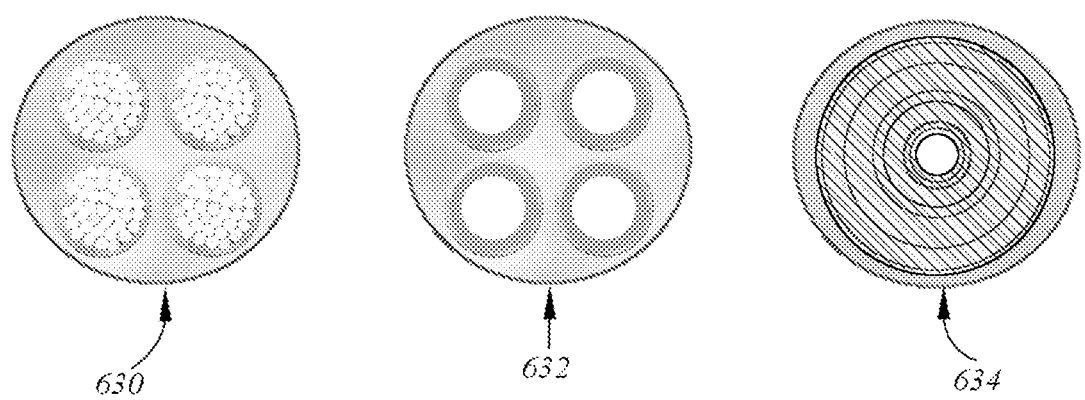
FIG. 6C is a schematic view of alternative components in the embodiment in FIG. 6A.

FIG. 6C illustrates three categories of light transport mechanisms, that can be used in different embodiments of this invention. 630 shows optic fiber bundles, each fiber a core with cladding, coated, bundled in groups, groups sheathed in material graded for particular use. Optic fibers have a maximum efficiency of about 60%, and lose around 2.4% transmission per foot. Given a continuous input of light for 10 minutes, optic fibers can sustain light sources of 50 mW. Over 6 feet, 51% of source light may emit at the end. Quartz fibers may provide maximum transmission efficiency for violet wavelengths. Fiber optic encasement are not adapted to a quick-disconnect mechanism in the user environment. Optic fibers must be run in an outer housing that restricts bending to the fiber's permitted bend radius, which may require metal jackets.

632 shows light pipes, each with a core and cladding, coated, grouped, and jacketed. Conceptually similar to optic fibers, light pipes have much larger diameters. They are less expensive that optic fibers, more rugged, and produce fewer nonlinearities, so better at single-frequency light delivery. However when bent at sharp angles, large diameter flexible light pipes are less efficient than a similarly sized bundle of fibers. Light pipes transmit more light than an equivalent sized bundle of optic fibers. This is because the transmission function scales with the transmission line's core diameter squared, so enlarging diameters linearly increases light transmission exponentially. Given continuous transmission over 10 minutes, a 5 or 10 W light source can be used. Light pipes have a maximum efficiency of 90%, and lose around 8% per foot. Over 6 feet, 48% of source light may emit at the end. Because light-pipe coupling tolerates disconnections, they may be adapted to a quick-disconnect mechanism in the user environment.

634 shows a liquid light guide, typically a transparent, anaerobic non-toxic liquid core in a tube made of flexible plastic with an index of refraction which is lower than the liquid medium, to induce internal reflection from within the liquid core. The plastic tube is in a flexible metallic hose, which may have several layers, covered by a PVC jacket. Liquid light guides bend well and do not fatigue and break. They lose almost no intensity over distances, and with ends sealed by polished fused silica glass, coupling losses are 2% to 4%. At 6 feet, 95% of source light may emit at the end.

Figure 6D:
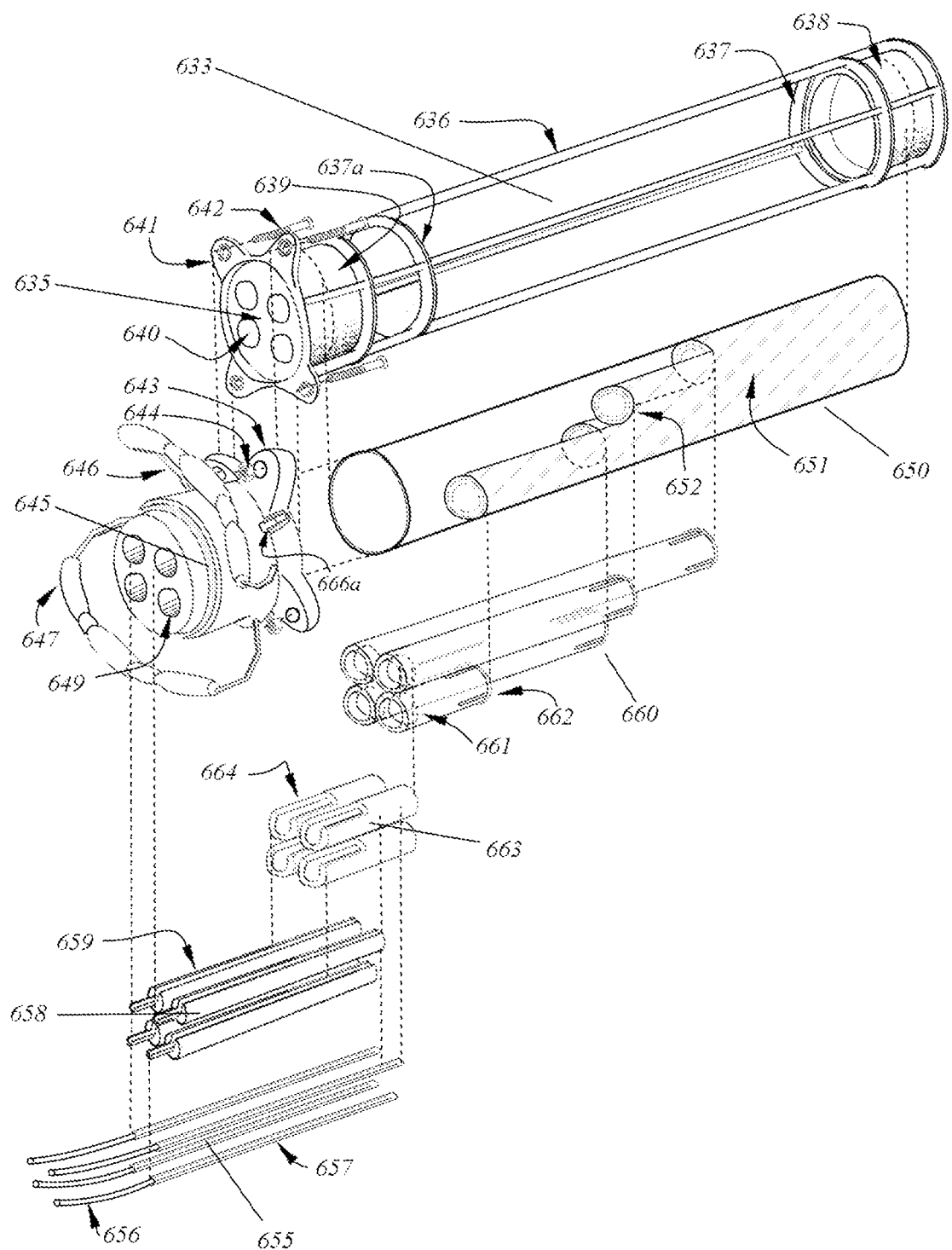
FIG. 6D is an exploded view of a release mechanism in the embodiment in FIG. 6A.

FIG. 6D is an exploded drawing of a photodental wand device, configured with a quick disconnect component. Wand 633 includes frame members 636 which run longitudinally along the wand, which mechanically strengthen the wand and gives form to the housing that goes around it. Near the distal end of the wand 633, ring 637 is attached to frame members 636, and near the proximal end of the wand 633, ring 637a is attached to frame members 636, both rings with central axis transverse to frame member 633 linear axis.

There are various ways of implementing this section of the device, each of which has advantages adapted for use in different possible technical combinations. For example, longitudinal and ring segments of the frame form a cavity to position the illuminating tube. Either the frame ends or the frame sides may open to permit the tube's insertion and removal. Frame segments may be separated and the illuminating tube placed within them, and frame segments may then be clamped in place, with, for example, pins, screws, or bolts, and/or frame segments may be hinged, sectioned, and held in position with fasteners to permit the illuminating tube to be received in the frame.

A stabilizing baffle 638 is placed at the distal end, and a stabilizing baffle 639 is placed at the proximal end, in the longitudinal direction of the wand. Baffles 638 and 639 provide stability for the frame and a structure for illuminating tube 650 to fit into. At the proximal end of this embodiment, frame 633 is connected to neighboring receptacle 645 through plate 635, which may be made as a single unit structure with the frame members.

Plate 635 is characterized by through-holes 640 for light transmission lines to fit in, and elements such as 641 that serve as flanges for screw or bolts 642 to fit through, to attach plate 635 to receptacle 645. Receptacle 645 is a quick disconnect assembly, including screw or bolt holders 643 that fit screw or bolts 642 and nut 644 to fix them in place. Locking fastener 646 extends upward from receptacle 645, and fastener 647 extends downward, in the orientation shown in the figures. The locking fasteners 646 and 647 mate circumferentially around a fixed flange (FIG. 6E 666), and transfer motion to it. The cross-sectional shape of receptacle 645 is typically a circle, oval or octagon, measuring between approximately 12 mm (0.47") to 35 mm (1.38") in diameter. The locking fasteners 646 and 647 should be large enough to hold fixed flange 666 firmly, with an offset distance of about 3 mm (0.12") to 15 mm (0.59") beyond the edge of flange 666. Simultaneously, a tightening member 666a may be used to adjust fasteners 646 and 647 so that excessive force applied to the wand may cause their disconnection.

It will be understood that a quick disconnect coupler assembly, such as 646, 647, and 666, permits attachment with as few tools as possible. A large benefit is achieved if wand 633 is disconnected from other components when an animal, such as a dog, excessively pulls, shakes, and/or rotates the wand in such a way as to threaten electronic connection integrity. The owner can quickly reattach the wand to the rest of the device without any tools by hand grasping and squeezing the locking fasteners 646 and 647 and sliding them around 666.

Other embodiments may use other quick disconnect structures to accomplish the mating of a light wand and other structures. The two bodies represented by the two parts of the divided mount can be held together by a frangible sleeve and pins. If forces drive the sleeve and/or pins to fracture, the bodies separate. This requires a new sleeve and pins to put the two sides together. Another embodiment can use elements such as compression springs pressing against each other, and/or magnets attracted to each other, to maintain contact during normal operation, but separable when undergoing sufficient stress. More embodiments may be discerned by others familiar with the art.

Segment 645 contains through-holes 649 that align with through-holes 640, as can be seen in an exploded perspective. Light transmission lines, such as 656, are placed into these through-holes, with an assembly that includes: segment 655 that holds light transmission lines 656 in thin tubes 657; segment 658 which retains segment 655 in a funnel-like unit 659; and segment 663 which surrounds segment 659 and embeds the ends of segment 657 in transparent material 664. This embodiment threads light transmission lines 656 through segment 645 and stabilizing baffle 639, in which segment 663 enters plug 660, the end of segment 663 reaching inside plug 660 to 661, and the distal end of plug 660 bearing a cap 662 that threads into receptacle 652 in light tube 650, configured to receive 662. Light tube 650 is composed of transparent material 651, which is shaped to receive plugs such as 660 of different lengths.

The above-described embodiment is merely illustrative of the principles of the invention. Changes may be made thereto by those skilled in the art that fall within the spirit and scope of the invention. For example, skilled workers will understand that the light transmission lines may be protected by a sleeve that plugs into a hub, and said sleeve disconnects therefrom when a sensor detects that the mount separates, or excess force destabilizes it. Electric signals may be employed to monitor the sensors and cause the disconnection. Other potential modifications can be discerned by those familiar with the art.

Figure 6E:
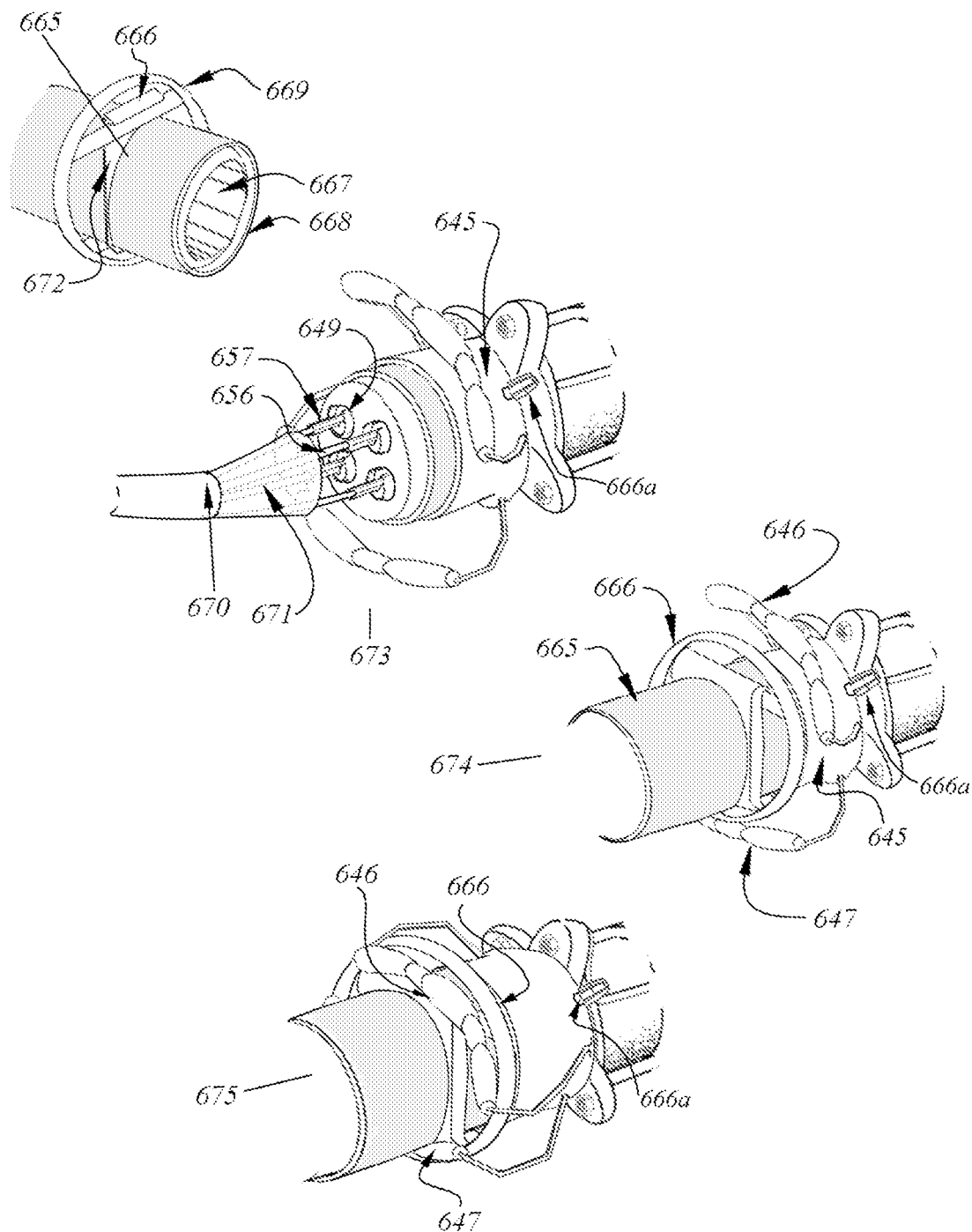
FIG. 6E is a perspective view of a release mechanism in the embodiment in FIG. 6A.

FIG. 6E is an alternate view of the embodiment illustrated in FIG. 6D, showing as well the hollow cylindrical housing 665 that encloses sheathed light guides, pipes, or fibers 655. Flanged cylinder 666 has a portion 672 inserted into and fused with the housing and a ring 669 which surrounds it at a distance of <10 mm, in this embodiment <5 mm. By engaging ring 669 of the flanged cylinder 666 with locking fasteners 646 and 647 on receptacle 645, the light wand can be strongly installed with respect to potential rotating, pulling, and shaking motions. If such motions exceed the photodental device's safety, the fasteners 646 and 647 will disconnect from flanged cylinder 666, and protect the equipment. The interior of housing 665 contains a protective liner 667, surrounded by a resilient hose 668. Housing 665 is flexible, though stiff. Illustration 673 shows the process of sliding light transmission lines 656 into receptacle 645. The light transmission lines are encased in sheath 670, until they reach close to the receptacle 645, where they leave sheaf 670, protected by thin-walled shield 671, and thread into thin tubes 657 inside through-holes 649.

Illustration 674 shows cylindrical housing 665 fitted into receptacle 645, the line lines inserted (not visible), with locking fasteners 646 and 647 around flanged cylinder 666, in an open position. Illustration 675 shows locking fasteners 646 and 647 closed around flanged cylinder 666, in the installed position. This is the operational configuration of the unit.

Figure 6F:
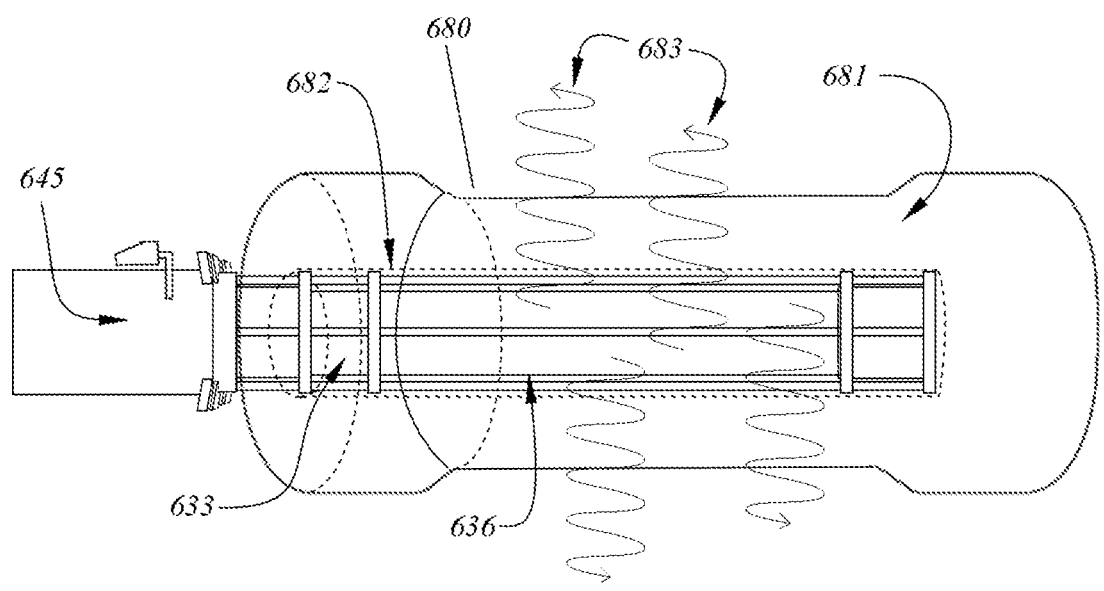
FIG. 6F is a schematic view and illustration of use of the embodiment in FIG. 6A.
Figure 6F:
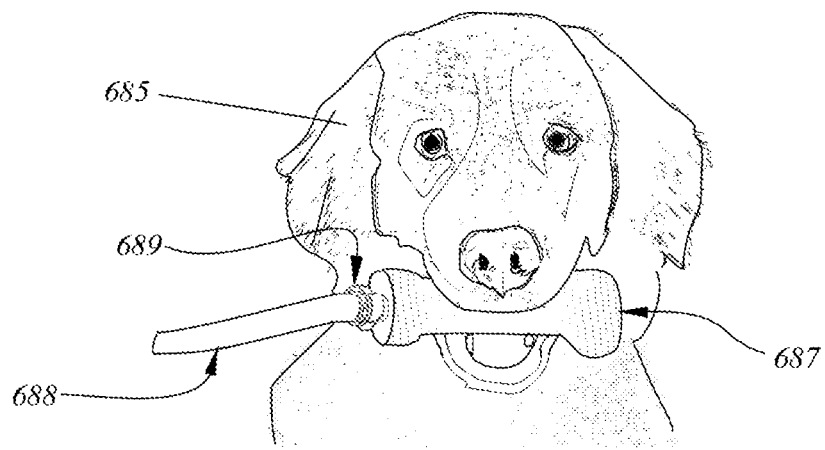

FIG. 6F shows a diagrammatic display 680 of the photodental light wand for animals, in particular dogs, in this embodiment. Receptacle 645 fits into the end of wand 633, whose frame members 636 run longitudinally through an open cavity 682 within external housing 681. Housing 681 is either made of resistant material that is transparent and/or that material contains holes for light 683 from the wand to reach the immediate external environment. Illustration 685 shows a dog holding the photodental light wand, encased in an external housing which has the form of a dog chew toy 687, that may contain food-grade substances that promote synergistic bactericidal effects when precipitated in the presence of specific visible light wavelengths. The optic pipes, guides, tubes, or fibers that illuminate toy 687 are within the flexible hose 688. Quick disconnect assembly 689 can be seen where hose 688 enters toy 687.

Figure 7A:
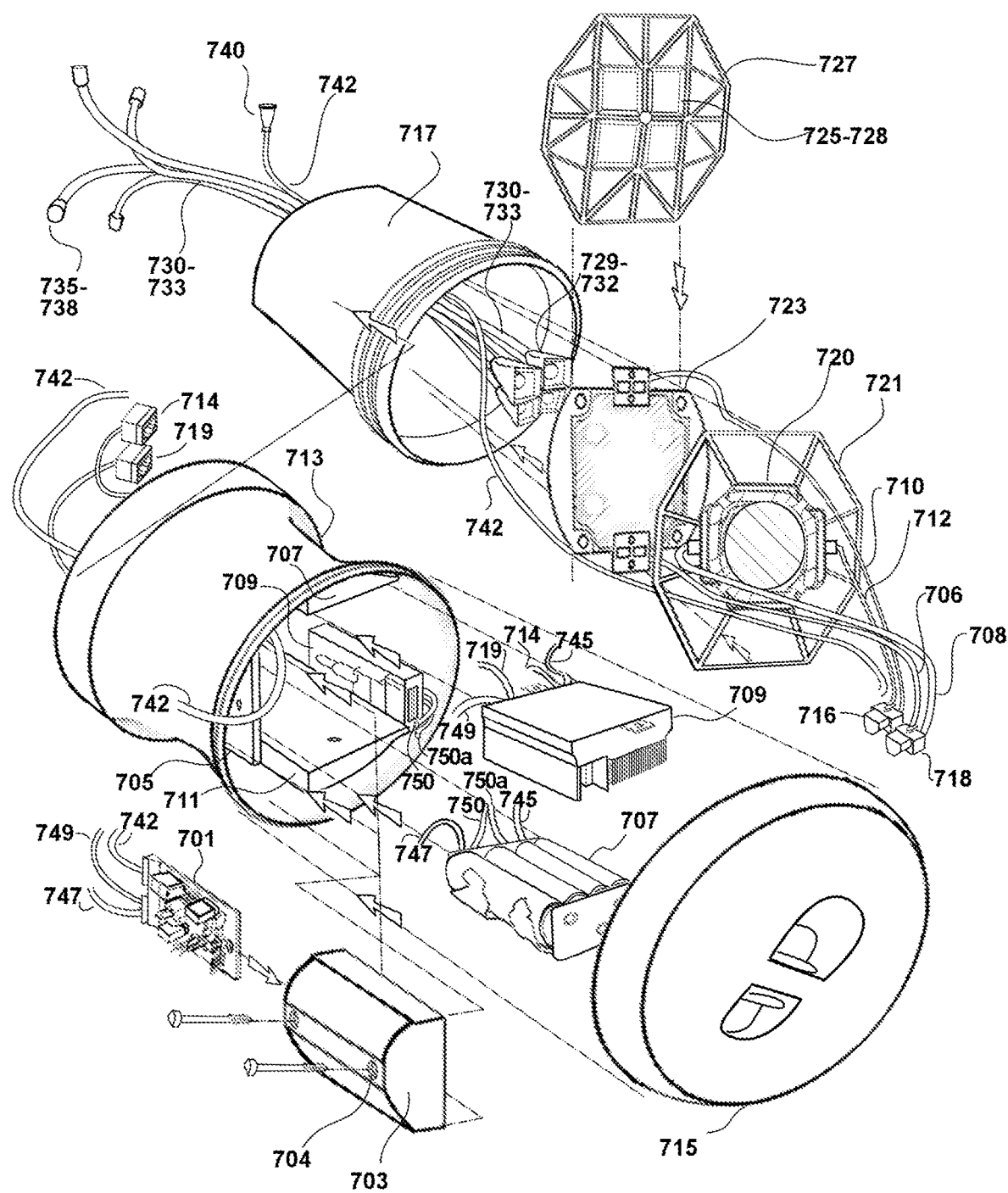
FIG. 7A is an exploded view of a knob-like photodental device for a dog with LEDs.

FIG. 7A is an exploded view of a knob or handle-like component of a photodental device for dogs. This knob attaches to a wand or other extended shape, which optic pipes, guides, tubes, or fibers enter and illuminate. The knob contains all electronic apparati, and is not intended to be part of the dog's mouth play.

Upper receptacle 713 contains battery pack 707, device driver 709, sensor controller 701, and has a screw cap 715 to enclose it. The interior of upper receptacle 713 has bottom structure 711, which is the supporting structure for battery pack 707. Surface 705 is fused to bottom structure 711, and sensor controller 701 and encasement 703 attach to surface 705 with bolts or screws 704. Surface 707 is fused to the upper wall of upper receptacle 713, and device driver 709 attaches to it. USB recharging component 709 fits into the upper receptacle 713 next to bottom structure 711.

Lower receptacle 717 contains light emitter 723, in this embodiment, high power LEDs, a piezoelectric cooling device 720, and in this illustration four light guides, pipes, or fibers 730-733, each of which has end fittings 729-732, which are secured in footings 725-728. Framework 727 supports footings 725-728, as well as light emitter 723. Framework 721 supports cooling device 720. Lower receptacle 717 attaches into upper receptacle 713.

Light guides, pipes, or fibers 730-733 extend into a wand or other shape, where they end with luminaire caps 735-738 that direct light efficiently outward. Sensor 740 detects light or other environmental variable, and sends signals on line 742, which threads through the lower receptacle and into the upper receptacle, where it is attached to the PCB board 701 that switches the photodental device on or off.

Light emitter 723 is powered by lines 710 and 706, and piezoelectric cooling fan 720 is powered by lines 712 and 708. 710 and 712 both have the same charge polarity, and are fitted with end connector 716. 706 and 708 both have the same charge polarity, and are fitted with end connector 718. In the upper receptacle, end connector 716 is inserted into connector block 714, and end connector 718 is inserted into connector block 719, from which lines 714 and 719 enter the upper receptacle 713 and attach to the device driver 709.

Device driver 709 electrical line 749 is attached at the other end to sensor controller 701, and device driver 709 electrical line 745 is attached to battery pack 707. Battery pack 707 electric line 747 is attached to sensor controller 701. Battery pack 707 electric lines 750 and 750a are attached to the USB recharging component 709.

There are four possible functions of the knob element. The first function is to enable the photodental device to switch on and off. Sensor 740 transmits information through line 742, to sensor controller 701 in the upper receptor 713. If a threshold is reached, controller 701 activates device driver 709, which closes the circuits between light emitters 723 and cooling fan 720 and battery pack 707, thereby switching on the device. It should be understood that there is also an override switch, which a human operator can use to turn the device off or on.

The second function of the knob element is that the knob or handle is located apart from the part of the device held by a dog in its mouth. That reassures users that a dog with particularly strong jaws and/or teeth won't puncture any electronic equipment. The knob device is unique in having light emitters close to the chew toy, but not in it. That way little light is lost by light guide attenuation, permitting high powered illumination.

The third function of the knob element is that it can be held by a human user, who then uses the attached wand or other shape for play with a dog. Some dogs enjoy this kind of play, and the human user can ensure that the device switches on when the dog has the wand or other shape in its mouth. It is also possible for a human operator to switch the device on and off wirelessly.

The fourth function of the knob element is that it can be configured as the handle of a tooth brushing instrument, and the attached wand configured with cleaning elements, such as bristles. In this case wand illuminates the interior of a dog's mouth while simultaneously a human user can, using the knob, brush the dog's teeth. The tooth brushing configuration is modified so that the knob controls rapid movement of the attached wand, and the attached wand's housing supporting outwardly oriented cleaning elements.

Figure 7B:
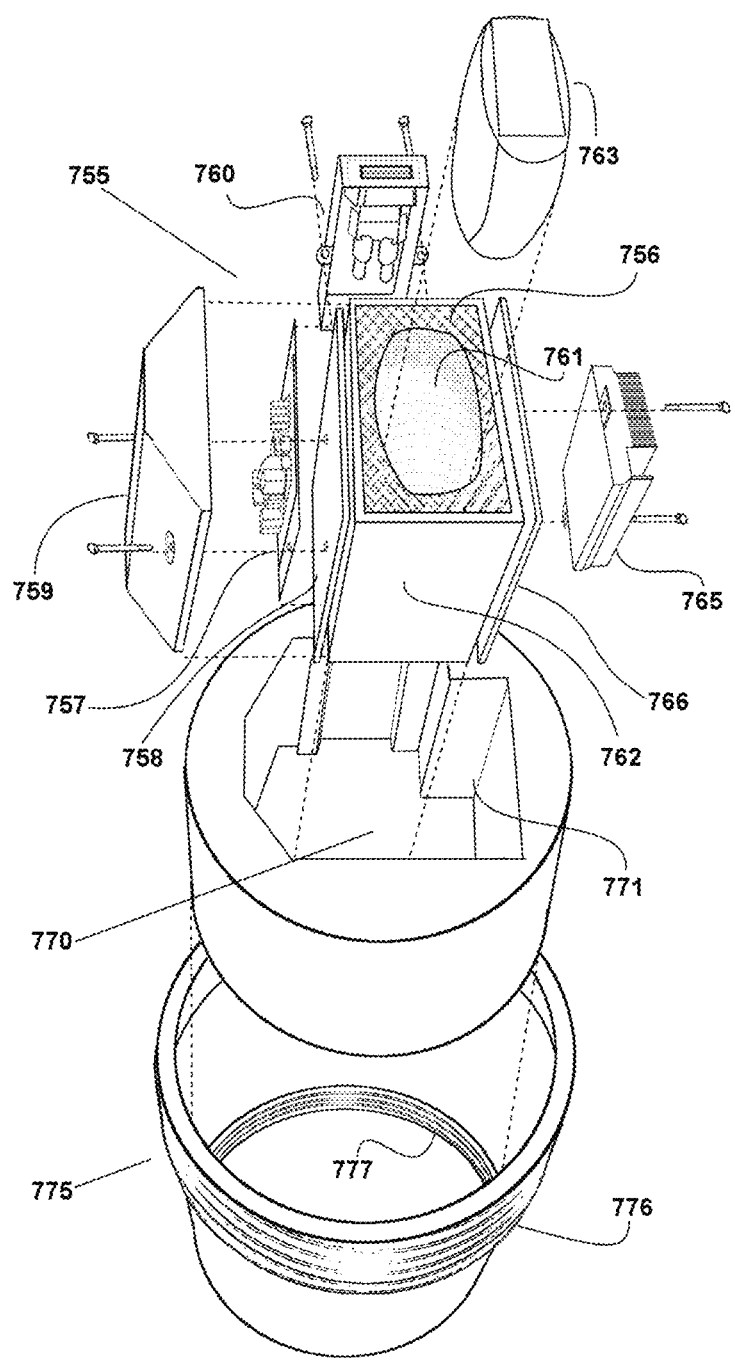
FIG. 7B is an exploded view of a knob-like photodental device for a dog without LEDs.

FIG. 7B is an exploded view of the knob of a photodental device for animals, especially dogs, used with a wand or shaped object that illuminates a toy-like chew object. In this case the knob can be used with an attachment that contains electronic light emission technology, or can be used with a wand or shape that contains light emission technology inside of it, so that light emitters directly illuminate the external environment, rather than plug into light guides, pipes, or fibers that transport light to the region where light illuminates the environment. Assembly 755 is composed of receptacle 762 which contains porous material 756 that surrounds a cavity 761. Concretely, 756 has micro or medium-scale holes, such as woven plastic fibers or the like, which may be impregnated with a resin to produce a stable, strong plastic structure. A rechargeable battery 736 fits into cavity 761. Light emitters driver 765 attaches to receptacle 762 via plate 766, and sensor controller 757, as well as controller cover 759, attach to receptacle 762 via plate 758. USB recharging device 760 attaches to the side of receptacle 762.

Assembly 755 fits into thick liner 770, composed of materials 771 that provide stability and shock attenuation, for which various dense elastomers such as vinyl nitrile may be suitable, as well as many other materials. Thick liner 770 fits into housing 775, which is the outermost layer. The material used for housing 775 can be a polycarbonate plastic, thermoset, elastomers, thermoplastic, composites, metals, ceramics or other materials. Housing 775 contains external screwing threads 776, so that a resilient cap can be installed. It also contains inner screwing threads 777, so that the this knob can be attached to a wand or shaped object which contains electronic light emission technology. Alternatively, a knob attachment that contains electronic light emission technology may be screwed onto the end of this knob, from which optic pipes, guides, tubes, or fibers thread into a wand or shaped object.

Figure 7C:
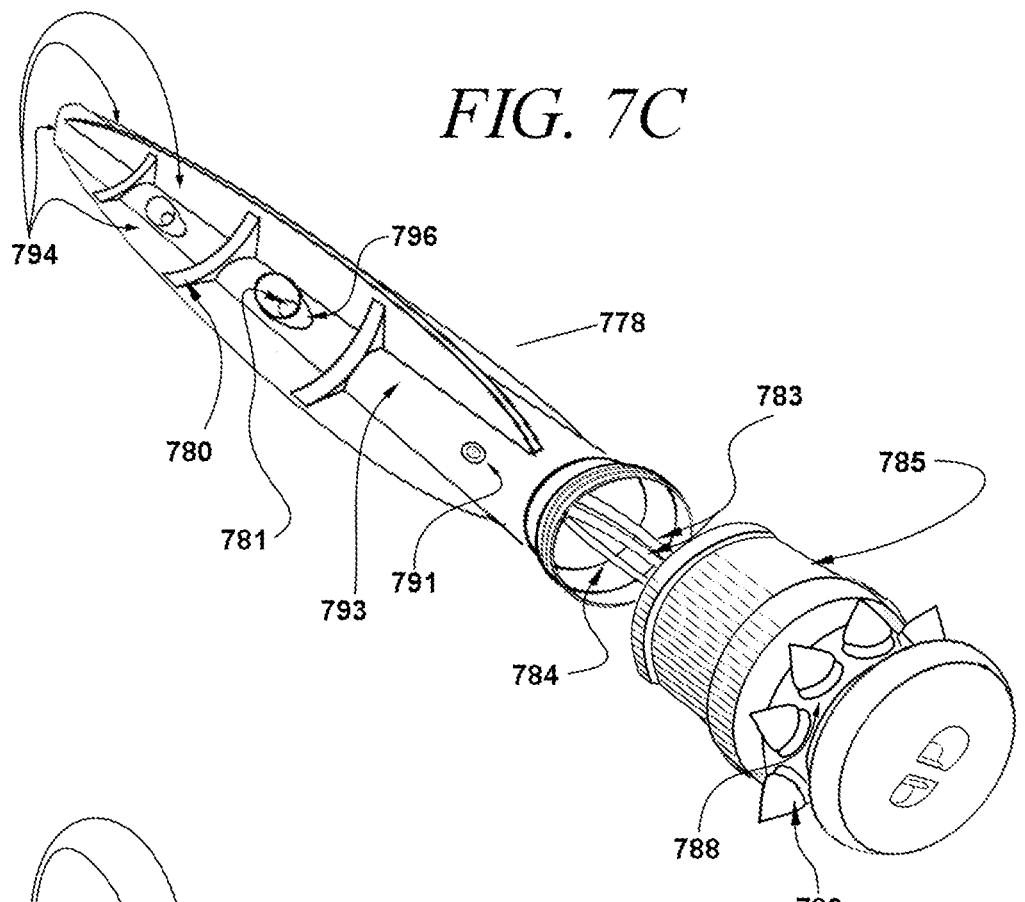
FIG. 7C is a perspective view of the embodiment in FIG. 7B.

FIG. 7C illustrates a perspective view of a photodental device for an animal, especially a dog, that includes a knob 785, such as the knob configured in FIG. 7B, with electronic lines 783 running into shaped illuminating member 778, to power light emitters, such as LEDs 781, inside emissions cones 796, and with sensor communication line 784 running from sensor 791 into knob 785. The shaped illuminating member 778 contains laminae 794 constructed from resilient materials. The shaped illuminating member 778 can be characterized in three-dimensional space with a Cartesian coordinate system. A reference plane 793 is centered between any two laminae 794. Reference plane 793 may be considered the x-y plane, with laminae 794 extending in the y-z plane. Two laminae 794 are not visible, on the other side of shaped object 778. Bridge supports 780 span the object surface between laminae 794.

The method of making the shaped object with structural support laminae 778 includes machining of, or casting in, resilient materials. Machining or casting dimensions may be defined by mapping the surface and laminae in the x, y, and z directions. Laminae 794 are orthogonal to the surface 793. One of regular skill in the art understands that proper lamina dimensions establishes lamina stiffness and prevents buckling, thereby protecting the shaped object from damage. In general, lamina may 794 be comprised of a variety of machinable plastics or metals.

Other embodiments can produce a similar outcome, using similar principals. Instead of laminae, other embodiments can use blocks that extend only a short distance above the illuminating member surface, with a thickness that enables them, together, to cover a significant amount of the external surface. Still other embodiments can be discerned by those familiar with the art.

Figure 7D:
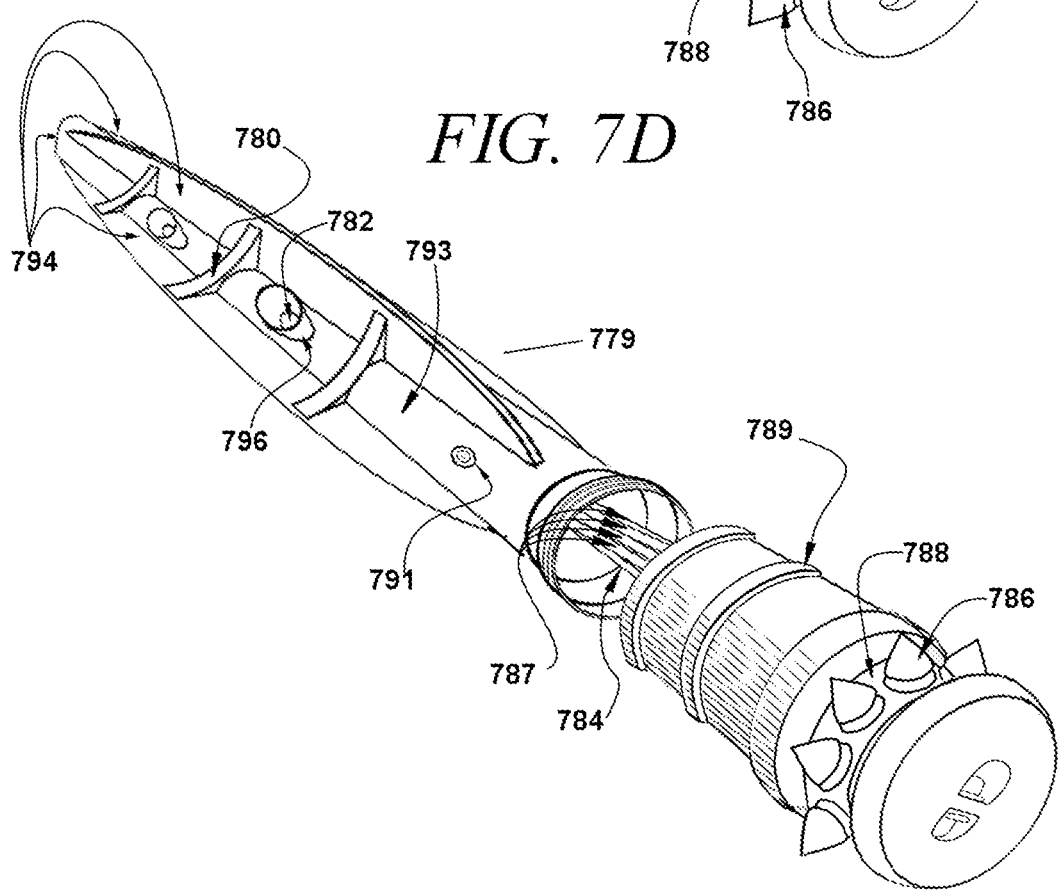
FIG. 7D is a perspective view of the embodiment in FIG. 7A.

FIG. 7D illustrates a perspective view of a photodental device, for an animal, especially a dog, that includes a knob 789, such as the knob configured in FIG. 7A, with multiple light guides, pipes, or fibers 787 running into shaped illuminating member 779, to illuminate luminaires 782, inside emissions cones 796, and with sensor communication line 784 running from sensor 791 into knob 789. Shaped objet illuminating member 779 contains identical surface structure as shaped illuminating member 778 above, and has the same methods of being made. Shaped illuminating member 779 has no electronic light emitters inside, only passive luminaires 782.

Knobs 785 and 789 include anti-chew elements 786, prongs or sharp studs extending from the base around the neck of the knob. In this embodiment, the anti-chew elements 786 are integrally attached to a flexible strap 788 that serves as a belt and forms a tight fit around the knob. Alternatively, the anti-chew elements may be cast with the base as one piece, or press-fit into openings in the base to form an interference fit. Anti-chew elements 786 serve to prevent animals, especially dogs, from chewing on the knob.

Figure 7E:
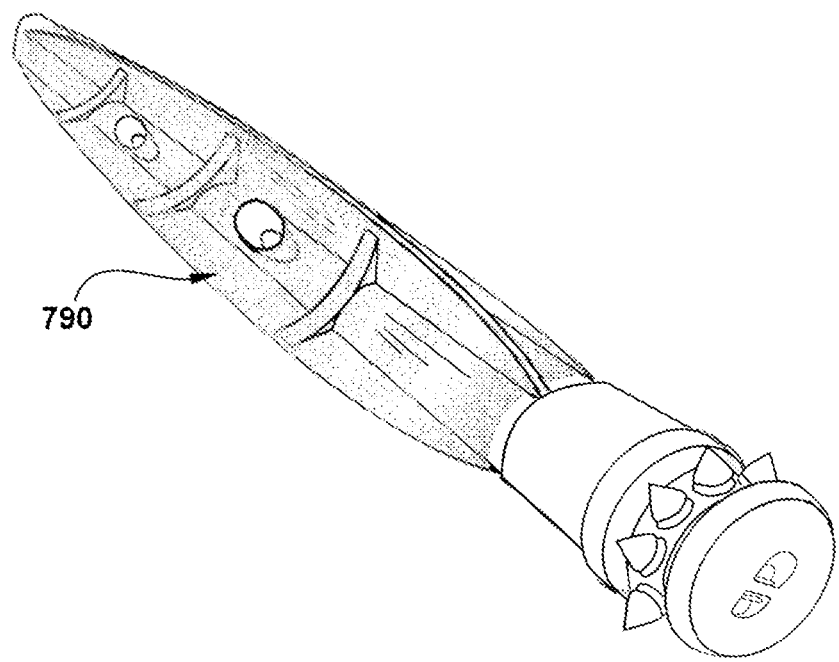
FIG. 7E is a partially assembled view of the embodiments in FIGS. 7A and 7B.

FIG. 7E is a perspective illustration of a knob-based photodental device for animals, especially dogs. It includes a knob and shaped object coupled together, and shows a material 790 that fills the space between the shaped object surface and laminae. Material 790 has a high modulus of resistance, flexibility, and is waterproof. Elastomer material that dissipates stress energy, such as thermoset, thermoplastic, or other material for thermoforming, may be used. The material has durometer hardness in a range of 30 to 80 Shores A, preferably formed by injection molding or any other suitable molding technique known in the art. The result is that the shaped object is composed of rigid laminae and more flexible material 790, which allow the shaped object to deform a bit if necessary. The laminae ensure that the shaped object's structure remains coherent.

Figure 7F:
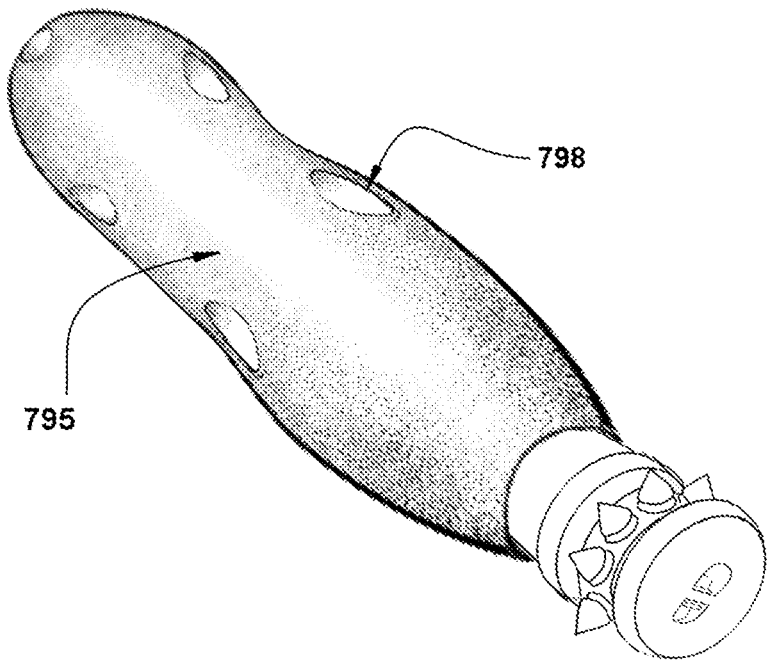
FIG. 7F is a fully assembled view of the embodiments in FIGS. 7A and 7B.

FIG. 7F illustrates the knob-based photodental device for animals, especially dogs, with the outer housing 795 in place. Depending on the number of luminaires or LEDs in the shaped object, there will be a number of apertures in the housing for light to pass. It is to be understood that housing 795 is designed to conform to the interior of a dog's mouth. Apertures 798 in housing 795 are not in its narrowest part. When dog's chew, they enjoy having objects rub their gums, where PD biofilms are. Housing 795 is configured to deliver light in bulges, which may be pushed against interdental spaces by dogs.

As with all outer housings that are in contact with an animal's mouth, housing 795 may have specific compounds impregnated or otherwise distributed in it. These compounds work in a synergistic way with specific light frequencies to kill dental disease bacteria.

Figure 8A:
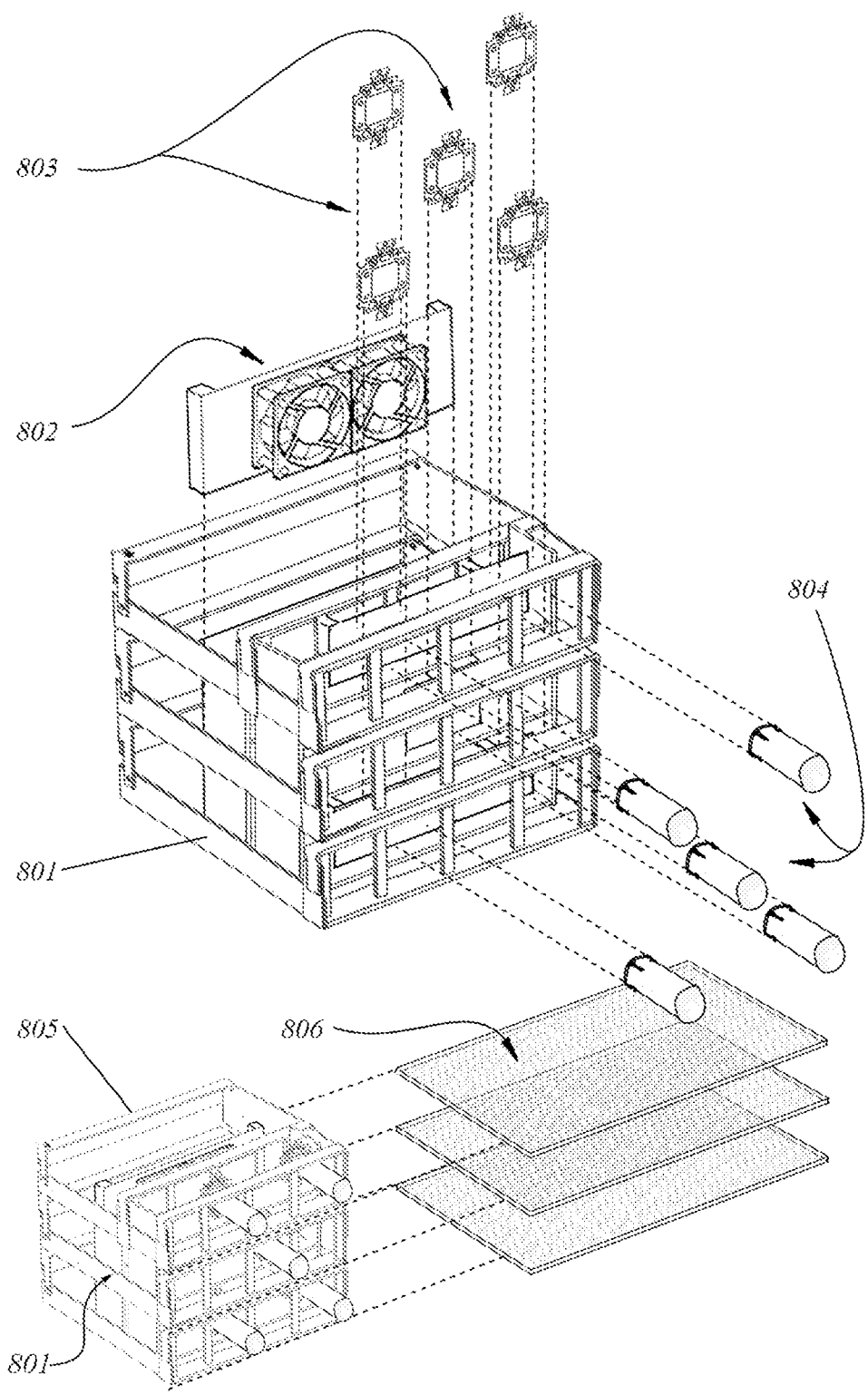
FIG. 8A is an exploded view of part of a base unit in a photodental device for a dog.

FIG. 8A is an exploded perspective view of part of the generating unit of a photodental device for animals, especially dogs, that has a tether system. This embodiment is directed at implementations where the animal-held device, such as a chew toy, does not disconnect from a tether. Under extreme conditions a dog with a particularly powerful jaw grip or head movement may impose excessive forces on the light transmission lines, which connect in a generating unit to light emitters. It may be useful to have a "shock absorbing" system to protect light emitters and light transmission lines.

Structure 801 is the rear-most component in the generating unit, and has slotted positions for cooling systems 802, batteries or electric cables (not visible), as well as LEDs 803 and LED optical ducts 804. LED duct 804 is a compound parabolic concentrator conjoined to a prism block filled with dielectric plastic. The plastic must have low absorbance, such as acrylic. To maintain total internal refraction, the connector's internal plastic shape may be elliptical, and the internal plastic has a higher refraction angle than the surrounding transparent material. It is critical in all light guide systems to maintain source luminance through entendue preservation.

Illustration 805 shows the assembled LEDs, optical ducts, and cooling devices within structure 801. Horizontal sieve floors 806 provide integrity to structure 801.

Figure 8B:
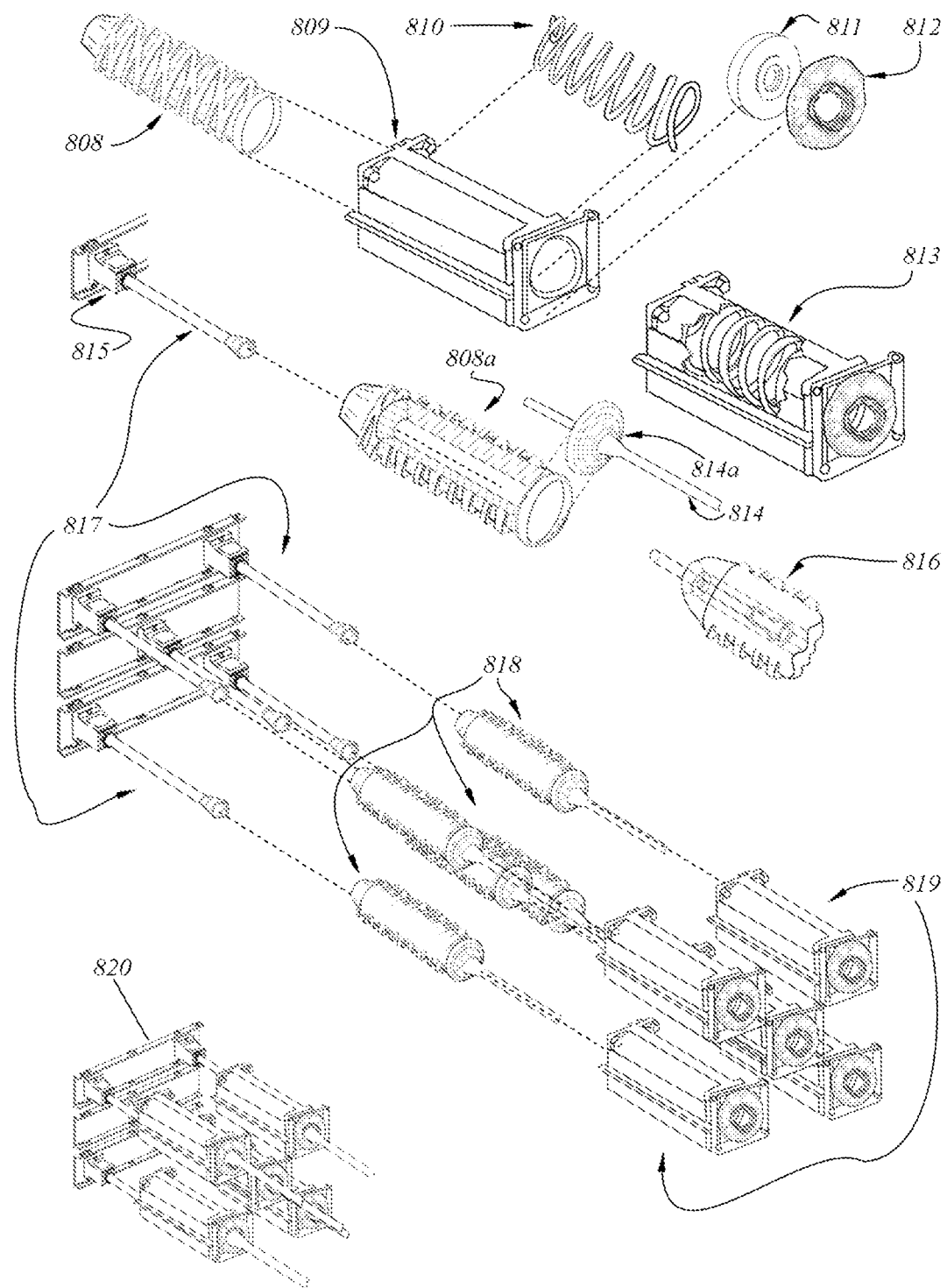
FIG. 8B is a perspective view of component elements of the embodiment in FIG. 8A.

FIG. 8B displays components of a "shock absorbing" arrangement for a light emissions generating unit in this embodiment. In particular, it shows the mid-phase components of the generating unit. Coupling 815 connects to the light ducts 804 from FIG. 8A, and includes a light pipe 817 of about 3 to 15 mm, or other suitable length, with internal conical taper for fitting into coupling 815. Light pipe 814 inserts in module 808, into a central cavity visible in 808a. Illustration 816 shows light pipe 814 inside this cavity. The interior cavity of module 808 is a hollow tunnel with surfaces that reflect light through mirroring or total internal reflection, so that light transmitted from proximal light pipe 814 is transmitted through the hollow tunnel. Distal light transmission line 814 enters module 808 from the opposite side. It may be pushed close to the light pipe 817, or a gap between them may remain. The distal light transmission line has a fitting 814a that is pushed against module 808, and may be attached there.

On its outside surface, module 808 has a spiral of solid material, said spiral being skewed or tilted from a vertical axis to some degree. Module 808 is itself inserted into a cavity in enclosure 809. On the inside of the outer surface of enclosure 809 is a spiral of solid material 810, which mirrors (off axis in the opposite direction) the skew or tilt of the spiral shape around module 808.

Thus, if force is exerted on module 808, transmitted by the distal light transmission line 814, and module 808 is pulled toward the front of the generating unit, the spiral shape on its surface will rub against the opposing spiral shape on enclosure 809. Given the spiral shapes are tilted in opposite directions, friction will dampen the external forces.

The dynamic dampening of forces of this aspect of the embodiment does not require feedback sensors, gyros, or accelerometers, but only a simple hardware adaption. In further embodiments of the invention, the principal of competing or contradictory spiral surfaces may be used on a larger scale, over a longer distance, as the primary shock absorbing technique in an embodiment. In this embodiment it is one of several shock absorbing techniques.

Enclosure 809 has, at its distal opening, a pliant funnel 811 on the inside face of that opening, and a soft washer 812 on the outside face of that opening. Drawing 813 shows the enclosure 809's internal spiral in a cut-away, and the soft washer 812 as when assembled.

A coupler 815 is attached to a light pipe 817, which enters module 808a, which has its surface cut away to reveal the hollow tunnel inside. Illustration 816 shows light pipe 817 inside the tunnel. Distal light transmission line 814 inserts into the hollow tunnel from the front, with fitting 814a pressed to the front of module 808a. Enclosure 809 surrounds fitting 814a, to secure it in place. If force is exerted on distal light transmission line 814, fitting 814a may be pulled through the pliant funnel 811 and soft washer 812, against their resistance. Unless the animal's force exceeds a threshold that could damage the generating unit or other components of the invention, said resistance to 814a movement prevents disassembly.

The impulse of force transmitted to the light transmission lines inside a generating unit are a fraction of the total force induced by an animal's movement of the distal end of the transmission lines, because the tether system absorbs most of it. Since light emitters, fittings, and lines may be delicate, even fractional forces are important. Damping achieved by component movements can be measured by the relative movement of the damped object, and the object that holds or supports it. If the light transmission components move, because of damping components, 2.5 mm (~0.1 in), while the scaffolding moves 0.25 mm (~0.01 in), light transmission components absorb 1/10 of the impact the scaffolding gets. Hence damping serves to massively reduce potential risk to light components.

Assembled light pipes 817 insert into assembled modules 818, which are themselves inside assembled enclosures 819. Drawing 820 shows their final assembly. The logic of this assembly is that physical structures can be nested and differently exposed to forces, and despite proximity, increase the probability that each component and the structure will resist forces, but disassemble gracefully if a threshold is crossed. Those skilled in the art will recognize that other alternatives can accomplish this goal. For example, taping can be used to keep elements together, the tape having a known adhesion capacity that meets the needs of protection. It will be obvious to those skilled in the art that it is possible to combine some of the components described above, such as module 808 and enclosure 809, with different mechanisms, to achieve similar goals, without departing from the scope of this embodiment.

Figure 8C:
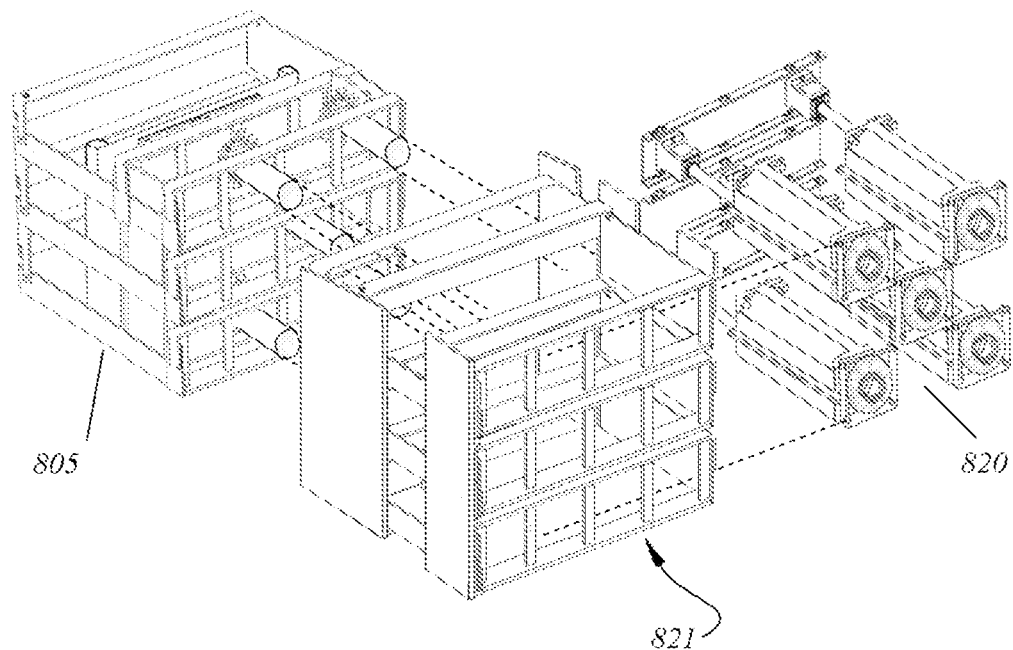
FIG. 8C is a perspective view of a partial assembly of the embodiment in FIG. 8A.
Figure 8C:
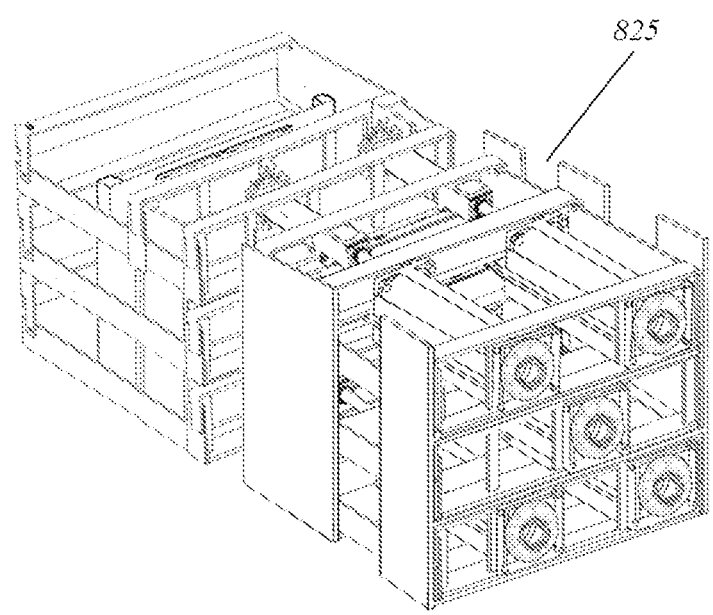

FIG. 8C displays components of a "shock absorbing" arrangement for a light emissions generating unit in this embodiment. In particular, it shows the rear-most component assembly 805 and mid-phase component assembly 820 as they relate to scaffolding 821, which supports mid-phase components 820 as they back into rear-most components 805. Drawing 825 shows the completed scaffolding, light emitters, and holders assembly, the rear-most, mid-phase, and scaffolding combined as the rear body of the generating unit.

Figure 8D:
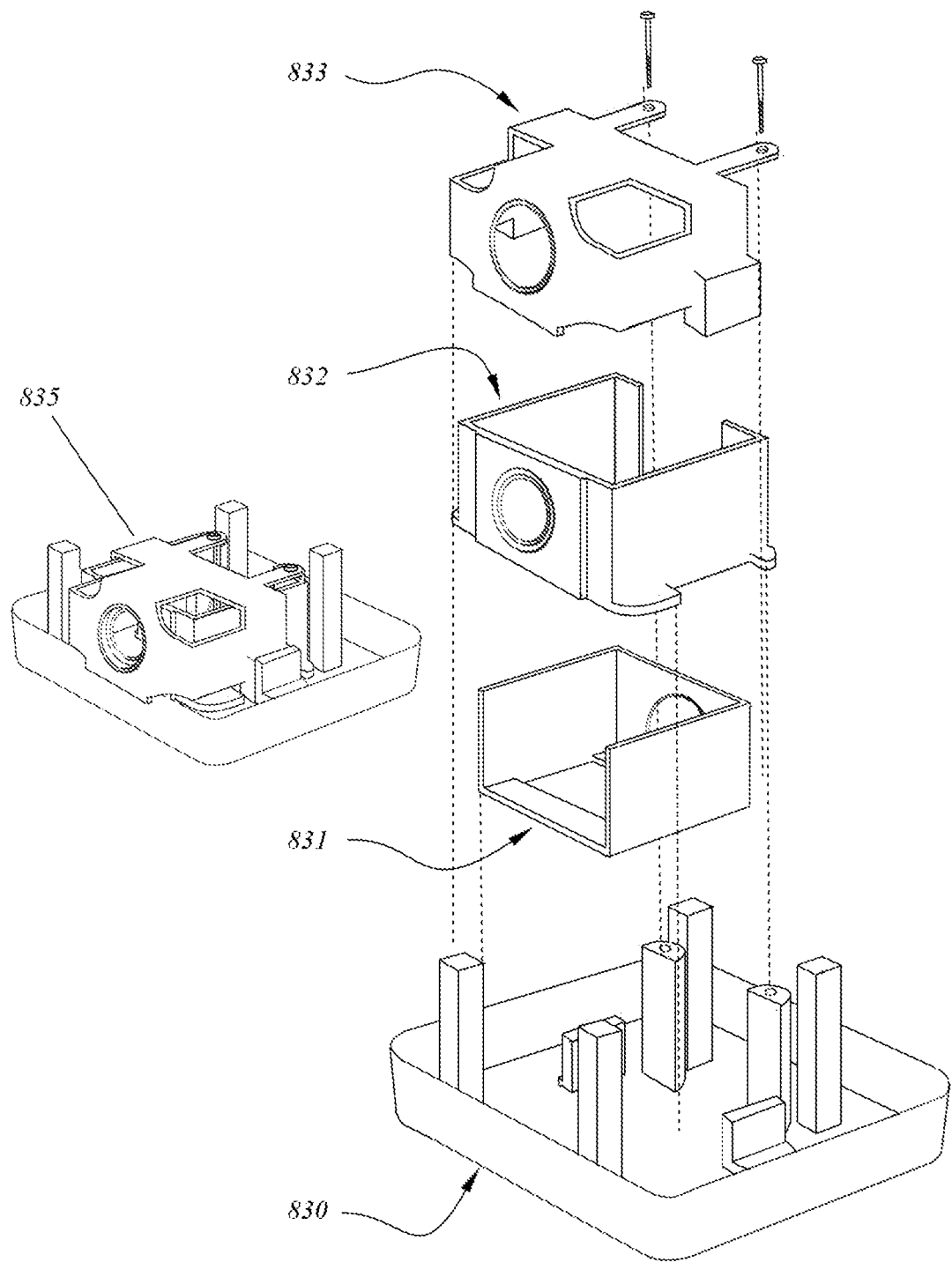
FIG. 8D is an exploded view of the front part of a generating unit of the embodiment in FIG. 8A.

FIG. 8D is an exploded perspective view of part of the generating unit of a photodental device for animals, especially dogs. It shows the front part of the generating unit, which contains the point of entry for an umbilical hose containing light transmission lines, passing from the external environment into the generating unit. Transmission lines enter front shelter shell 832's front orifice, and could potentially cause pulling friction. Transmission lines leave through front shelter shell 831's rear. Front shelter shell 831 is separate from rear shelter shell 832, 831's rear aperture is large enough to prevent friction from transmission line movements, and it is held inside columns on plate 830. Front shelter shell 831 avoids the forces transmitted to rear shelter shell 832.

Top shelter shell 833 is also isolated from applied forces, as it covers shelter shells 832 and 831 without being attached to them. Top shelter shell 833's front aperture is sufficiently large to avoid transmission line friction, and it screws into columns on plate 830. By recruiting separate shells in a nested assembly, rather than using a single housing, applied forces dissipate. Only rear shelter shell 832 directly touches light transmission lines, and when transmission line friction pulls at 832, the force isn't transmitted to front shelter shell 831 or top shelter shell 833. The assembly helps maintain structural integrity, but allows for light transmission line motions.

Light transmission lines have slack that may gather on the floor of plate 830. The logic of such an assembly can lead to different combined structures, of which this, which is shown as an assembled unit in drawing 835, is but one possible example.

Figure 8E:
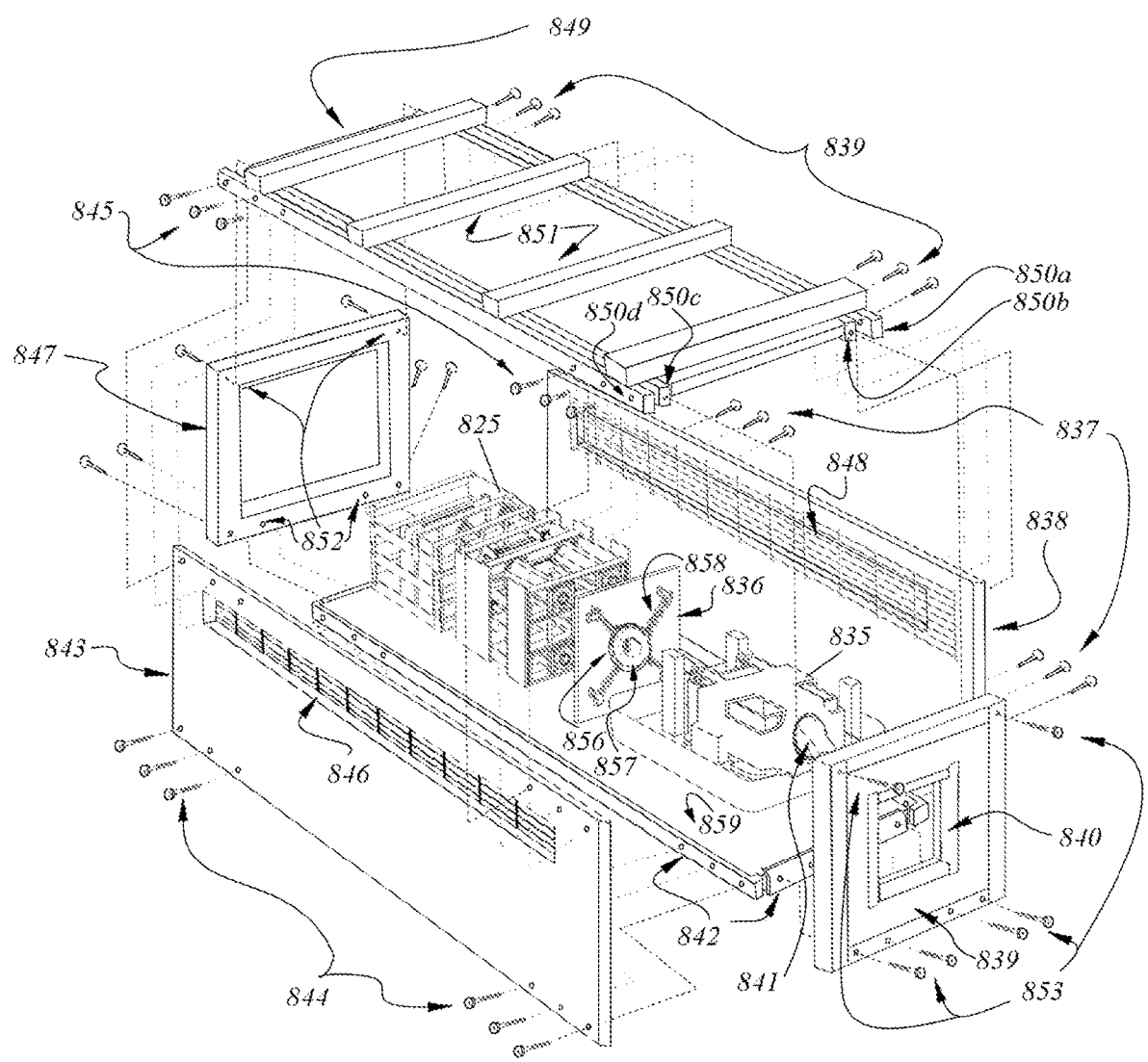
FIG. 8E is a partially assembled view of the embodiment in FIG. 8A.

FIG. 8E is an exploded perspective view of the generating unit of a photodental device for animals, especially dogs, that has a tether system. The generating unit electronic elements 825 are composed of components assembled in scaffolding that together permit but resist light transmission line movement. In the event an extreme pulling force is exerted on the light transmission lines entering electronic elements, they may be pulled out of electronic elements 825.

Barrier 836 is between electronic elements 825 and the front part of the generating unit, where nested housings permit slack in the tethered lines. Barrier 826 includes an aperture 856 which light transmission lines must pass through, but they further must pass through damping member 857 of circular cross section, with an inner surface that defines a hollow core through which light transmission lines pass. The damping member has a Shore A hardness of between 10 and 40 A. The exact hardness and properties depends on the variations in processing and the type and amount of chemicals used.

Light transmission lines fit snugly within damping member 857. If one or more light transmission lines is pulled under extreme force, damping member 857 will swing out from barrier 836, as it is attached by springs 858. In the event that light transmission lines are pulled so hard they threaten to breach barrier 836, damping member 858 may detach from springs 858, and remain in contact with the light transmission lines.

It should be clear that many aspects of this embodiment, including the flexibility of light transmission lines in modules, the partial resistance of light transmission line forces and the damping of light transmission line movements, combine to reduce the impact of external forces.

This continues in the generating unit's front assembly 835, where nested shelter shells resist transmission of external forces, and light transmission lines can move without inducing hysteresis in the surrounding structure. Extreme forces, or a reduction in tethering efficiency, can be managed by the generating unit shock absorbing features. Under extraordinary circumstances, light transmission lines may be pulled all the way out of the generating unit. That is better than breaking it. Light lines can be threaded back into the generating unit's components by users.

The rear, middle, and front of generating unit components are attached to surface 859. That surface has side rails 842 with holes for screws to fit in. At the front of front assembly 835, a swivel arm 841 spools out the hose containing light transmission lines. All these elements are enclosed in a generating unit container with six sides, one of which is surface 859. Front generating unit container element 839 contains a window 840, where swivel arm 841 will stick out. The reinforced front generating unit container is attached to the surface rails 842, and to top generating unit container rails 850*b* and 850*c*, with screws or bolts 839.

Left side casing 843 includes screened in open window 846, and attaches to surface rails 842 and top casing rails 850*d* with screws or bolts 844. Rear casing 847 attaches to surface rails 842 and top casing rails 850*b* and 850*c*, with screws or bolts 852. Right side casing 838 attaches to surface rails 842 and top casing rails 850*a*, with screws or bolts 837. Top casing 849 is built from rails 850.

Figure 8F:
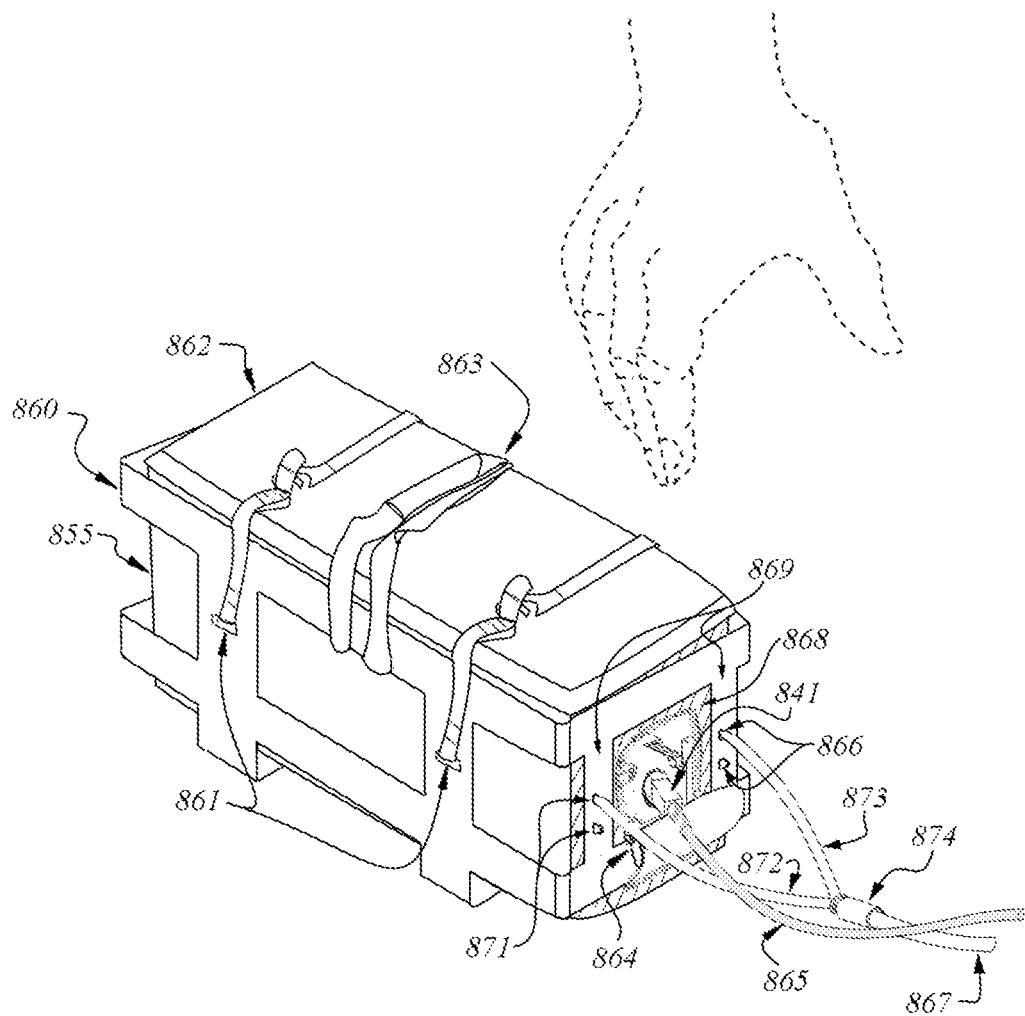
FIG. 8F is a fully assembled view of the embodiment in FIG. 8A.
Figure 8G:
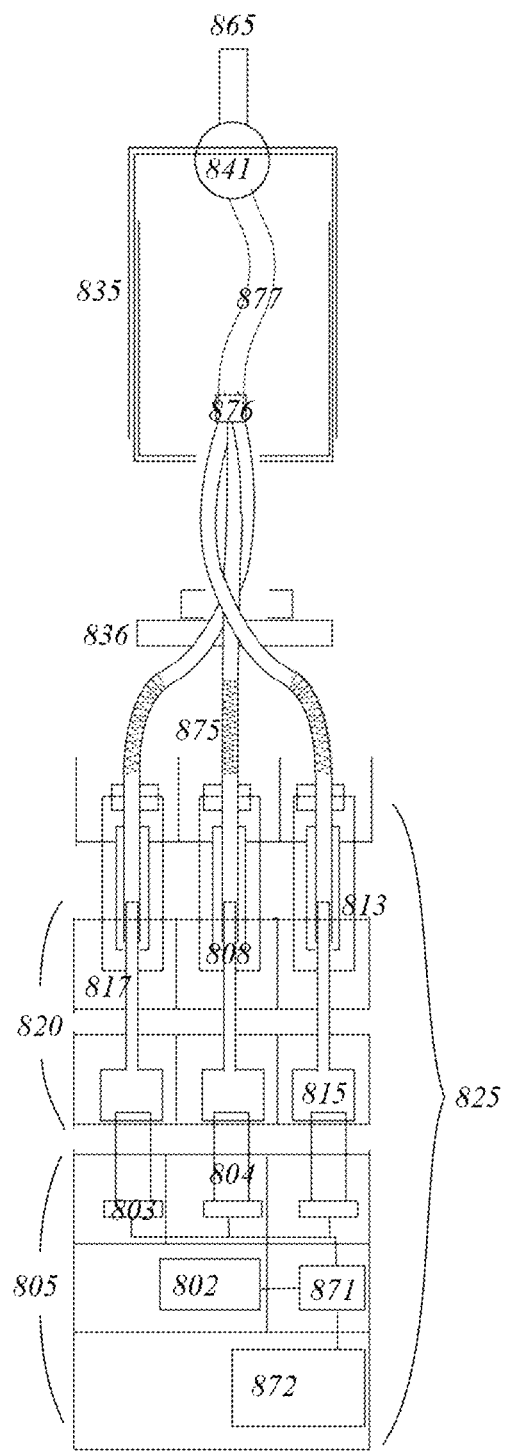
FIG. 8G is a schematic view of the embodiment in FIG. 8A.

FIG. 8F is a perspective illustration of a photodental device for animals, especially dogs, that has a tether system. It shows the generating unit assembled, and inside a carrier. Casing 855 is visible, assembled. Carrier 860 surrounds casing 855, protecting it. A lid 862 fits over the casing, and straps 861 close it. Straps 863 are designed to be used for carrying the carrier. A hand is illustrated for scale.

At the front of the carrier 860, umbilical hose 865 containing optic pipes, guides, tubes, or fibers is spooled or attached from swivel tube 841. Access to swivel tube 841 is through an opening, in this embodiment a zippered opening 864 that is part of the front-facing fabric surface 868, which covers the front side casing. Carrier 860 includes structural components such as 869, which on the front side have anchor holes such as 866, in which tethering cord 873 is attached, and anchor holes 871, in which tethering cord 872 is attached. Cords 872 and 873 are two separate cords from anchor holes 871 and 866 to convergence point 874. From convergence point 874, cords 872 and 873 intertwine or fuse to form one entity 863.

While not being bound by any theory, the utility of this embodiment may be due to many damping and resisting forces used to delay, but not prevent, the separation of components, rather than having the generating unit components break or separate in a rapid and uncontrolled manner. Other alternatives, with a variety of architectures, may also be used to achieve this.

Figure 9A:
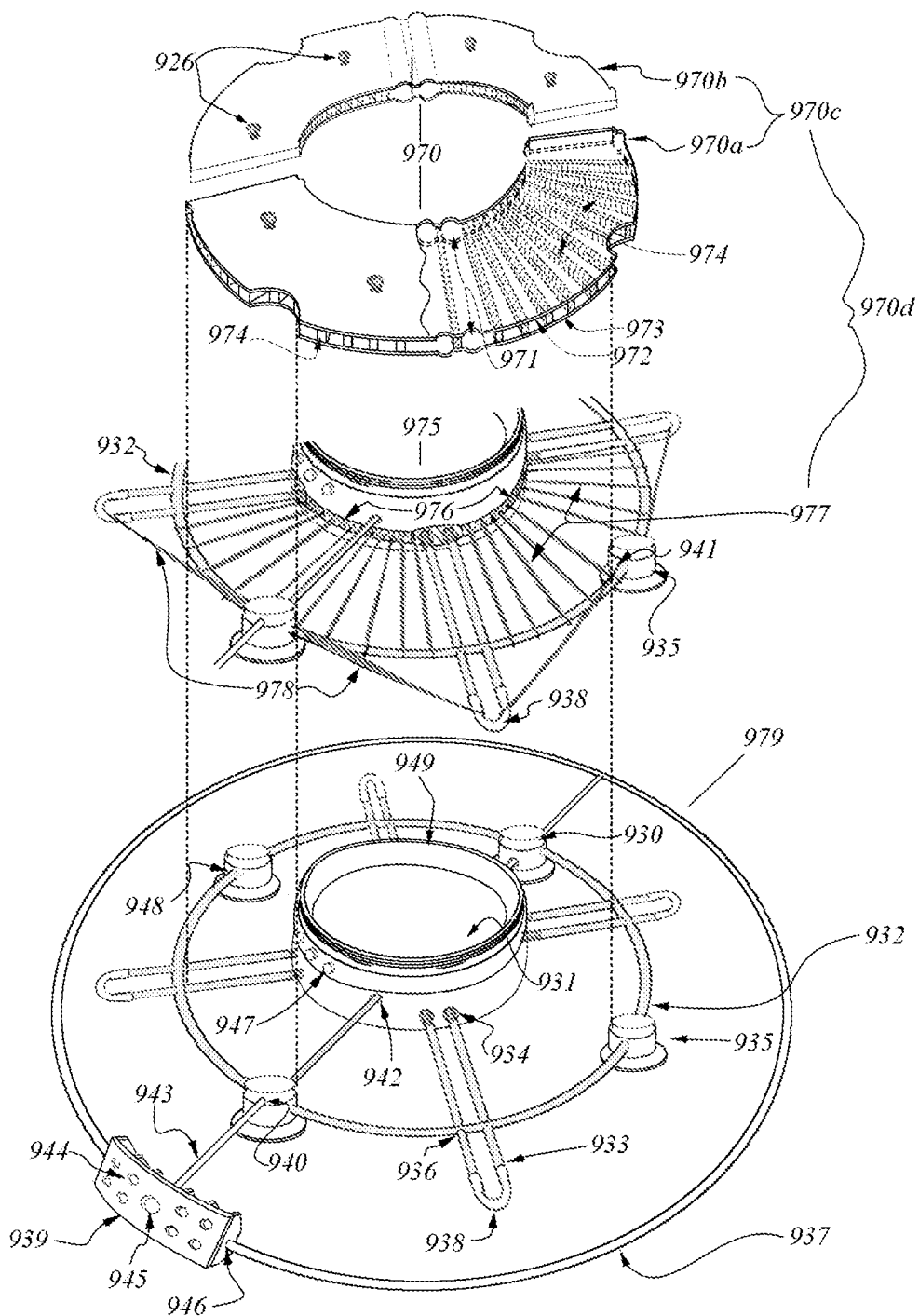
FIG. 9A is an exploded view of a shock absorbing photodental device for a dog.
Figure 9B:
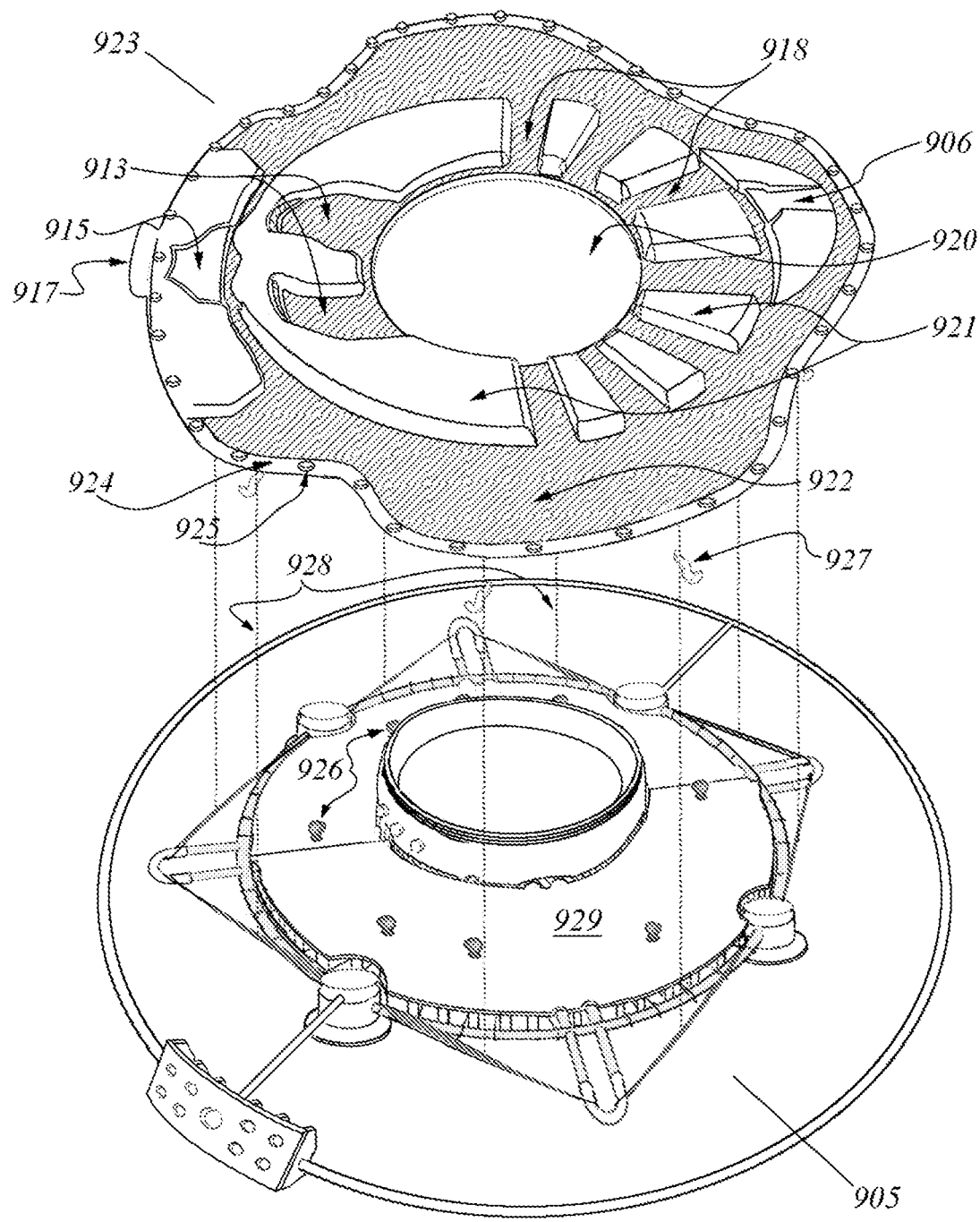
FIG. 9B is an exploded view of a partially assembled embodiment shown in FIG. 9A.
Figure 9C:
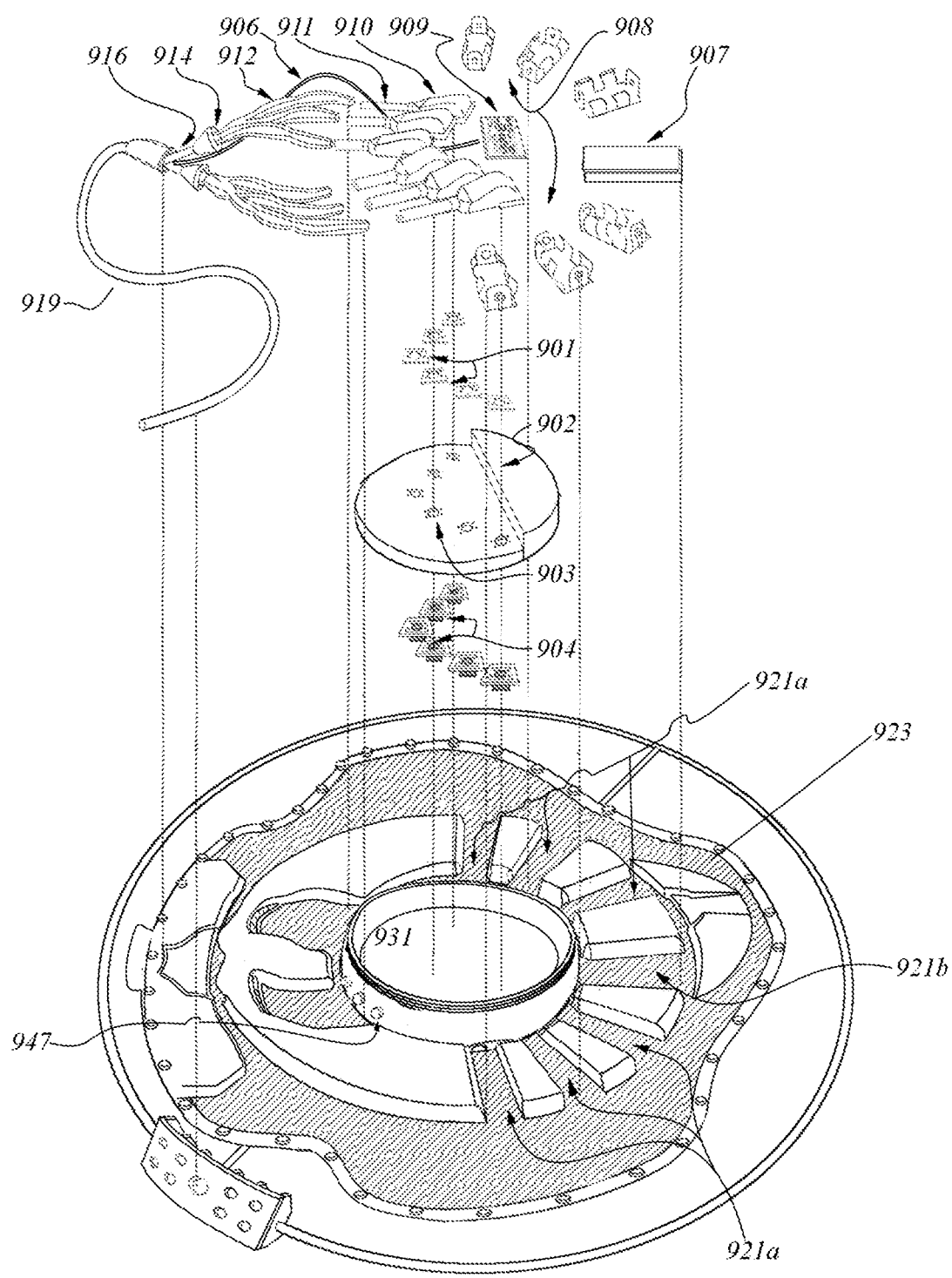
FIG. 9C is an exploded view of a further assembled embodiment shown in FIG. 9A.

FIG. 9A is an exploded view of a flexible, shock absorbing photodental device for dogs, that shows the first steps in its assembly. Illustration 979 shows a ringed apparatus, composed of two circular or elliptical rings made of metal or other resilient material, one of larger circumference 937, and one of lesser circumference 932 that rests inside larger ring 937, that are shaped, sized, and positioned to keep a light emitting assembly stable. A mounting bar 943 made of resilient material is attached to the outer ring 937 across its full diameter, and is flexibly attached to inner ring 932 through footing holes 940 and platform holes 942. Tethering cords (FIG. 9E 993) attach through anchor slots or holes 944 in connecting plate 939, attached on the outer ring 937 via guide holes 946, and if extreme force pulls on them, outer ring 937 can be displaced without moving either inner ring 932 or central platform 949. Umbilical hose hole 945 on connecting plate 939 positions a umbilical hose (FIG. 9E 919) with tethering cords (FIG. 9E 993).

This system of protection for the electronic devices central to the device is representative of a category of such systems, in which parts are arranged such that some parts isolate movement from other parts. FIG. 9A is an exemplary representation of such devices.

Holding bars 933 thread through holes 936 on inner ring 932, and screw into threading holes 934 in central platform 949. Holding bars 933 include end covers 938. Inner ring 932 is threaded through holes 948 on footings 935.

Footings include press-in locking mechanism 930, in this embodiment a suction cup system made of elastomeric material. The central portion of the locking mechanism 930 includes a concave surface. When this is pressed into place against a rigid target on the underside of a flexible lower liner (FIG. 9B, 923), the shape of the suction cup forms a partial vacuum, holding the liner in place.

In another embodiment, a ring on the bottom of a flexible lower liner may be pressed downward onto locking mechanism 930, which compresses a spring underneath it, also displacing a projecting member that lifts and locks around the lower liner ring. The spring energizes the projecting member to remain in position. Other embodiments may use different locking mechanisms, known to those familiar with the arts.

Platform apertures 947 allow light emissions devices inside the basin 931 of central platform 949 to link with light aggregators and light transmissions lines outside of 949.

Partial view 975 shows a plurality of ring cords 977 attached between inner ring 932 and side wall netting 976, that surround central platform 949, and generate moment resistance. Side cords 978 attach an end cover 938 to a notch 941 on a footing 935 or inner ring 932, and side cords 978 provide attachment locations for lower liner (FIG. 9B, 923) attachment flaps 927. Side wall netting 976, ring cords 977 and side cords 978 form a webbing.

Partial view 970 shows a thin walled, reinforced rigid structure, which comes in two halves, front 970*a* and rear 970*b*, which combine to form structure 970*c*. Structure 970*c* includes a top wall 972 and bottom wall 973. For clarity, 972 is shown partially cut away, so trusses 974 inside may be seen. Structure 970*c* includes tunnels 971, which fit around holding bars 933. Attachment tabs 926 on top wall 972 serve as press-in attachments for the lower liner (FIG. 9B, 923). When assembled, ring cords 977 run parallel to trusses 974 inside structure 970*c* to form unified structure 970*d*, which is embedded around central platform 949, to form a ring assembly (FIG. 9B, 929).

FIG. 9B shows further assembling of the flexible, shock absorbing photodental device for dogs. Ring assembly 929 supports the electronic superstructure, which is composed of a lower and upper flexible liner. Lower flexible liner 923 is installed on the surface of unified structure 970*d* and side cords 978. It is attached to unified structure attachment tabs 926, which fit into grooves on the underside of molded blocks 921. Lower liner 923 also has attachment flaps 927, seen in exploded view such that they align with their attachment location on both lower liner 923 and side cord 978. Dotted lines 928 show these alignment paths, for all attachment flaps 927.

Different embodiments may join the underside of lower liner 923 and unified structure 970d, with bonding, welding, adhesives, tape, or other materials. Regardless of the attachment mechanisms used, attachment flaps 927 can position lower liner 923 correctly. Different embodiments may use any suitable fastening mechanisms for attachment flaps 927, including hooks, hook and loops, adhesives, or other fastening means.

Liner 923 is fabricated from flexible polymer sheet material 922, with side wall 924 that extends around the perimeter of the liner. Side wall 924 has tabs 925 regularly spaced along it. When side wall tabs on lower liner 923 are placed adjacent to side wall buttons on the upper liner (FIG. 9D, 950), and tab and button are pressed together, they form an attachment enclosing the superstructure. A hole 920 in lower liner 923 fits over the central platform basin 931, leaving it exposed.

Lower liner 923 contains molded blocks 921 comprised of any suitable material to cushion or support electronic devices, such as a tray or molded insert made from foam, plastic, or the like. Blocks 921 may be configured to create cavities 918 in which electronic devices may be secured. Other cavities 913 may be configured to position lightwave aggregators (FIG. 9C, 912), a portion of which are placed in the cavities, where they connect with light emitting components through central platform apertures (FIG. 9C, 947). Lightwave aggregators merge into coupling-in components (FIG. 9C, 914), supported on shelf 915, connected to light transmission lines that pass through 917. In some embodiments an electric line is used to power the assembly, rather than batteries. Shelf 906 provides a route for electric lines into and out of the superstructure.

FIG. 9C shows further assembling of the flexible, shock absorbing photodental device for dogs. A stage 902 is positioned inside central platform basin 931, with six orifices 903 (alternatively, any other number) that six piezoelectric cooling devices 904 fit under. Each cooling device 904 is secured to the stage 902 by a securing pin or other threaded or smooth insert. Six light emitting devices (LEDs) 901 fit over orifices 903, with rod, pin, or threaded inserts that attach them firmly.

Angled pipe fittings 909 act as a relay station for propagation of light emitted by LEDs 901, to light pipes 911. In this embodiment, angled pipe fittings 909 and light pipes 911 are each fashioned as a solid body transparent or transmissible to light. Both their structures and shapes produce total internal reflection. Structurally, they have a core surrounded by an optically less dense medium, so that below a critical angle light will not escape the core. Angled pipe fittings 909 are shaped so their upper surfaces follow a critical angle curve, so all light incident on them is reflected. This curve is the aggregation of points tilted to be within the critical angle. Light emitted on stage 902 is internally reflected through angled pipe fittings 909 in the direction of light pipes 911.

Angled pipe fittings 909 may not have any reflective surfaces, however if the angled movement of light is above the critical angle of total reflection a reflective coating of the "ceiling" of angled pipe fittings 909 may be used. Light pipes 911 receive light from angled pipe fittings 909, directly or through lenses. Light pipes 911 are coupled to lightwave aggregators 912, through platform apertures 947. Lightwave aggregators 912 are internally reflecting light movers, which are designed by combining critical angle curve lines for some edges, coupled with other curves or flat shapes, which concentrates light transmission. The actual design is dependent on material refractive indices.

By using the design principal of combining critical angle curves for some shape lines, along with other parabolic and flat shape lines, lightwave aggregators 912 may have their output coupled to a thinner light guide. In this way three transport chambers converge into the single coupling-in component 914, which injects the light into optic pipes, guides, tubes, or fibers 916, which thread into umbilical hose 919.

Sensor controller 909 is attached to stage 902. Sensor feedback line 906 threads through umbilical hose 919, through a special orifice (not visible) in the central platform, ending at sensor controller 909.

Electronic devices are positioned on the right side of the lower liner 923. Six battery holders (alternatively, any other number) 908 fit between molded blocks cavity 921a, attached by any suitable method. LED (or other light emission technology) driver 907 fits between molded blocks cavity 921b, attached by any suitable method.

Figure 9D:
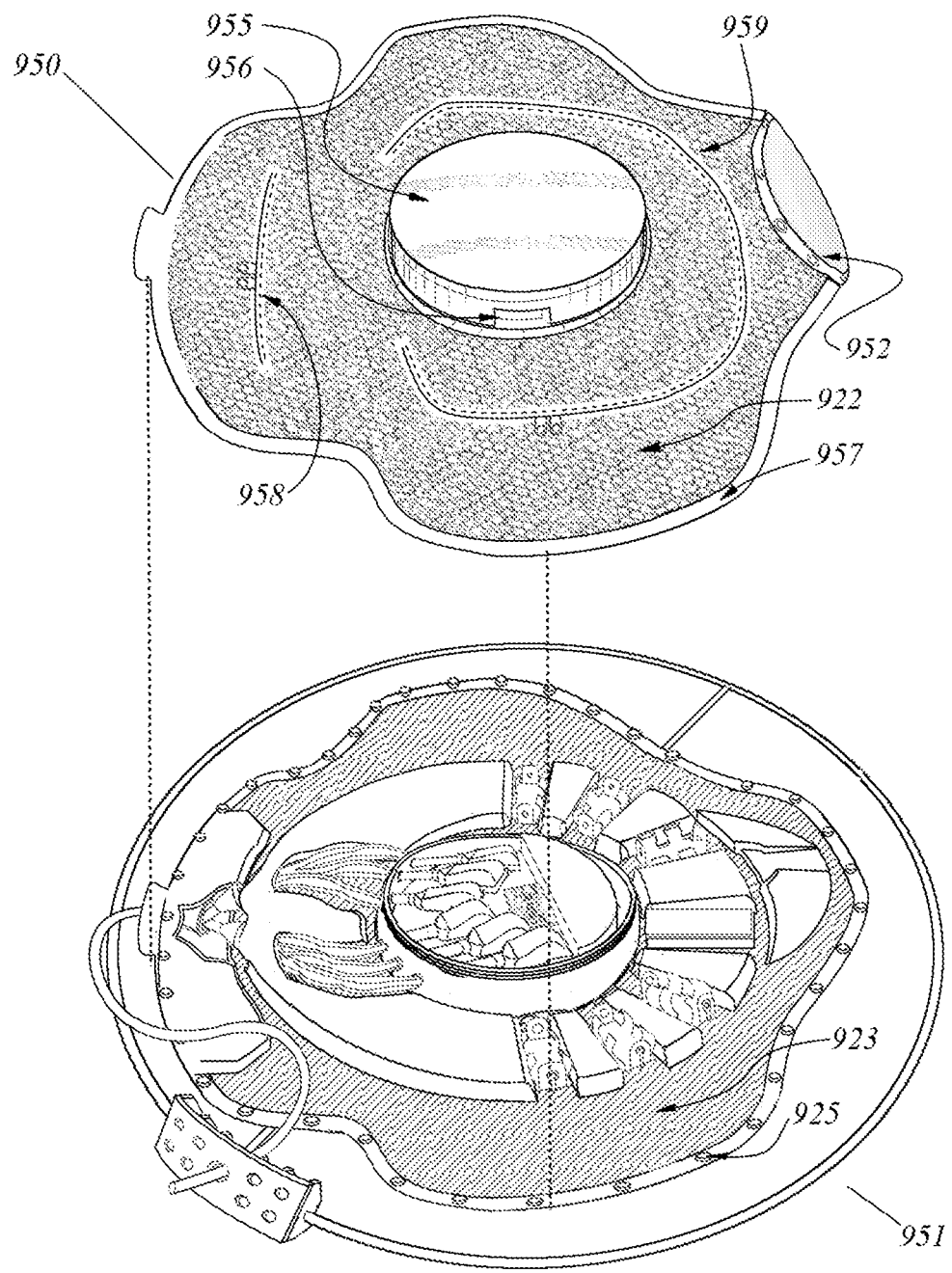
FIG. 9D is an exploded view of a further assembled embodiment shown in FIG. 9A.
Figure 9E:
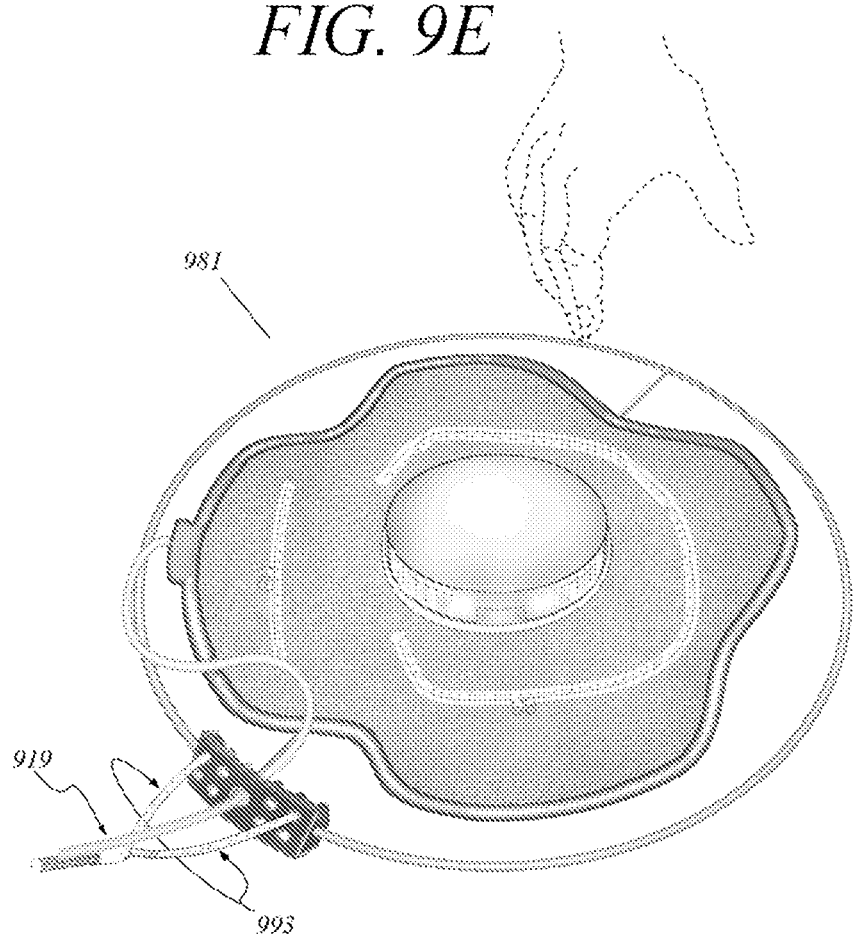
FIG. 9E is a fully assembled view of the embodiment in FIG. 9A.

FIG. 9D shows further assembling of the flexible, shock absorbing photodental device for dogs. The light emissions assembly 951 includes lower liner 923, on which the electronic and light emitting components are positioned. Upper liner 950 is fabricated from flexible polymer sheet material 922, with side wall 957 that extends around the perimeter of the liner. Side wall 957 has slots 952 (visible where the underside is lifted) regularly spaced along its underside. These slots 952 attach to side wall tabs 925 on lower liner 923, by pressing the slots 952 and tabs 925 together.

FIG. 9E shows final assembling of the flexible, shock absorbing photodental device for dogs. The apparatus 981 is configured for transport, and can be attached to anchor objects indoors or out. Umbilical hose 919 contains light pipes, guides, tubes or fibers, which travel to a dog dental device at a distance between one and three meters, or other distance. Tethering cords 993 attach to apparatus 981 and run parallel to the umbilical hose 919.

Figure 9F:
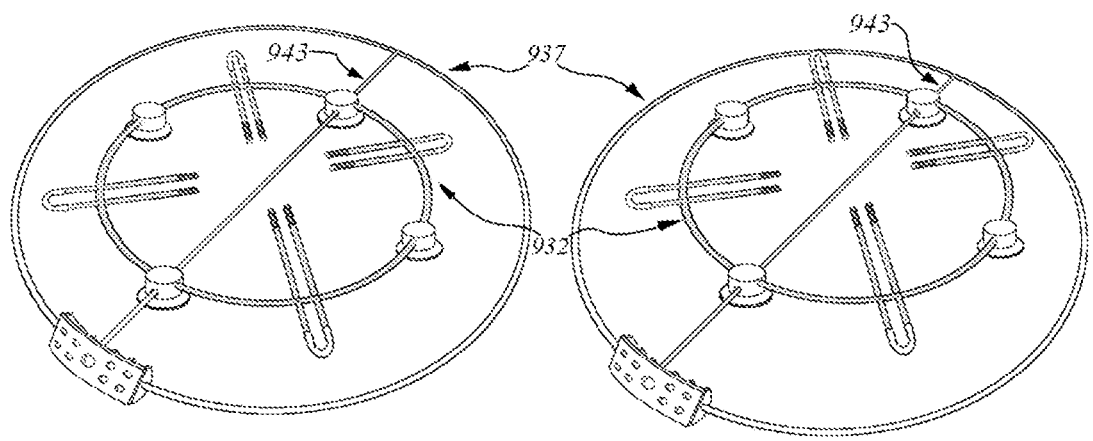
FIG. 9F is a schematic view of the embodiment in FIG. 9A.

FIG. 9F shows the skeletal apparatus that enables a photodental device for dogs to absorb shocks. The present invention, illustrated in FIG. 9F, recognizes that to isolate electronic components from animal forces that can yank, pull, and rapidly move them, it's necessary that some components help to absorb shock, other components help to adjust to shock, and other components remain largely untouched by shock. In this particular embodiment, outer ring 937 absorbs shock, and moves along mounting bar 943, which enables it to adjust to shock, thereby isolating inner ring 932 from shock.

However, other contemplated embodiments include the absence of separate rings and, therefore, only the electronic component area remains. And, of course, other patterns of shock absorption and adjustment would work as well as this embodiment, including using springs, sensors, magnets, and other structural patterns, as would be appreciated by those of ordinary skill in this art.

Figure 9G:
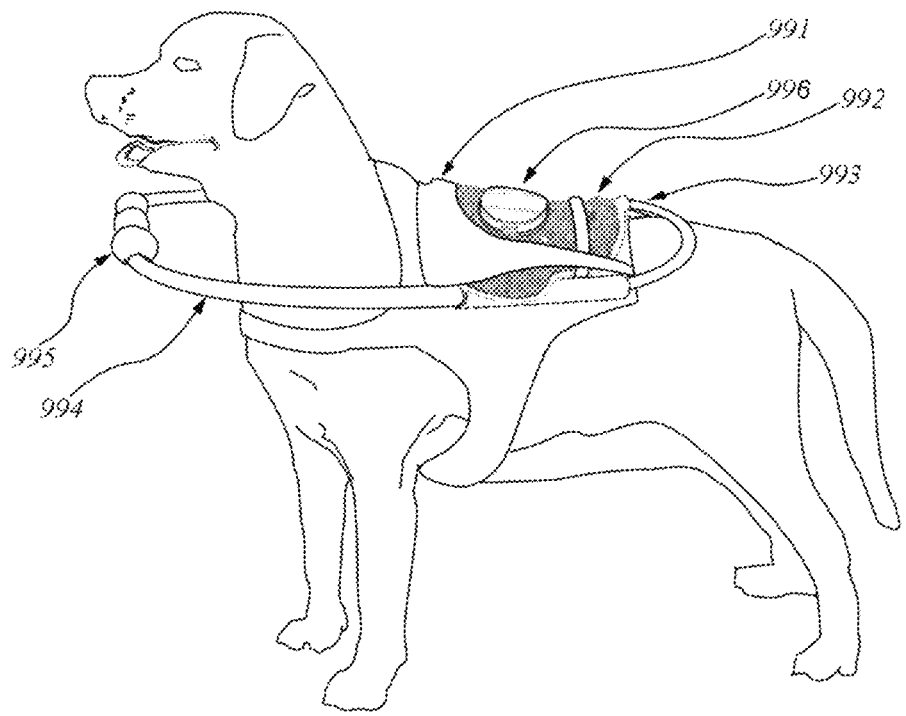
FIG. 9G is an illustration of an alternative use of the embodiment in FIG. 9A.

FIG. 9G shows a different embodiment, in which the pad or mat 992 can be removable from the holding bars and central platform and, with certain adjustments, be attached on a dog's back, for example, secured with attachment belts 991. The umbilical hose 993 is inserted into a tube 994 that wraps around the dog's body, and injects light into a chew device 995, that is a movable body containing an illuminating member, accessible to the dog.

In a different embodiment, the pad or mat, when removed, with adjustments, can be packed for travel or other uses.

Figure 10A:
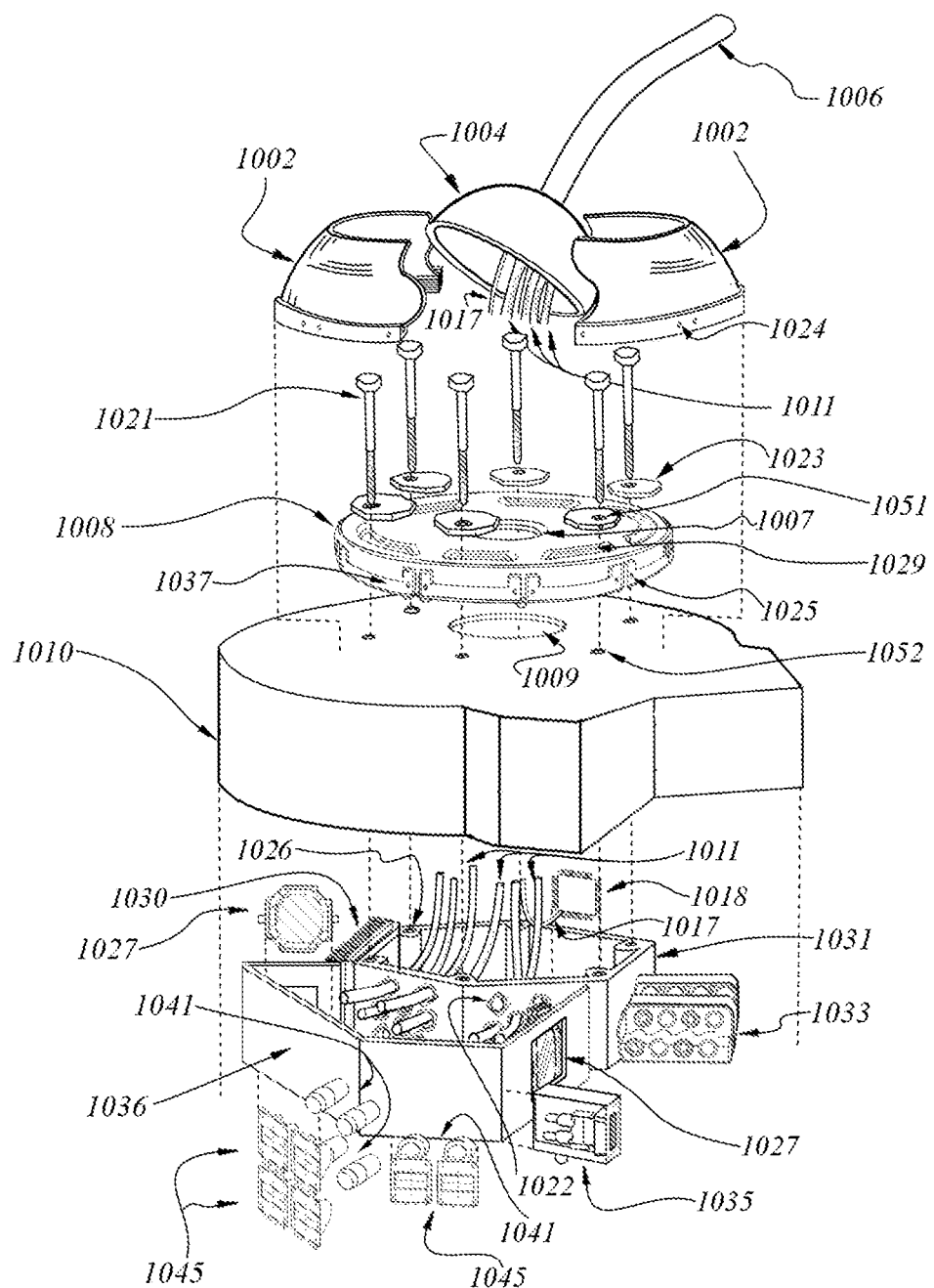
FIG. 10A is an exploded view of a swivel ball photodental device for a dog.

FIG. 10A is an exploded view of an embodiment for a base for a photodental device for dogs, that shows the first steps in its assembly. It employs a swivel ball structure to maximize the rotation and direction of a umbilical hose 1006. A partial spherical female hub 1002 is configured to engage a partial spherical mating male shell 1004. The female and male mating portions together form a swivel ball structure when they are mounted in the device.

As would be appreciated by those skilled in the art, the male shell 1004 is retained by the female hub 1002 to prevent vertical travel of the male shell 1004. Accordingly, corresponding features on the inner edge of the female hub 1002 and the outer edge of the male shell 1004 prevent the male shell 1004 from moving vertically relative to the female hub 1002, but let the male shell 1004 rotate about its longitudinal axis.

Six (or any other number) light transmission lines 1011, and sensor line 1017, exit the umbilical hose 1006 beneath the dome of male mating shell 1004, and pass through aperture 1007 on guide plate 1008 and the apertures 1009 on housing 1010. Inside housing 1010 light transmission lines 1011 pass through apertures 1022 in hexagon 1031 (or another n-gon, or other shape), into light room 1036. Each light transmission line is coaxial to the optical axis of a light pipe fitting 1041, and each light transmission line is bonded, inserted, or otherwise interconnected in a secure and close-fitting way, with a light pipe fitting 1041. Each light pipe fitting 1041 tightly fits around a light emission source, in this embodiment LEDs 1045.

A plurality of threaded inserts 1025 are positioned along a sidewall 1037 of guide plate 1008. During assembly of the female hub 1002, pins, screws, or other attachment devices are inserted into threaded orifices 1024 and secured to sidewall 1037 via threaded inserts 1025.

When assembled, the guide plate 1008 is placed on top of housing 1010 so that passages 1029 align with housing orifices 1052. A heavy washer 1023 is placed over each passage 1029, with its orifice 1051 directly over a housing orifice 1052. Thereafter each threaded fastener 1021 is inserted through the aligned orifices, 1051 and 1052 so that each threaded fastener 1021 threadingly engages within a threaded passage 1026, located in hexagon 1031.

Hexagon 1031 includes sensor controller 1018, to which sensor line 1017 is attached. In this embodiment, battery holder 1033 and LED driver 1030 are attached to hexagon 1031 exterior planar surfaces. Light room 1036 is attached to hexagon 1031, where light producing elements 1045 inject light into light pipe fittings 1041. Room 1036 has piezoelectric cooling devices 1027 at either end, which circulate air between the room 1036 and the environment outside it. Other cooling devices may be used. A USB recharging port 1035 is attached to light room 1036.

Figure 10B:
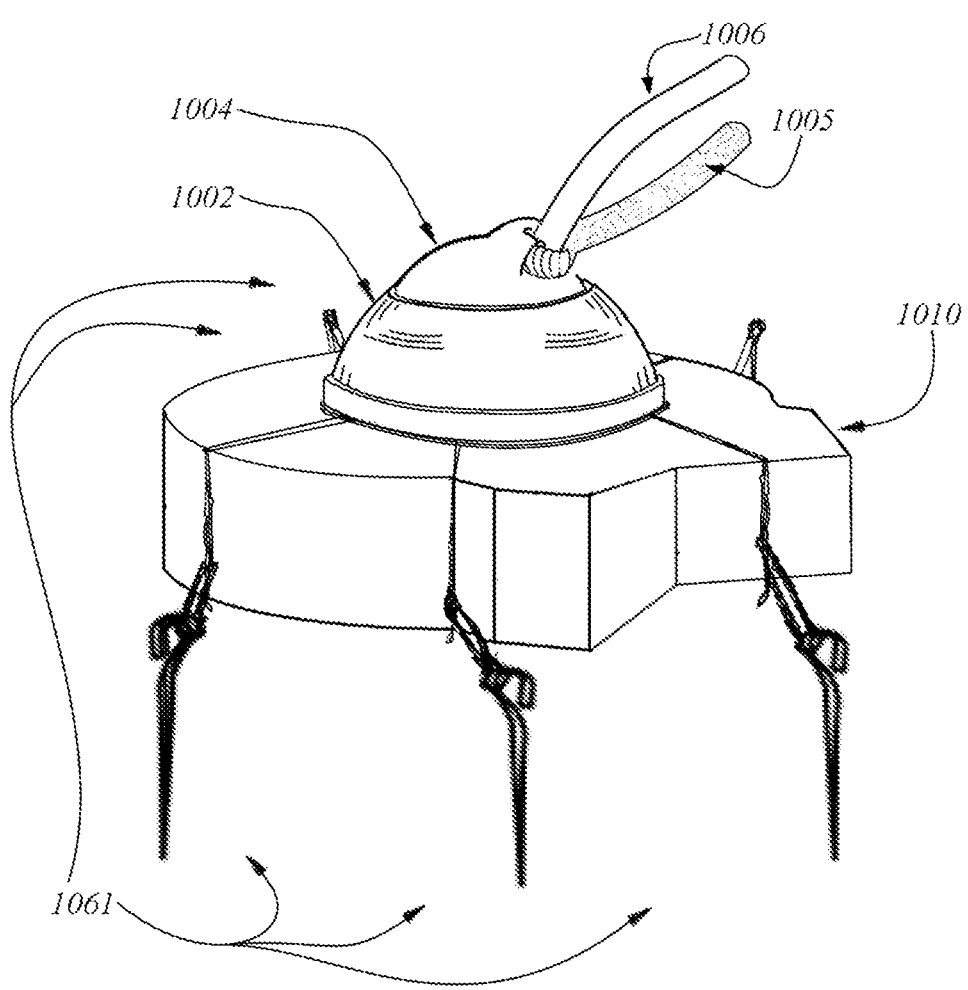
FIG. 10B is a fully assembled view of the embodiment shown in FIG. 10A.

FIG. 10B shows further assembling of a base for a photodental device for dogs. In this embodiment light guides, pipes, or fibers are inside a umbilical hose 1006, which exists the male portion 1004 of a swivel assembly. A tethering cord 1005 is also attached to the male portion 1004. The female portion 1002 of the swivel assembly holds the male portion 1004 in place. Housing 1010 is held down using mechanisms appropriate for indoor or outdoor use. In this embodiment, pegs 1061 are to be hammered into the exterior ground, to hold the photodental device in place.

Figure 11:
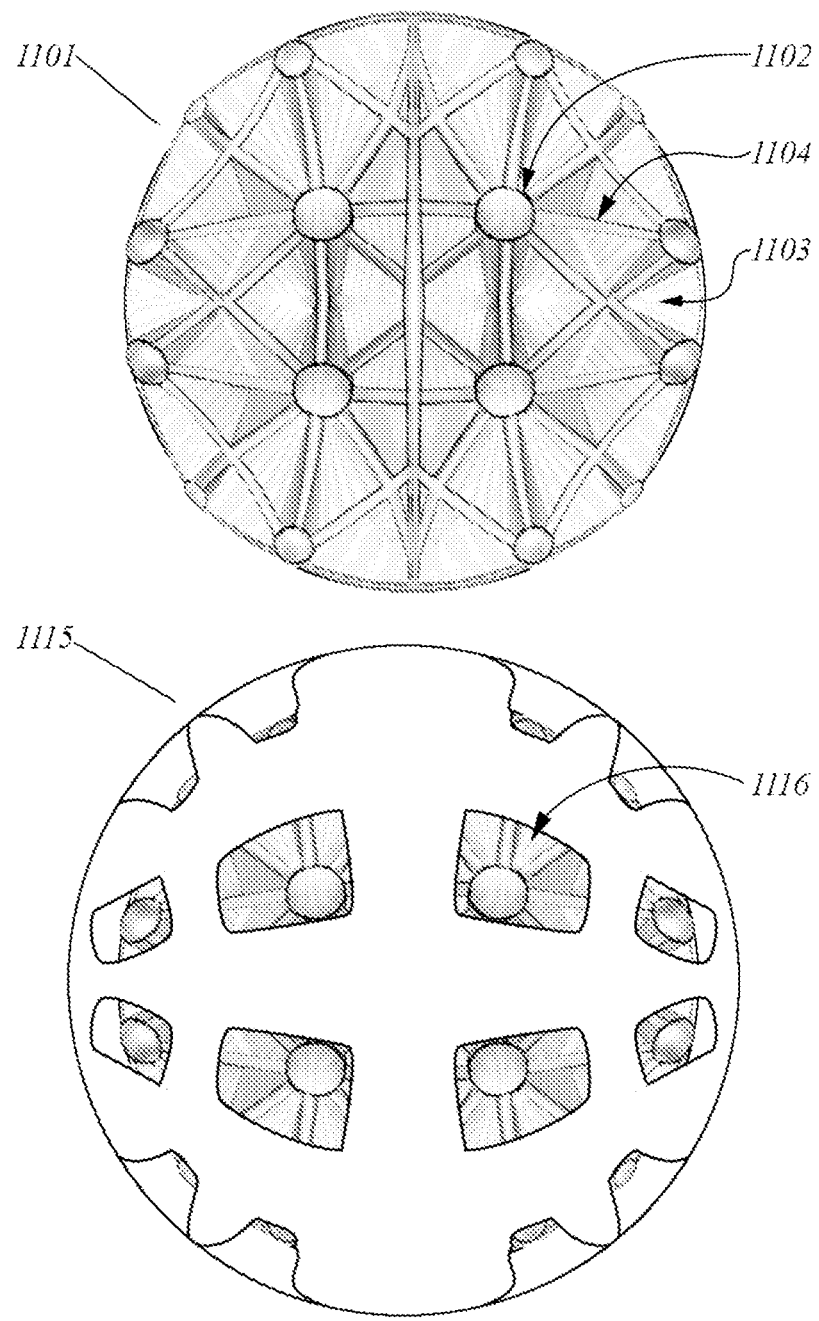
FIG. 11 illustrates protective components of a ball-like photodental device for a dog.

FIG. 11 shows the protective components of a ball-like photodental device for dogs, called a manifold. In this embodiment the protective components are made of resilient materials like metals, and are shaped to maximize resistance to externally imposed stress and strain. Illuminating member manifold 1101 comprises a plurality of discrete protruded elements comprised of, in this embodiment, generally columnar shapes 1102 and linear shapes 1104 in triangular patterns 1103. Other embodiments may use columnar and/or non-columnar shapes, in circular, oval, square, free-form, and other patterns.

The design qualities of this structure are advantageous. Columnar shapes 1102 are flexible segment joints that allow slight deformations. Linear shapes 1104 are horizontal braces capable of resisting forces produced by dog jaws and teeth. Linear shapes 1104 stiffen the structure. By providing a plurality of substantially rigid shapes, the tensile strength of the substance being reinforced is substantially increased. The linear shapes, further, include features that provide strength and rigidity for mounting columnar shapes 1102. Each protruded element 1102 and 1104 may couple to a base structure, plate, or other surface, or alternatively, be formed as part of the surface (by casting, machining, or other methods).

The embodiment being a light emitting device enclosed in resilient protective components, certain columnar shapes 1102 are hollow to permit light passage from inside the ball. These columnar shapes 1102 have a dimension that is slightly larger than the aperture at their base, from which light emits.

Illustration 1115 shows a external environment-facing housing that encloses the manifold. The housing contains a plurality of openings 1116, the openings permitting light from the interior of the device to pass into the external environment. The openings are distributed uniformly around the housing, and snuggly contain the manifold. The openings are configured directly over hollow columnar shapes 1102, where protective component strength is highest. Openings may be filled with transparent material, or may be empty. If dog teeth penetrate onto the columnar shape, their materials, structures, and shapes will prevent damage.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more liquids with low refractive indices (e.g., mineral spirits) may be used in connection with aspects of the invention, as light transmission lines, if desired, for example, to facilitate large radiation dosages or to extend the length of optical transmission lines. The same may hold with respect to other aspects of the invention.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. A movable body for safely radiating the oral cavity of an animal, comprising:
   a first separable part including a first peripheral portion that defines a chamber;
   a means for connecting at least one connector on the first peripheral portion to a second separable part;
   at least one light emitting element in the chamber;
   at least one opening disposed on the first peripheral portion for light to radiate out of the chamber;
   at least one heat dissipation element thermally coupled to at least one light emitting element;
   the first peripheral portion including at least one region where heat escapes;
   the first separable part comprising one or more systems not susceptible to time-dependent deformation, the systems selected from the group consisting of (a) opaque materials, (b) bracings, (c) stereotomic designs, and (d) mixtures thereof;
   the second separable part comprising:
   a second outer peripheral portion, a second inner peripheral portion;
   at least one connector on the second separable part to connect to the first separable part;
   a resilient material that absorbs impacts interposed between the second outer peripheral portion and the second inner peripheral portion;
   at least one hole in the resilient material, the at least one hole communicating the light radiating from the first separable part to an external environment;
   a modulus of elasticity of the second separable part is at least 20% less than a modulus of elasticity of the first separable part;
   wherein periodontal disease is reduced while material or structure damage that harms the animal is prevented, by protecting the at least one light emitting element in the non-deformable first separable part and radiating light suitable for inactivating periodontal pathogens through the second separable part that absorbs impacts.

2. The movable body of claim 1, wherein the second outer peripheral portion includes at least one photosensitizing compound selected from the group consisting of essentially the following: pheophytins, pheophorbides, phenoxazines, phenothiazines, purpurins, fluoresceins, merocyanines, porphycenes, chlorin derivatives, cyanine derivatives, porphyrin derivatives, coumarin derivatives, psoralen derivatives, chlorophyll derivatives, thiophene derivatives, methylene blue, toluidine blue, titanium dioxide, quinones, gallium, aminolevulinic acid, antrocylines, texaphyrins, sapphyrins, hypericin, flavins, phenols, bergapten, rose bengal, carotenoids, curcuminoids, indigoids, rubrene, retinoids, rhodamines, verdins, squaraines, corrins, croconiums, azo compounds, indolenium, natural food dyes, chromophore/fluorophore dyes, synthetic color dyes, xanthene dye, annatto, turmeric, heme, and vitamins.

3. The movable body of claim 1, wherein the movable body is configured to activate in response to at least one of the following inputs: in response to a user controlled switch located on the movable body, in response to a user command transmitted wirelessly to the movable body, and at the signal of an integrated circuit when at least one sensor detects a predetermined environmental value.

4. The movable body of claim 1,
   wherein the first separable part is a separate component with a means of preventing the animal from contact with it, the preventing means configured to protect the first separable part from damage;
   a means for the first separable part to be attached to the second separable part by mechanical or elastomeric attachment with an integrated shock absorption means;
   wherein the at least one light emitting element in the first separable part injects the at least one light emitting element's radiation into one end of at least one light path; and
   a means for receiving the radiation at the other end of the at least one light path in the second separable part such that the animal may have the radiating light suitable for inactivating periodontal disease.

5. The movable body of claim 4, further comprising a quick release connection means for quickly releasing the at least one light path received at the second separable part, in response to at least one releasing force applied to the second separable part, the at least one releasing force being substantially independent of any compressive force being exerted on the second separable part, the quick release connection means being suitable for preventing a transfer of the at least one releasing force to the first separable part, the quick release connection means further comprises:
   a first component fixably attached to the second separable part;
   a second component adapted to receive the radiation and project it into the first component, and the first component adapted to project the radiation into the second separable part;
   a coupling assembly releasably connected to the second component and the first component;
   a quick release mechanism operable between a locked position in which the coupling assembly locks the second component to the first component, and an unlocked position in which the coupling assembly disconnects the second component from the first component when the releasing force is applied to the quick release connection means.

6. The movable body of claim 4, further comprising:
a support object attached to the first separable part, wherein the support object is configured with a slide channel; and
   a response object linked to the support object, comprising:
      a linkage element configured to slidably move in the slide channel to allow a translation of the response object along the slide channel direction without moving the support object; and
     the response object adapted to an attachment to the second separable part;
     whereby movement of the animal causes a movement of the second separable part causing the response object to move wherein the linkage element slides along the slide channel in the support object to prevent movement of the support object.

7. The movable body of claim 4, further comprising that the first separable part is set on a piece of material, the material is disposed on at least a portion of a harness attached to the back of the animal, wherein the at least one light emitting element injects the radiation into, the at least one light path;
   the at least one light path configured to pass around the side of the animal to enter the second separable part, the second separable part adapted to be disposed close to the animal's mouth and reachable by the animal's mouth so that the animal may have the radiating light suitable for inactivating periodontal disease.

8. The movable body of claim 4, further comprising that the first separable part is configured with an apex dome port, the dome port having an opening for the at least one light path; the dome port being pivotably attachable to the first separable part such that the dome port in use may pivot about a single pivot axis through a range of angles.

9. The movable body of claim 1,
   wherein the first separable part is a separate component with a means for blocking the animal from placing the first separable part in the animal's mouth, the blocking means configured to protect the first separable part from damage;
   wherein the at least one light emitting element injects the radiation into one end of at least one light path and including a means for receiving the radiation at the other end of the at least one light path in the second separable part.

10. The movable body of claim 1, further comprising the at least one light emitting element disposed in the first separable part includes at least one concave parabolic reflector individually associated with the at least one light element, the at least one reflector directing the radiation toward the at least one opening in the first peripheral portion, the curvature of the at least one reflector being selected to produce a plurality of substantially directed light beams at the at least one opening.

11. The movable body of claim 1, further comprising the first peripheral portion comprises a hard body shell, the hard body shell comprising one or more shell sections with side flanges joined by attachment to form the chamber, the at least one opening in the hard body shell sized for the at least one light emitting element and to facilitate entry of air, each of the at least one light emitting elements alignably positioned facing a respective one of the at least one openings in the hard body shell, said hard body shell being constructed from a metal or metal compound.

12. A method for use in the protection of a small animal from harm during oral photodynamic radiation, comprising the steps of:
   configuring a movable object with a first separable part surrounded by a second separable part, so that the second separable part can be removed and replaced;
   providing the first separable part with a support means of substantially rigid and incompressible material and a structure that resists time-dependent deformation forces;
   providing the second separable part with resilient support means that a small animal can chew;
   providing the first separable part at least one light emitting element, and directing the at least one light emitting element's light emission on a light transmission path through the first separable part and the second separable part towards areas outside;
   wherein the light emission is unhindered by the support means that protect the small animal from harm when biting the movable object, and wherein an owner of the small animal replaces the second separable part when its degradation threatens the support means of the first separable part.

13. A method as set forth in claim 12, including:
connecting a unit to the movable object;
providing a means for impeding access by a small animal to the unit with one or a plurality of barriers;
providing the unit at least one light emitting element, and directing the at least one light emitting elements light emission in an optical transmission cable;
providing a shock absorbing cable exit structure on the unit;
providing the moveable object an input member having an input surface in a direction orthogonal to the light transmission path, with at least one through hole within which the light emission on the optical transmission cable passes, the at least one through hole leading into the movable body;
wherein the light emission is directed towards areas outside of the second separable part.

* * * * *